United States Patent [19]

Michalik

[11] Patent Number: 4,640,616
[45] Date of Patent: Feb. 3, 1987

[54] AUTOMATIC REFRACTOMETER

[75] Inventor: John K. Michalik, Sloan, N.Y.

[73] Assignee: The Cambridge Instrument Company plc, Cambridge, England

[21] Appl. No.: 678,932

[22] Filed: Dec. 6, 1984

[51] Int. Cl.$^4$ .............................................. G01N 21/43
[52] U.S. Cl. ....................................................... 356/136
[58] Field of Search ................................. 356/128-137

[56] References Cited

U.S. PATENT DOCUMENTS

| | | | |
|---|---|---|---|
| 3,311,014 | 3/1967 | Witt et al. ............................ | 356/133 |
| 3,540,808 | 11/1970 | Harmon et al. ...................... | 356/414 |
| 3,628,867 | 12/1971 | Brady .................................. | 356/136 |
| 4,469,441 | 9/1984 | Bernier et al. ....................... | 356/316 |

FOREIGN PATENT DOCUMENTS

| | | | |
|---|---|---|---|
| 71143 | 2/1983 | European Pat. Off. ............. | 356/128 |
| 2642891 | 3/1978 | Fed. Rep. of Germany ...... | 356/135 |
| 40187 | 3/1977 | Japan .................................. | 356/136 |
| 257127 | 8/1926 | United Kingdom ................ | 356/136 |
| 462332 | 9/1937 | United Kingdom ................ | 356/136 |
| 2008793 | 6/1979 | United Kingdom ................ | 356/135 |

OTHER PUBLICATIONS

The Electron Machine Corporation Brochure: "Model-Bl-168 In Line Solids Analyzer, " 1968.

Primary Examiner—F. L. Evans
Attorney, Agent, or Firm—Alan H. Spencer

[57] ABSTRACT

An automatic refractometer comprising a photosensitive device having a relatively narrow dynamic range in the form of a linear scanned array including a plurality of photoelectric elements each providing an output pulse during a scan and the amplitude of each pulse being determined by the amount of illumination of the corresponding element by incident light, an optical system for directing light onto the array in a manner such that the particular photoelectric elements of the array which are illuminated by the light are determined by the index of refraction of a light transmitting substance placed in operative association with the optical system, a circuit for converting signals from the array into digital signals containing information as to the amplitudes of the signals from the array, a digital processing circuit for storing respective signals from reference and sample substances placed in operative association with the optical system and for computing the index of refraction of the sample substance by means of a comparison of the stored reference and sample information, and apparatus for providing a read out of the computed result. The digital processing circuit also calculates the percent solids in the sample substance, and the circuit also includes a plurality of channels for containing information to provide different interpretation of the index of refraction computed thereby. The circuit for converting array signals into digital signals comprises a peak detector circuit for detecting peak amplitudes of signals obtained from scanning the array and an analog-to-digital converter for providing digital signals containing information as to peak amplitudes of the array signals. There is also provided arrangements for measuring the temperatures of the sample substance and comparing to a reference for applying a temperature correction to the computed index of refraction, monitoring and regulating the temperature of the component of the optical system to which the sample substance is exposed, and monitoring and regulating the intensity of light incident on the array.

23 Claims, 39 Drawing Figures

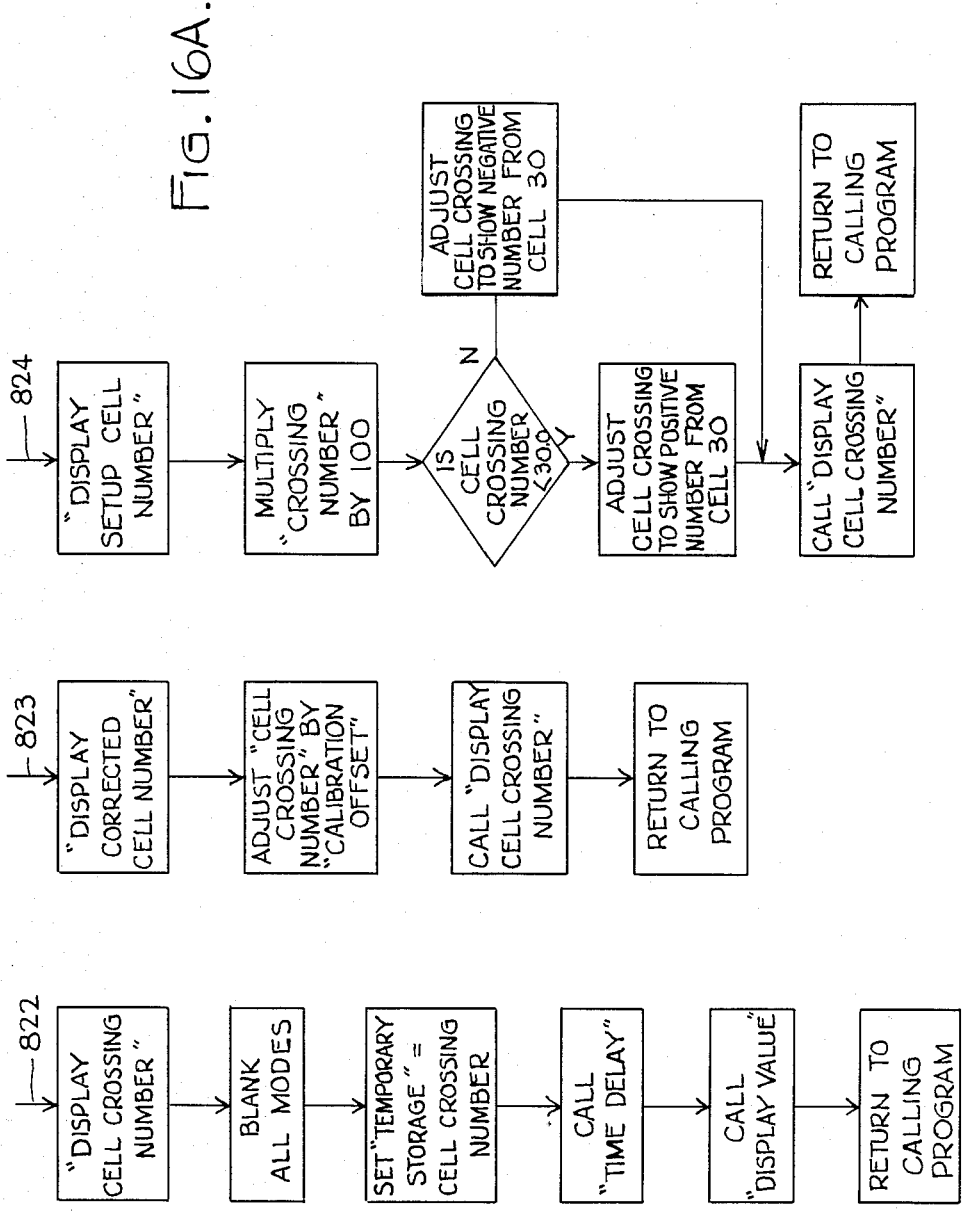

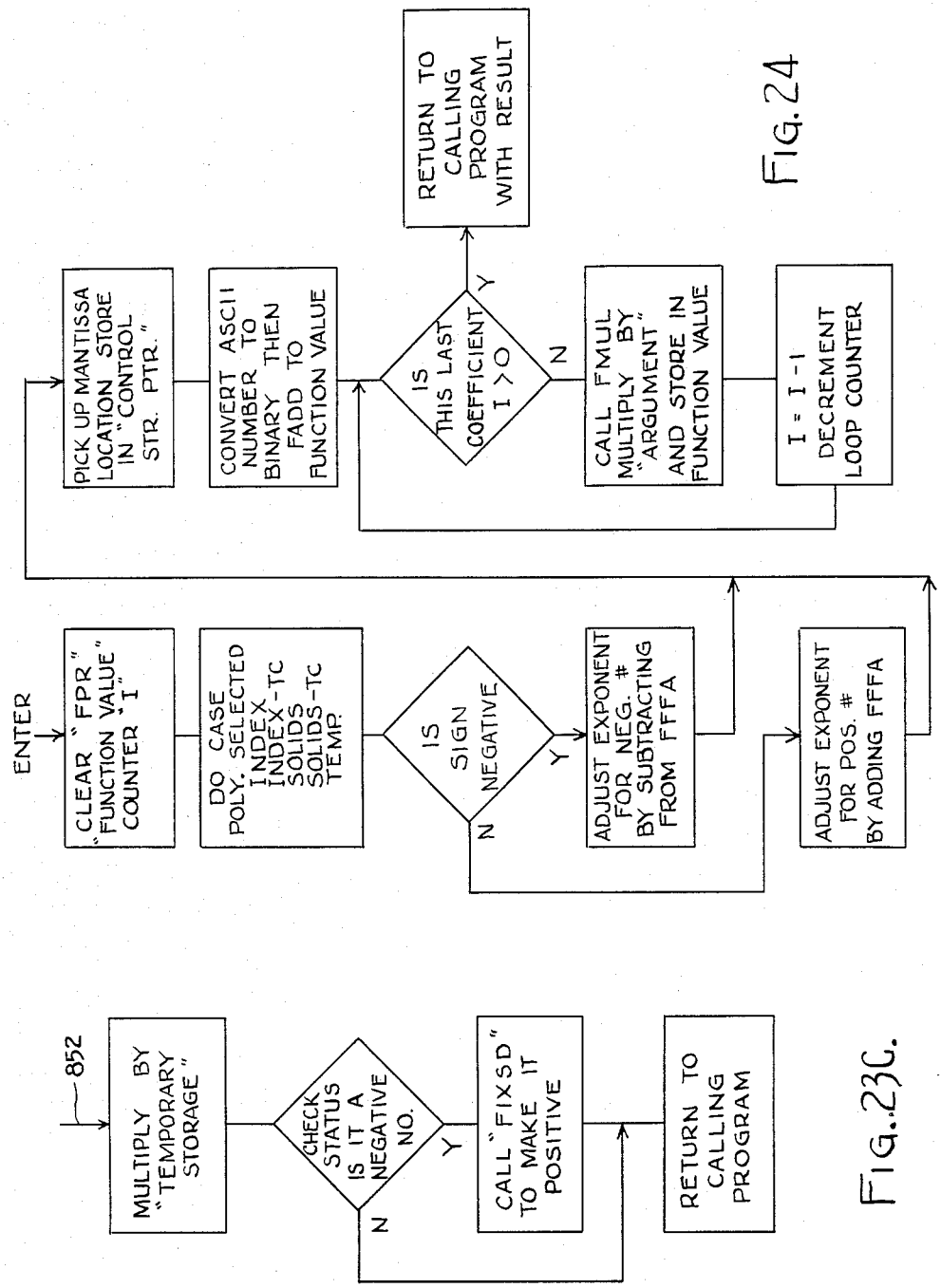

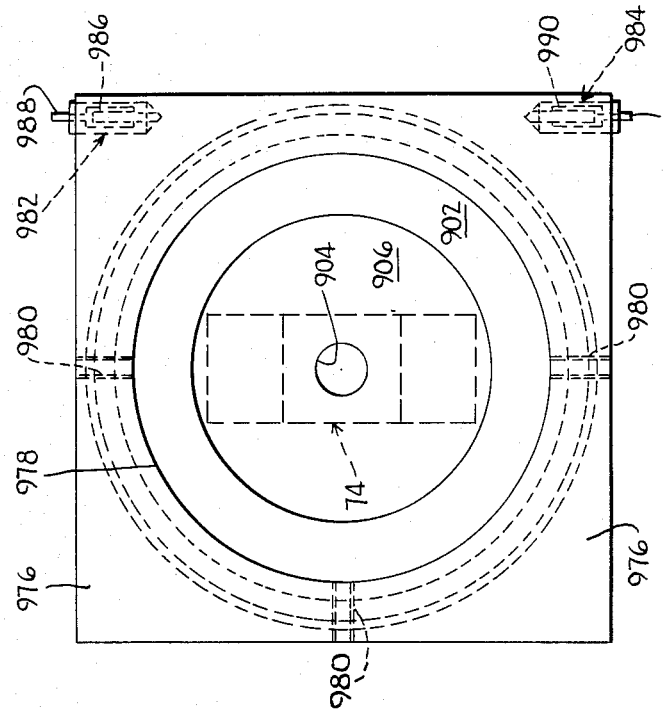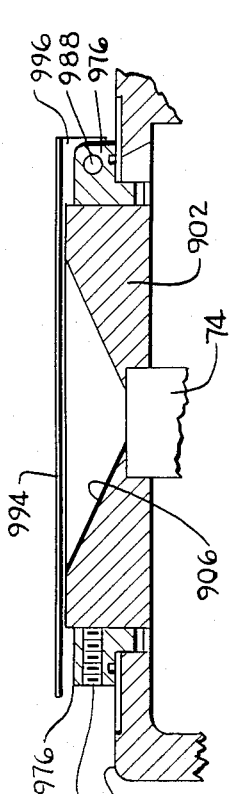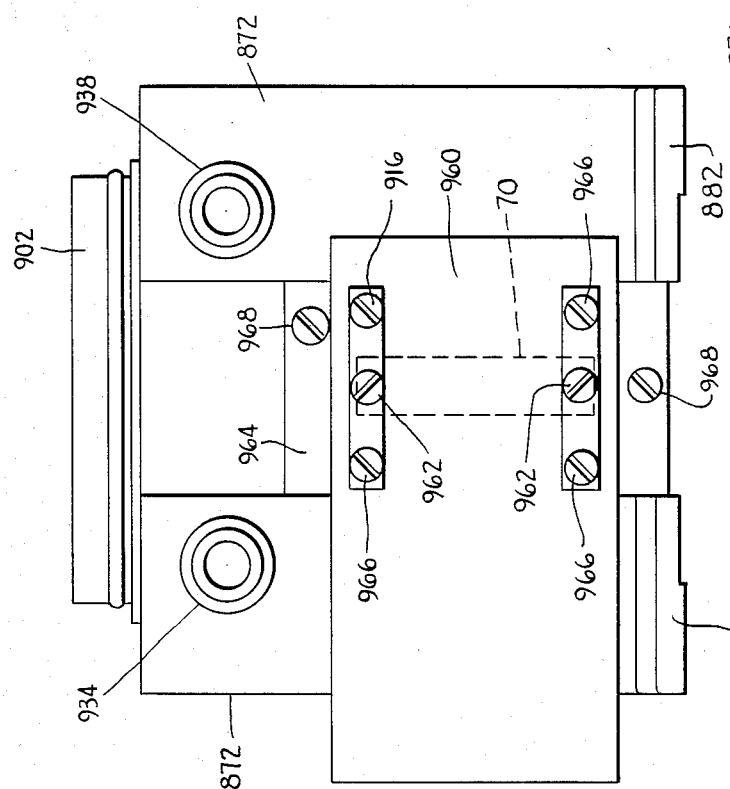

AUTOMATIC REFRACTOMETER

BACKGROUND OF THE INVENTION

This invention relates to the art of refractometers, and more particularly to a new and improved automatic refractometer for measuring refractive index of liquids and determining percent solids therefrom.

Refractometers often are of the type based on measurement of the so-called critical angle of total reflection, in which the position of a boundary or shadow line dividing a field of view into a bright and a dark portion is observed through an eyepiece against a fixed scale or mask. It would be highly desirable to provide an automatic refractometer capable of completely automatic measurements of refractive indexes to eliminate the possibility of human error arising from manual alignment through an eyepiece. It also would be highly desirable to provide such an automatic refractometer utilizing the advantages of digital data processing and capable of calculating percent solids from the index measurements, providing temperature corrections when needed in the refractive index and percent solids determinations, having a plurality of modes of operation, and having multi channel capability for handling a variety of information to provide different interpretations of the index of refraction.

SUMMARY OF THE INVENTION

It is, therefore, a primary object of this invention to provide a new and improved automatic refractometer which eliminates dependence on human operation.

It is a more particular object of this invention to provide such a refractometer for providing a readout of information relating to index of refraction and percent solids in a liquid.

It is a further object of this invention to provide such a refractometer which provides the foregoing readout of information within a relatively smaller range and with a relatively higher degree of accuracy.

It is a further object of this invention to provide such a refractometer having a plurality of modes of operation including determination of both refractive index and percent solids of a liquid and each with and without temperature compensation.

It is a further object of this invention to provide such a refractometer having multi channel capability for handling a variety of information to provide different interpretations of the refractive index determination.

It is a further object of this invention to provide such a refractometer wherein refraction of light by liquid being investigated provides signals which are processed in a digital manner to provide information as to refractive index and percent solids.

It is a further object of this invention to provide such a digital refractometer which is capable of communicating with an external digital processor for re-programming to accommodate changes in characteristics relating to liquids being examined and affecting the determination of refractive index and percent solids.

It is a further object of this invention to provide such a refractometer wherein the temperature of the prism thereof is measured and any needed corrections are made to refractive index and percent solids from the given base temperature.

It is a further object of this invention to provide such a refractometer wherein the optical, photoelectric and other sensitive components thereof are protected from adverse environmental effects such as temperature, contaminants, shock and vibration.

The present invention provides an automatic refractometer comprising photosensitive means having a relatively narrow dynamic range in the form of a linear scanned array including a plurality of photoelectric elements each providing an output pulse during a scan and the amplitude of each pulse being determined by the amount of illumination of the corresponding element by incident light, optical means for directing light onto the array in a manner such that the particular photoelectric elements of the array which are illuminated by the light are determined by the index of refraction of a light transmitting substance placed in operative association with the optical means, means for converting signals from the array into digital signals containing information as to the amplitudes of the signals from the array, digital processing circuit means for storing respective signals from reference and sample substances placed in operative association with the optical means and for computing the index of refraction of the sample substance by means of a comparison of the stored reference and sample information, and means for providing a read out of the computed result. The digital procesing circuit means further includes means to calculate the percent solids in the sample substance, and the circuit means also includes a plurality of channels for containing information to provide different interpretations of the index of refraction computed thereby. The means for converting array signals into digital signals comprises a peak detector circuit for detecting peak amplitudes of signals obtained from scanning the array and an analog-to-digital converter for providing digital signals containing information as to peak amplitudes of the array signals. There is also provided means for measuring the temperatures of the sample substance and comparing to a reference for applying a temperature correction to the computed index of refraction, means for monitoring and regulating the temperature of the component of the optical means to which the sample substance is exposed, and means for monitoring and regulating the intensity of light incident on the array.

The foregoing and additional advantages and characterizing features of the present invention will become apparent upon a reading of the ensuing detailed description together with the included drawings wherein:

BRIEF DESCRIPTION OF THE DRAWING FIGURES

Figure 3:
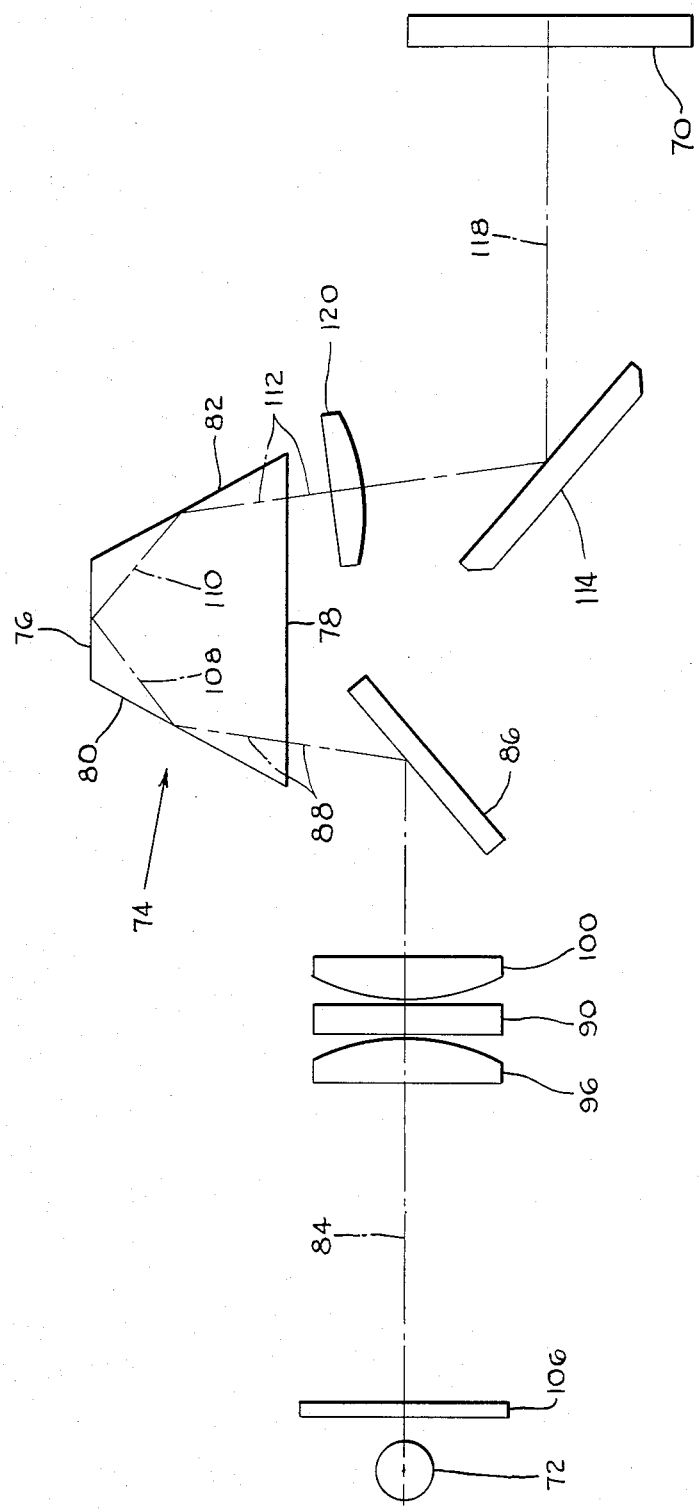
FIG. 3 is a diagrammatic view of the optical system in the automatic refractometer of FIG. 1.
Figure 30:
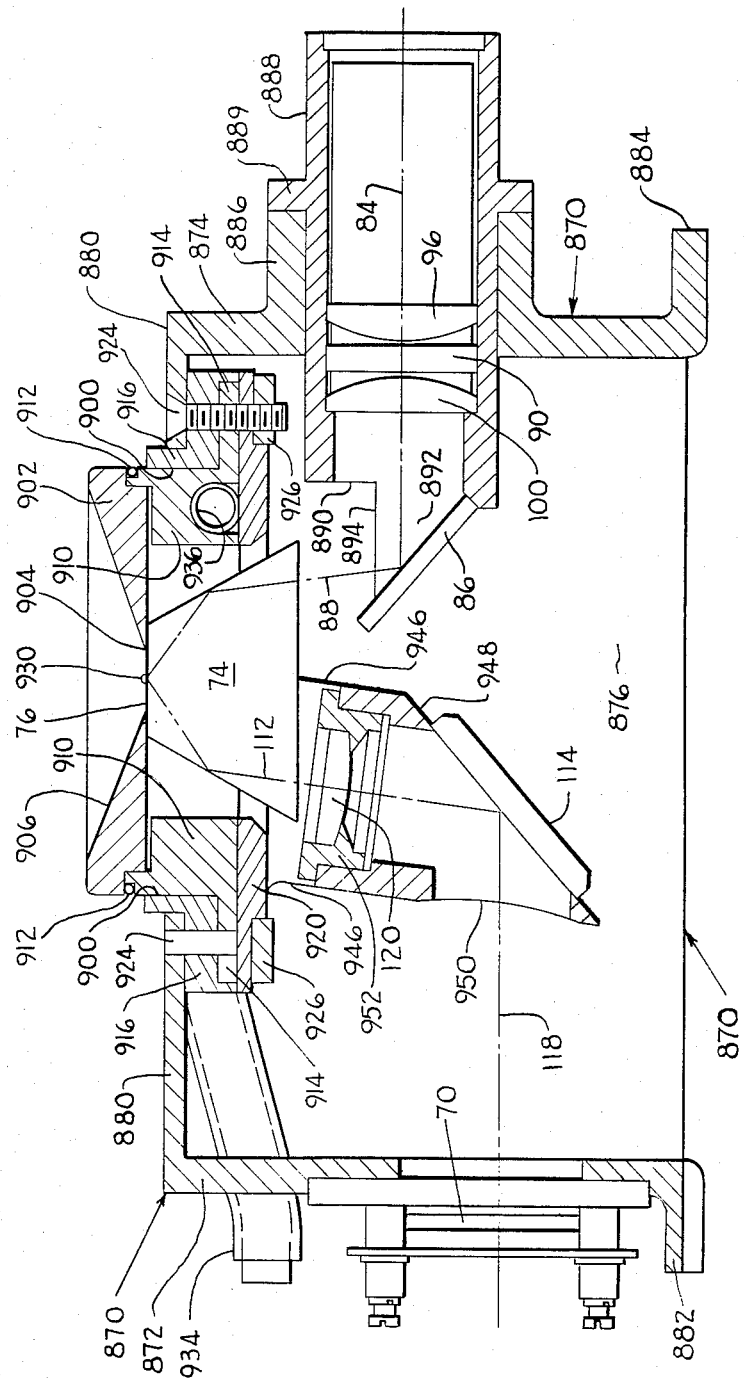
Figure 31:
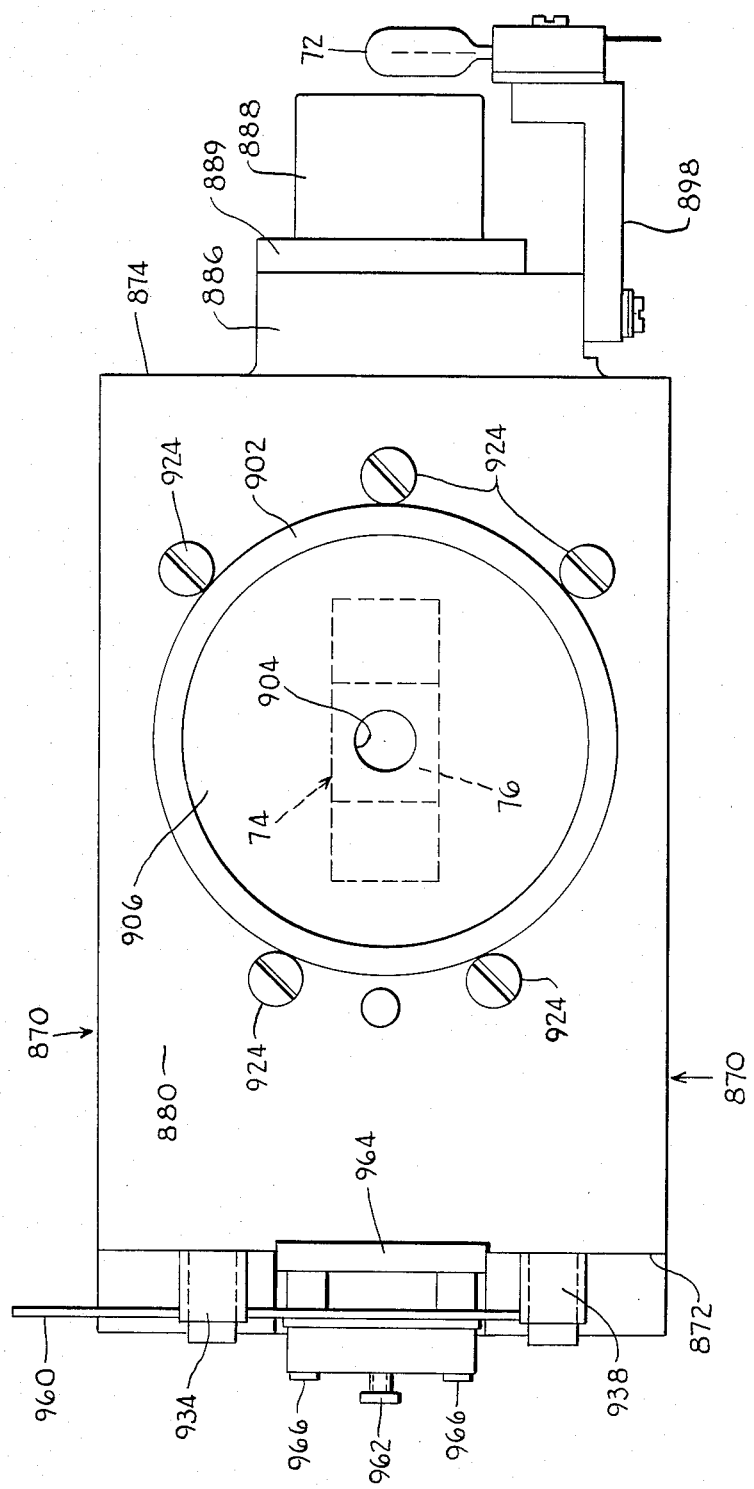

FIGS. 11-29 comprise a flow chart illustrating the program for controlling the automatic refractometer according to the present invention;

FIG. 30 is a longitudinal sectional view of the assembly and frame for supporting the optical components of the system of FIG. 3 in the refractometer housing;

FIG. 31 is a plan view of the assembly and frame of FIG. 30.

FIG. 32 is an end elevational view of the assembly and frame of FIG. 30.

Figure 1:
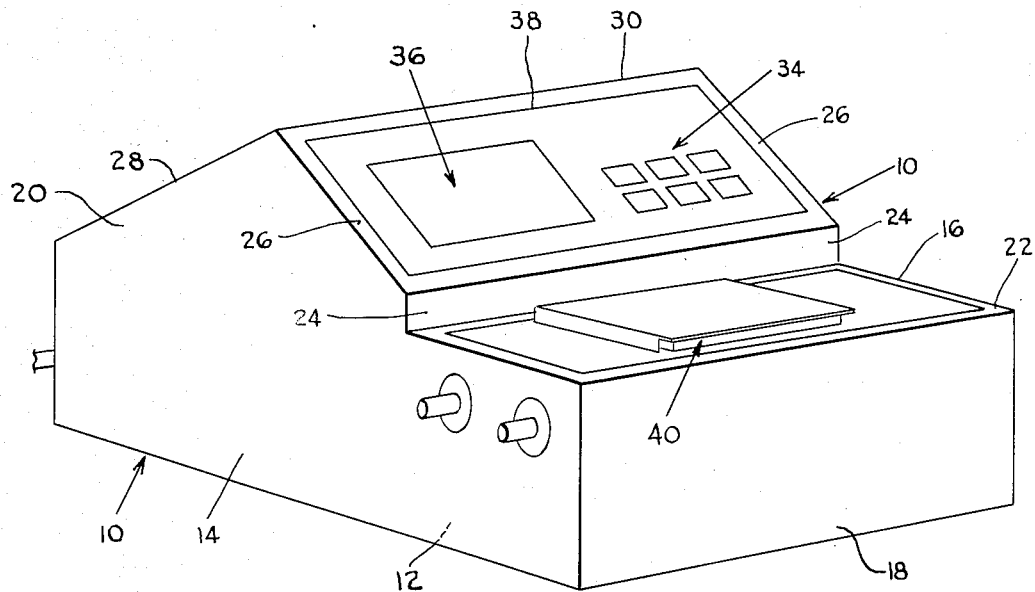
FIG. 1 is a perspective view illustrating the automatic refractometer of the present invention.

FIG. 33 is a fragmentary sectional view illustrating the prism cover and removable connection in the apparatus of FIG. 1; and FIG. 34 is a plan view with parts removed illustrating the cover of FIG. 33.

DETAILED DESCRIPTION OF THE ILLUSTRATED EMBODIMENTS

The automatic refractometer of the present invention, briefly, makes completely automatic measurements of refractive indices without operator intervention and is capable of making calculations to determine percent solids from the index measurements. The refractometer also measures prism temperature and makes corrections if needed to either solids or refractive index from the given base temperature. It has multiple channel capability for handling a number of substances, displays the selected channel along with the selected mode of operation of the instrument, and displays warnings to alert the operator to possible operational errors. When operation of the refractometer is initiated, it measures the light level at a linear scan array therein and then adjusts lamp voltage to obtain an optimum light level at the array. Thereafter, a reference scan of the array is made and information therefrom is stored in a memory for future use. Next, the operator selects one of the measuring modes of the instrument: refractive index (Nd), refractive index temperature compensated (NdTC), percent solids (% Solids), percent solids temperature compensated (% Solids TC) and liquid temperature (Temp C). The instrument is calibrated by taking a reading with water as the liquid and using the result as a reference for future readings. A particular channel is selected according to the liquid being examined. In response to various input channels, the refractometer displays index of refraction, percent solids and temperature for the liquid being examined.

The automatic refractometer according to the present invention is contained within a housing generally designated 10 in FIG. 1 which includes a bottom 12, a pair of side walls 14 and 16, a front end wall 18 and a rear end wall 20. The top of housing 10 as viewed in FIG. 1 includes a flat surface portion 22 extending inwardly from the front wall 18, and surface 22 is disposed in a plane generally parallel to that of the housing bottom 12 so as to be generally horizontal during use. As shown in FIG. 1, the top surface portion 22 extends from front end wall 18 about ⅓ the distance to the rear wall 20, whereupon it meets a relatively short upstanding surface 24 disposed at about a right angle to surface 22. The remainder of the housing top includes a first upwardly inclined surface portion 26 extending rearwardly from surface 24 which meets a second inclined surface portion 28 which extends upwardly and forwardly from the rear end wall 20, the surface portions 26,28 meeting in a peak or edge 30. In the illustrative housing shown the surface portions 26,28 define therebetween an included angle somewhat greater than 90°.

Housing 10 supports a keyboard generally designated 34 for inputing information to the refractometer and also supports a display generally designated 36 for providing a visual display of index of refraction and percent solids information. The keyboard 34 and display 36 are located within a border designated 38 on surface 26. The location and inclination of surface 26 provides convenient viewing of the display 36 and access to the display 36 and keyboard 34 for persons using the instrument.

The refractometer prism assembly (not shown in FIG. 1) is covered by a lid 40 which is pivotally connected to housing 10 at a location near surface 24 in a manner which will be described. Electrical power is supplied to the refractometer within housing 10 by a conductor (not shown) for connection to a standard electrical outlet receptacle providing line voltage.

Figure 2:
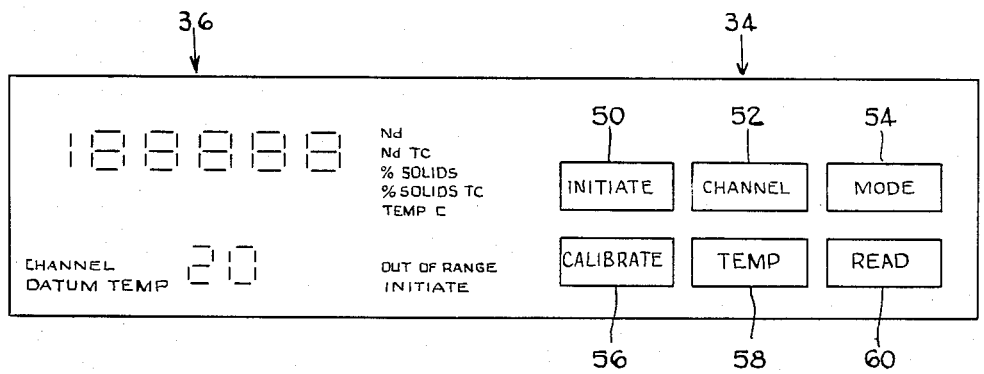
FIG. 2 is a diagrammatic view further illustrating the keyboard and display in the automatic refractometer of FIG. 1.

FIG. 2 illustrates in more detail the keyboard 34 and display 36 of FIG. 1. Turning first to the display 36, the lower portion thereof displays information and the status of the instrument. In the left hand part of the lower portion as viewed in FIG. 2, either "CHANNEL" or "DATUM TEMP" will be displayed along with a corresponding numerical quantity. In FIG. 2, for convenience in illustration, both word quantities are shown along with the illustrative numerical quantity 20. The refractometer of the present invention has multichannel capability where each channel contains information corresponding to various substances for which the refractometer will calculate percent solids after making the refractive index measurement. Accordingly, the particular channel which is selected will depend upon which of those substances the refractometer currently is being used to examine. By way of example, in an illustrative refractometer, there can be as many as 15 channels. The datum temperature is the preprogrammed temperature to which is compensated the particular channel selected according to the solids of interest.

On the other part of the lower portion of display 36, there are two states indicated, only one of which is displayed at a particular time. One indicator is "OUT OF RANGE" which indicates that the refractive index of the liquid currently being examined is out of the range for the instrument. In the refractometer shown and described herein, the refractive index range is from about 1.32 to about 1.50. The "INITIATE" indicator is displayed when the refractometer is first turned on to remind the person operating the instrument to perform such initial or preliminary operations as taking a reference curve which will be described hereinafter. It also signals the need for the instrument to initialize the operational variables in the program, i.e. it indicates that the operator should depress the "INITIATE" key as will be explained. Also, if during the operation of the refractometer the temperature of the prism deviates from a pre-programmed temperature for the selected scale, the "DATUM TEMP" indicator will be displayed as a warning to the operator.

The upper portion of display 36 presents the selected mode of operation of the instrument and the numerical result of the refractive index measurement and the percent solids calculation. In particular, the left hand part provides a read out of the index of refraction with provision for four decimal places, the illustrative range being from about 1.32 to about 1.50 as previously described, a readout of the percent solids calculated from the refractive index measurement, and a readout of temperature.

The other part displays one of five selected measuring modes of the instrument. Only one mode is displayed at any given time, but for convenience in illustration all five modes are shown in FIG. 2. The Nd mode is the measuring mode for index of refraction according to the sodium D-line convention. The Nd TC mode is for refractive index measurement temperature compensated, such as to 20° C. The % SOLIDS mode takes the measured refractive index and calculates the percent solids to provide a value dependent upon the particular channel selected. The % SOLIDS TC mode provides a percent solids value corrected to the temperature as stored to the datum value in the channel. The TEMP C mode if selected gives a readout of the temperature of the liquid being measured. There is also a DATUM TEMP mode which if selected gives a display of temperature value.

Turning now to the keyboard 34, there are six manually operated keys designated 50, 52, 54, 56, 58 and 60 in FIG. 2. Each key, when depressed, commands an operation or series of operations in the refractometer.

Considering first the INITIATE key designated 50, when the electrical power to the refractometer first is turned on, all of the keys 50-60 in the instrument are disabled. The initiate key 50 must be depressed in order to enable the instrument. In response to manual depression of key 50 the instrument operates to measure the light level at the linear scan array in a manner which will be described, and then adjusts the lamp voltage in the instrument to obtain an optimum light level at the array. Thereafter, a reference scan of the array is made and the information obtained from that scan is stored in the instrument memory for future use. If all operations fall within predetermined limits, the upper left portion of display 36 will present an appropriate message, such as the word "HELLO", and then keyboard 34 will be able to accept all other valid commands.

Turning now to the MODE key 54, it is depressed to command a desired one of the measuring modes of the instrument previously described. Key 54 is depressed successively to cycle through the various modes until the desired one is reached as indicated by the display. For example, a single depression of key 54 will command the Nd mode, and if key 54 is not depressed again the display 36 will indicate Nd as previously described. By way of further example, if the % SOLIDS TC mode is desired, key 54 is depressed four successive times until that mode is reached and indicated on display 36.

The CALIBRATE key 56 is depressed to command a sequence of operations to calibrate the instrument for proper reading. First, water is placed on the instrument prism and key 56 is depressed. The temperature of the water on the prism is measured by the instrument, and the computed cross-over of the shadow line is determined by the instrument in a manner which will be described and is used as the reference for all other readings.

The CHANNEL key 52 is depressed to select the appropriate scale measure. Each time key 52 is depressed the number displayed in the lower left part of display 36 will increment by one until the display reads the maximum number of pre-programmed channels in the instrument at which time the display will revert back to the number one.

The TEMP key 58 is depressed when it is desired to read the temperature of the sample being inspected, the temperature being displayed on the upper portion of display 36, and the READ key 60 is depressed when it is desired to read the result of the measurement and/or calculation provided by the instrument depending upon which of the modes has been selected.

FIG. 3 is a schematic diagram of the optical system in the refractometer of the present invention. The optical system includes photosensitive means 70 having a relatively narrow dynamic range for providing an output signal as a function of the amount and location of light incident thereon. The photosensitive means 70 is of the photoelectric type for providing output signals having a characteristic determined by the manner in which light is incident thereon. In particular, the photoelectric means 70 comprises a linear scanned array including a plurality of photoelectric elements, each element providing an output pulse during a scan of the array, and the amplitude of each pulse being determined by the amount of illumination of the corresponding element by incident light. The linear scanned array 70 will be described in further detail presently.

The optical system further includes optical means for directing light onto the photosensitive means 70, the amount and location of light incident on the photosensitive means 70 being determined by the index of refraction of the light transmitting substance placed in operative association with the optical means. The optical means functions to direct light onto the linear scanned array 70, the particular photoelectric elements of array 70 which are illuminated by the light being determined by the index of refraction of the light transmitting substance. As shown in FIG. 3, the optical means includes a light source 72 and a prism 74 for receiving light along an optical path from source 72 and having a surface to receive substances being examined for directing light onto the photoelectric means 70 in a manner determined by the index of refraction of a light transmitting substance in operative contact with the prism surface. In particular, prism 74 includes a top surface 76 as viewed in FIG. 3 for receiving substances to be measured, a bottom surface 78 parallel to surface 76 through which light enters and exits, and a pair of side surfaces 80,82 which define acute included angles with surface 78 and which are internally reflective. Prism 74 is supported in the refractometer in a manner which will be described.

Light source 72 is located and positioned to direct light to prism 74 and can be in the form of a tungsten halogen lamp. In particular, light travels from source 72 along an optical path to prism 74 which path includes a first portion 84 between source 72 and a planar reflecting mirror 86 which then directs light along a second portion 88 of the optical path for entry into the body of prism 74. In accordance with the present invention, there is provided interference filter means 90 having a relatively narrow bandwidth and located along the otpical path between source 72 and prism 74. In particular, the interference filter 90 is located in portion 84 of the optical path and transmits light which is essentially monochromatic. Since the index of refraction for a given liquid will change as a function of the wavelength of light, the provision of interference filter 90 prevents or minimizes any effect of changing wavelength of light from source 72 on the measured refractive index of liquid placed on prism 74. There is also provided a first lens 96 between source 72 and filter 90 for providing substantially parallel rays of light into the filter 90. Lens 96 is a planoconvex lens with the planar surface facing source 72, the convex surface facing filter 90, and located in close proximity to filter 90. There is also provided a second lens 100 between filter 90 and prism 74 for concentrating the output light from filter 90. Lens 100 is a planoconvex lens with the planar surface facing mirror 86, the convex portion facing filter 90, and located in close proximity to filter 90.

In the system of FIG. 3 there is also provided a diffuser 106 located in the portion 84 of the optical path near lamp 72. Diffuser 106 functions to scatter light from lamp 72 so that the light travelling from diffuser 106 toward lens 96 is in effect smoothed out with no phase and no angle. As a result, the light travelling along portion 84 of the optical path is independent of the placement of lamp 72.

Light travelling along portion 88 of the optical path enters prism 74 through the surface 78 and is internally reflected by surface 80 and travels along a path 108 toward prism surface 76. Light refracted by liquid on surface 76 travels within prism 74 along a path 110 is internally reflected by prism surface 82 and exits from prism surface 78 along a portion 112 of another optical path. A reflecting mirror 114 is located along this optical path between prism 74 and the linear scanned array 70. Light travelling along path portion 112 is reflected by mirror 114 along a second portion 118 toward the array 70. A lens 120 is located along portion 112 of the optical path between prism 74 and mirror 114 and is located near the prism surface 78. Lens 120 is of the objective type with the surface of greater curvature facing mirror 114 and the opposite surface facing prism 74. Lens 120 serves to compensate for optical variations in the prism 74.

By way of example, in an illustrative refractometer, prism 74 is of LAF 22 782371 glass, grade A, with optical properties $N_D$—1.78161, $V_D$—37.09 and bubbles—0.1 maximum. Surface 78 is 46.0 mm in length, the distance between surfaces 76 and 78 is 26.0 mm, the prism thickness is 18.0 mm and surfaces 80 and 82 each define an angle of 61° with surface 78. The point of intersection of each path 88 and 112 with surface 78 is 16.086 mm from the mid-point of surface 78 between sides 80 and 82. The objective lens 120 is of Schott SK16 glass, Grade B, with optical properties $N_D$—1.62032, $V_D$—60.3 and bubbles—0.10 mm$^2$/100 cm$^3$. The lens has a diameter of 19.00 mm, thickness of 4.601 mm, radii of curvature of 41.471 mm for the surface facing mm 114 and 191.823 for the surface facing prism 74 and focal lengths of F.F.L—80.726 mm. E.F.L. 84.307 mm and B.F.L—85.081 mm. Mirrors 86 and 114 are of type 3641-656 glass about ⅛ inch thick and of polished plate silvering quality. The optical path 118 between mirror 114 and array 70 has a length of 57.57 mm when the path is perpendicular to array 70 in which case it defines an angle of 40.9 degrees with the surface of mirror 114. Array 70 is perpendicular prism surface 78. The portion of the path 112 between mirror 114 and the surface of lens 120 is 25.0 mm, and the portion between the lens 120 and prism surface 78 is 5.7 mm, the path 112 being disposed at an angle of 8.18 degrees with a lens perpendicular to surface 78. Path 88 is disposed at the same 8.18 degree angle with the normal to prism surface 78, and the distance along path 88 from surface 78 to mirror 86 is 16.3 mm. The portion of path 84 between mirror 86 and lens 100 is 25.6 mm in length and defines an angle of 40.9 degrees with the surface of mirror 86.

The monochromatic filter 90 has a diameter of 25.4 mm, thickness of 4.0 mm. central wavelength of 5890 Å, half bandwidth of 100 Å, minimum transmission of 60%, blocks. X-rays to infrared in the spectrum, and is commercially available from Corion Corp., Holliston, Mass. Each condenser lens 96,100 is of type 523586 glass grade C with optical properties $N_D$—1.5230, $V_D$—58.6, bubbles 0.10 mm$^2$/100 cm$^3$, with focal lengths F.F.L. 49.773 mm, E.F.L. 53.614 mm and B.F.L. 53.614 mm and has a diameter of 25.4 mm, thickness of 5.85 mm and radius of curvature of 28.04 mm. Diffuser 106 is of type M99-04-010 glass having a diameter of 20.0 and a thickness of 1.50 mm. The distance between diffuser 106 and lens 96 along path 84 is 42.0 mm.

In the foregoing illustrative arrangement, the range of refractive indices covered is 1.3330 to 1.5053 which corresponds to 0 to 85 Brix. The useful length of array 70 is 955 cells out of a total of 1024 cells, and the 955 cells have a physical length of 23.875 mm. Cell number 30 of the array corresponds to 0 Brix and cell 985 corresponds to 85 Brix.

As will be described in detail presently, array 70 includes a large number of photoelectric elements spaced along a linear path. In the arrangement shown in FIG. 3, that path is in a vertical direction along the surface of the array facing toward the mirror 114. In the arrangement shown, the portion of the array below the beam along path 118 is dark and the portion of the array above path 118 is light. In other words, all of the array elements along the portion above path 118 are illuminated by light from the optical system. Thus, the shadow line is the transition between the dark and light regions of the array as described.

Figure 4:
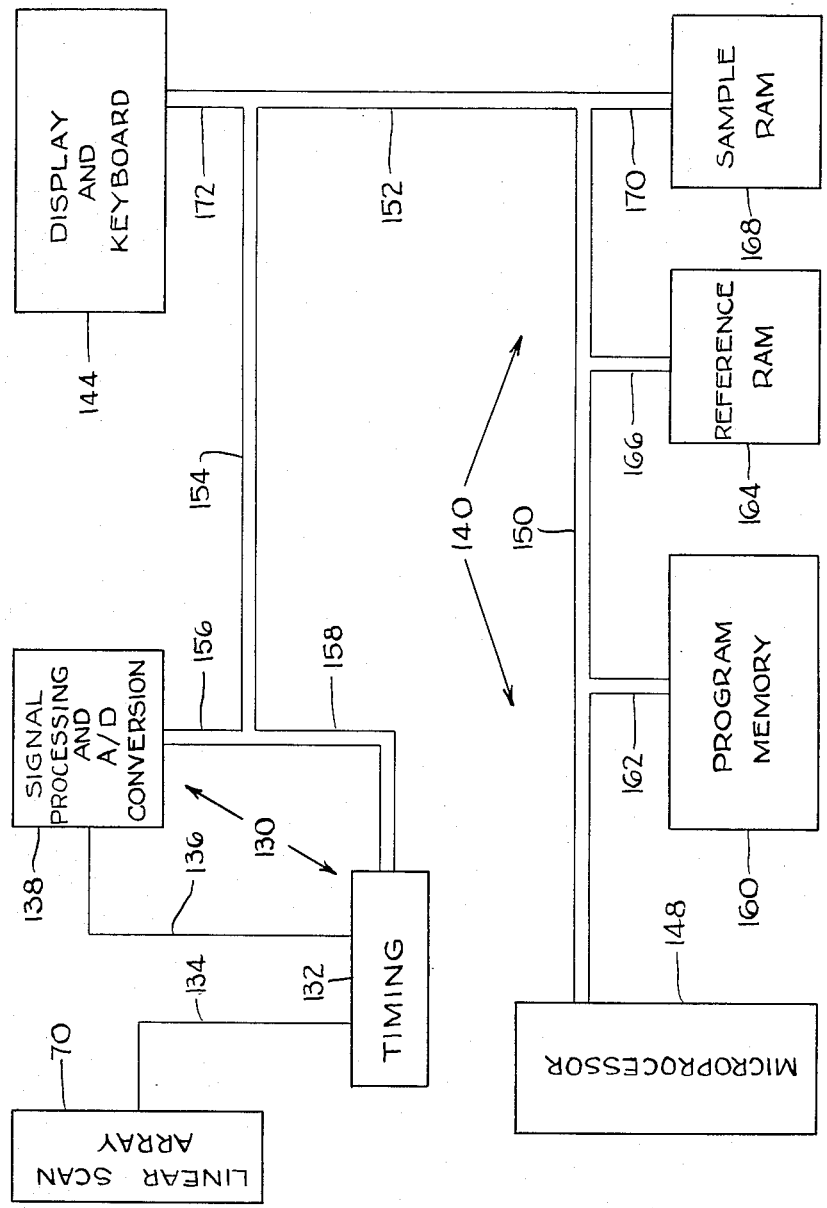
FIG. 4 is a system block diagram of the digital processing circuit and associated apparatus in the automatic refractometer of FIG. 1.

FIG. 4 is a block diagram of the digital processing circuit and associated apparatus of the refractometer of the present invention. The circuit includes means generally designated 130 for converting the signals from the linear scanned array 70 into digital signals containing information as to the amplitudes of those signals from the array. In particular, array 70 is connected under control of the circuit timing portion 132 and through paths 134,136 to a portion 138 of the circuit for signal processing and analog-to-digital conversion. In accordance with the present invention as will be described in further detail presently, portion 138 includes peak detector circuit means operatively connected to the array 70 for detecting the peak amplitudes of signals obtained from the array during scanning thereof, and analog-to-digital converter means operatively connected to the peak detector circuit means for providing digital signals containing information as to peak amplitudes of the array signals.

The system of FIG. 4 further comprises digital processing circuit means generally designated 140 for storing respective digital signals from reference and sample substances placed in operative association with the optical means previously described and for computing the index of refraction of the sample substance by means of a comparison of stored reference and sample signal information. The system further includes means for providing a readout of the result computed by the digital processing circuit means. There is also provided means for commanding various modes of operation of the system and for selecting various measuring and calculating modes. The readout means and selection and control means are generally designated 144 in FIG. 4 and indicated display and keyboard. In particular, the digitial processing circuit means of FIG. 4 includes microprocessor means generally designated 148 which is connected to a main system bus having portions 150, 152 and 154. Bus portion 154 is connected to the signal processing and analog to digital conversion portion 138 of the circuit through a branch bus 156 and through another branch bus 158 to the timing portion 132 of the circuit. The digital processing circuit means further comprises a program memory generally designated 160 and connected through a branch bus 162 to system bus portion 150, a reference memory 164 connected through a branch bus 166 to bus 150, and a sample memory 168 connected through a branch bus 170 to the bus 150. The display and keyboard 144 is connected through a branch bus 172 to the bus portion 152.

Figure 5:
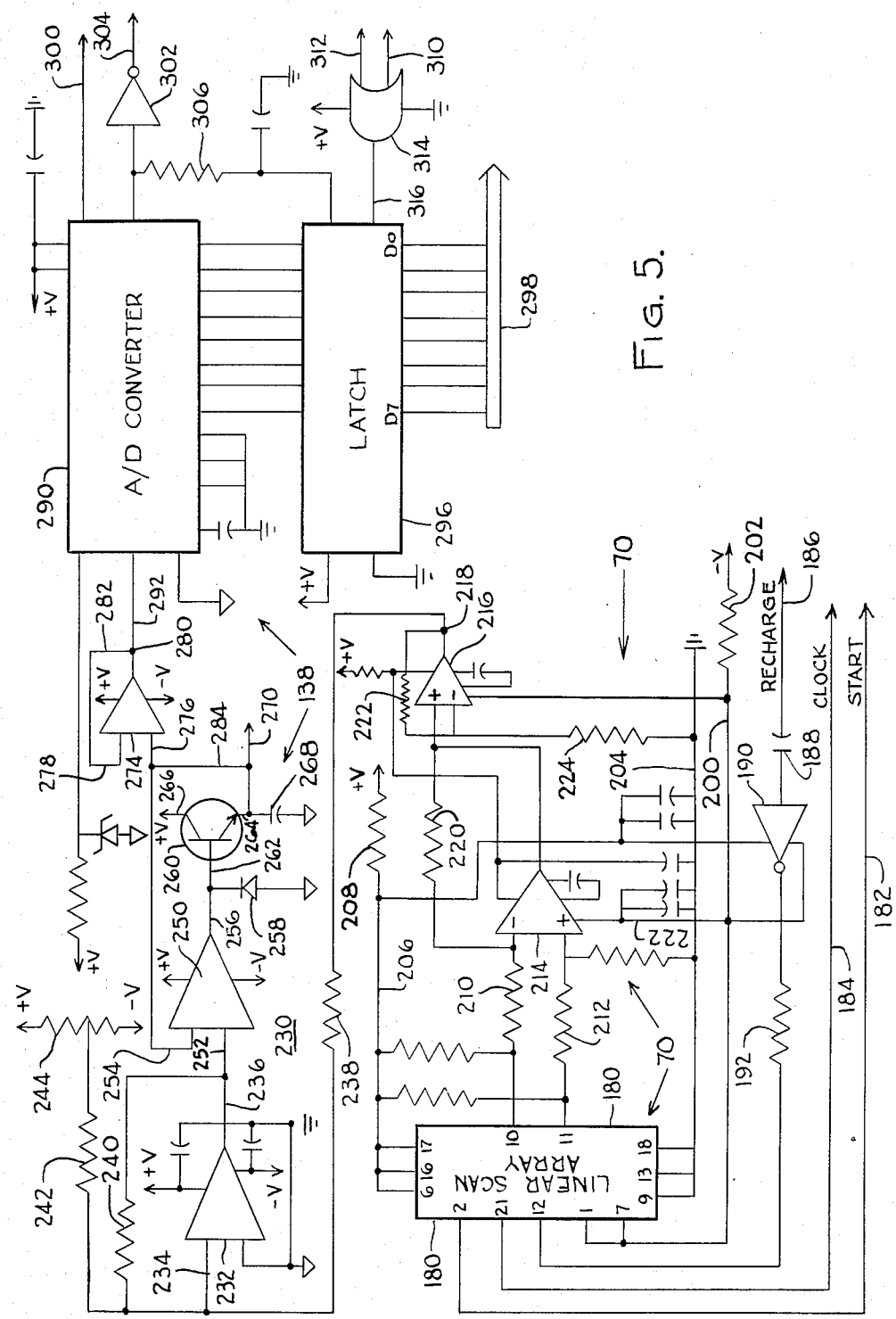
FIG. 5 is a schematic circuit diagram of the linear scanned array and signal processing and analog-to-digital conversion portion of the system of FIG. 4.

FIG. 5 shows in detail the linear scanned array 70 and signal processing and analog-to-digital conversion portion 138 of the system of FIG. 4. Array 70 includes the array device 180 itself together with associated circuitry. The array device 180, briefly, is a monolithic, self-scanning linear photodiode array consisting of a row of silicon photodiodes, each with an associated storage capacitor on which to integrate photocurrent and a multiplex switch for periodic readout by means of an integrated shift register scanning circuit. During each scan of the array, the charge on each photodiode is removed by photocurrent which is the product of diode sensitivity and light intensity or irradiance. By way of example, in an illustrative apparatus, an array device 180 is a G Series solid state line scanner model RL1024G available commercially from EG&G Reticon of Sunnyvale, Calif. This exemplary array includes 1024 photodiode elements, and the device 180 shown in FIG. 5 is provided with the pin numbers corresponding to this exemplary array. For more detailed information with respect to the structure and operation of device 180, reference may be made to the four page product description no. 18220 from EG&G Reticon entitled "G Series Solid State Line Scanners 128, 256, 512 and 1024 Elements", the disclosure of which is hereby incorporated by reference.

Turning now to the circuitry associated with array device 180, start pulses and clock pulses on lines 182,184, respectively, are applied to respective pins of array 180 and are obtained from the timing portion 132 of the system which will be described in detail presently. Recharge signals present on line 186 are coupled through a capacitor 188, inverter 190 and resistor 192 to the appropriate pins of device 180. Negative bias or operating voltage is provided to device 180 by line 200 which is connected through a resistor 202 to an appropriate supply. Electrical ground is connected through line 204 to other pins of array 180. Positive bias or operating voltage is provided to device 180 by a line 206 which is connected through resistor 208 to a supply. Output signals obtained from the pins 10 and 11 of device 180 are applied through resistors 210 and 212, respectively, to the negative and positive input terminals, respectively, of a first amplifier 214, the output of which is connected to the positive input terminal of a second amplifier 216 having an output 218. Feedback resistors 220 and 222 are connected in the circuits of amplifiers 214 and 216, respectively, as shown in FIG. 5. The negative input terminal of amplifier 216 is connected through a resistor 224 to reference line 204. Positive and negative operating voltages are applied to the amplifiers 214 and 216 as shown in FIG. 5.

The remainder of the circuit illustrated in FIG. 5 comprises the signal processing and analog-to-digital conversion portion 139 which includes a peak detector circuit generally designated 230 for detecting the peak amplitudes of the signals obtained from array 70 during scanning thereof. The peak detector 230 includes an input amplifier 232 having an input 234 and an output 236. Amplified output signals from array device 180 present on line 218 are applied through resistor 238 to the amplifier input terminal 234. A feedback resistor 240 is connected between the amplifier output 238 and input terminal 234. The junction of input terminal 234 and feedback resistor 240 also is connected through a resistor 242 to the wiper arm of a potentiometer 244. The other input terminal of amplifier 232 is connected to the circuit ground or reference.

The peak detector circuit further includes an amplifier 250 having a pair of inputs 252 and 254 and an output 256. Amplifier input 252 is connected to the output 236 of amplifier 232. The cathode of a clamping diode 258 is connected to the amplifier output 256 and the anode is connected to an internal reference or ground.

The peak detector further comprises a transistor 260 having base, emitter and collector terminals 262 and 264 and 266, respectively. Base terminal 262 is connected to output 256 of amplifier 250. Emitter terminal 264 is connected through a capacitor to the internal ground or reference and is connected also through a line 270 to the system timing portion 132 in a manner which will be described.

The peak detector further comprises an amplifier 274 connected as a voltage follower and having a pair of inputs 276 and 278 and an output 280 which is connected by a line 282 back to the amplifier input 278. The emitter terminal 264 of transistor 260 is connected by line 284 to the amplifier input 276 which input also is connected to the input 254 of amplifier 250 as shown in FIG. 5.

The circuit of FIG. 5 further comprises an analog-to-digital converter 290 having an output 292 connected to the output 280 of the peak detector circuit. Converter 290 converts the input signals on line 292 to an eight bit digital output present on the eight output lines shown in FIG. 5 which, in turn, are connected to inputs of a latch circuit 296 to interface with a system bus portion 298. The eight bits of the latch output are designated D0–D7 and provide the digitized value of each of the 1024 array output pulses provided during each scan thereof. The provision of latch 296 increases the speed by which this digital information can be placed on and taken off the system bus. Timing pulses for operating converter 290 are present on a line 300 connected to the system timing portion 132 in a manner which will be described. Snychronizing signals from converter 290 are applied through inverter 302 and a line 304 to other circuit components in a manner which will be described, and the same signals are connected through resistor 306 to latch 296. The latch 296 also is connected to other portions of the system by means of lines 310 and 312 connected to corresponding inputs of an Or gate 314, the output of which is connected by line 316 to an appropriate terminal of latch 296.

By way of example, in an illustrative circuit, amplifiers 214 216 and 232 are type CA 3100, amplifiers 250 and 274 are type LF356, converter 290 is type ADC 0820 and latch 296 is type 74LS 373.

Figure 6:
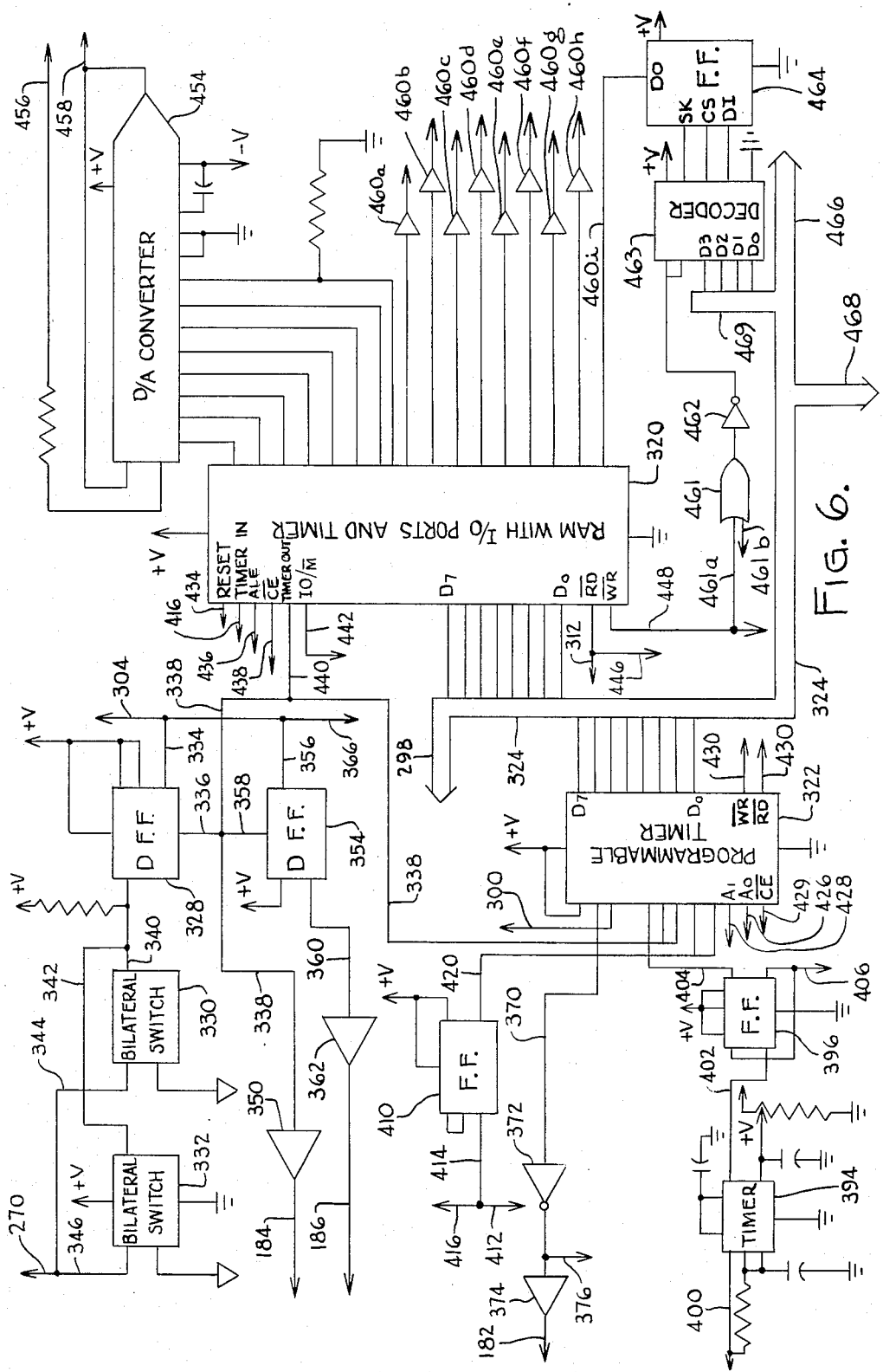
FIG. 6 is a schematic circuit diagram of the timing portion of the system of FIG. 4.

FIG. 6 shows in further detail the timing portion 132 of the system of FIG. 4 which includes two principal components. A first is a programmable part 320 comprising a 256×8 RAM, a programmable 14 bit timer and 22 programmable I/O pins. The other part is a programmable timer 322 comprising three such timers which are used for the linear scanned array 70, analog-to-digital timing, and also with temperature measuring circuitry which will be described. Both components 320 and 322 are connected to a system bus portion 324 which, in turn, is connected to the bus portion 298 shown in FIG. 5. The eight bit connections to the bus 298 for each component 320 and 322 are identified D0-D7.

The circuit of FIG. 6 also includes a reset circuit for the peak detector of FIG. 5 including the combination of a D flip-flop 328 and a pair of CMOS bilateral switches designated 330 and 332. The switches 330 and 332 advantageously have a low leakage current during the off state. Flip-flop 328 has an input 334 connected to line 304 from the analog-to-digital converter 290 in the circuit of FIG. 5. Flip-flop 328 has a clock input 336 connected to a line 338 containing timing pulses which are obtained from the part 320 in a manner which will be described. The output of flip flop 328 is connected by line 340 to the input switch 330 and by line 342 to the input of switch 332. The outputs of switches 330 and 332 are connected by lines 344 and 346, respectively, to line 270 leading to the peak detector circuit of FIG. 5.

The circuit of FIG. 6 also includes interfacing portions for driving the array 70. The previously mentioned timing signals on line 338 obtained from part 320 are connected to the input of an amplifier 350, the output of which is connected to the clock pulse line 184 in the circuit of FIG. 5. There is also provided a D flip-flop 354 having an input 356 connected to line 304 from the analog-to-digital converter 290 of FIG. 5, having a clock input 358 connected to line 338 for receiving timing pulses, and having an output 360 connected to the input of an amplifier 362, the output of which is connected to the recharge signal line 186 in the circuit of FIG. 5. Signals applied to the input 256 of flip flop 354 also are applied by line 366 to an RST interrupt pin on the system microprocessor in a manner which will be described.

In addition, start pulses for the array 70 are obtained from an output of timer 322 to line 370 which is coupled through an inverter 372 to the input of an amplifier 374, the output of which is connected to the start pulse line 182 in the circuit of FIG. 5. The output of inverter 372 also is connected by a line 376 to an RST interrupt pin on the system microprocessor in a manner which will be described.

The circuit of FIG. 6 further provides a prism temperature measuring function. In particular the prism temperature measuring function is provided by the combination of a solid state timer 394 and a flip-flop 396. The analog voltage output of a thermistor associated with the refractometer prism is connected by a line 400 to an output of timer 394 which converts the analog signal to pulses of proportional frequency on line 402 which is connected to the input of flip flop 396. Timing pulses from an output of flip flop 396 are applied by line 404 to input of timer 322. Flip-flop 396 also is connected by a line 406 to an RST interrupt terminal on the system microprocessor as will be described. The circuit of FIG. 6 also includes a flip-flop 410 connected as a divide by two flip-flop to serve as an interface to the timer 322. In the system shown, the microprocessor has a clock output of 3 Mhz and timer 322 has a maximum frequency input of 2 Mhz. Therefore, flip-flop 410 divides the clock signal from the microprocessor down to 1.5 Mhz for use by the timer 322. In particular, the clock output from the system microprocessor on line 412 is connected to the input 414 of flip-flop 410. These clock pulses from the microprocessor also are connected by line 416 to the timer input of component 320. The frequency divided output from flip-flop 410 is connected by line 420 to inputs of timer 322.

Timer 322 supplies timing pulses to the analog-to-digital converter 290 in FIG. 5. To this end, an output of timer 322 is connected to line 300 leading to converter 290 as shown in FIG. 5. Timer 322 also supplies timing pulses and address information to circuitry associated with the display as will be described. Line 429 connects an input of timer 322 to an address decoder which will be described, and the two address outputs A0,A1 of timer 322 are connected by lines 426 and 428, respectively, to a bus associated with that decoder. Lines 430 and 432 from timer 322 also are connected to the display interface in a manner which will be described.

Turning now to the component 320, the reset terminal thereof is connected by line 434 to a reset terminal of the system microprocessor. Line 436 is connected to an output circuit of the system microprocessor, and line 438 is connected to the previously described address decoder associated with the display interface. Line 440 connects a timing pulse output to line 338 previously described. Line 442 is connected to a bus portion associated with the previously mentioned address decoder. Another terminal of component 320 is connected to line 312 leading to the OR gate 314 in FIG. 5 associated with latch 296. This same terminal is connected by line 446 to the previously mentioned display interface along with line 448 connected to another terminal of component 320.

The circuit of FIG. 6 further includes an arrangement for controlling the voltage to the illuminating lamp of the refractometer, i.e. light source 72 in FIG. 3, in a manner which will be described in further detail presently. Briefly, digital information for changing lamp voltage is present on the eight output lines leading from part 320 which are connected to appropriate inputs of a digital-to-analog converter 454. Analog output voltage applied to the lamp control is present on line 456 and an adjustment control voltage is present on line 458.

Part 320 also provides an interface to the system printer, and eight output lines containing buffers 460a-460h are connected to the printer. Another output line 460i is connected to a hand-shaking circuit including Or gate 461 having one input 461a connected to line 448 and another input 461b connected to an address decoder 560 in a portion of the system shown in FIG. 7 and which will be described. The output of gate 461 is connected through an inverter 462 to a decoder 463. Outputs of decoder 463, in turn, are connected to a flip-flop 464 which is connected also to line 460i from component 320. The bus portion 324 shown in FIG. 6 is connected by branches designated 466 and 468 to other portions of the system bus in a manner which will be described, and it is connected by a branch 469 to inputs of decoder 463 as shown in FIG. 6.

By way of example, in an illustrative circuit, components 320 and 322 are commercially available from Intel under model nos. 8156 and 8253, respectively, switches 330 and 332 are CMOS type CD4016, flip-flops 328, 354, 396 and 410 are type 74LS74, flip-flop 380 is type 74LS123, timer 394 is type LM 555 converter 454 is type DAC 0800, decoder 463 is type 74LS375 and flip-flop 464 is type NMC9306NE.

Figure 7:
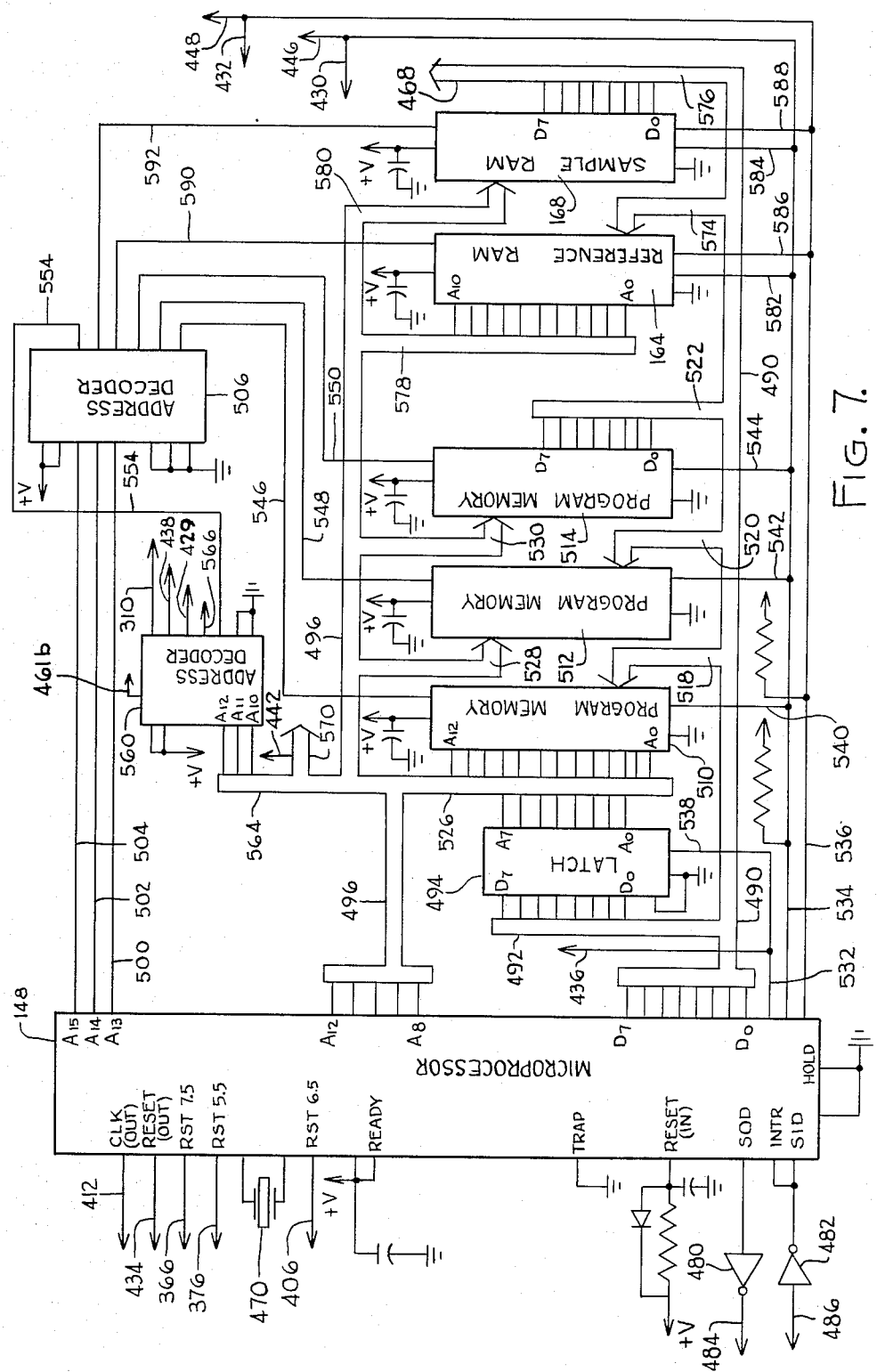
FIG. 7 is a schematic circuit diagram of the microprocessor, program memory, reference and sample RAMs and associated circuitry of the system of FIG. 4.

FIG. 7 shows in detail the microprocessor 148, program memory 160, reference RAM 164 and sample RAM 168 and associated circuitry in the system of FIG. 4. Turning first to microprocessor 148, the output clock pulses are applied by line 412 to flip-flop 410 in the circuit of FIG. 6 and by line 416 to the component 320 in the circuit of FIG. 6 as previously described. Reset pulses from micrprocessor 148 are applied by line 434 to the reset input of component 320 in FIG. 6. The RST 7.5 interrupt of the microprocessor is connected by line 366 to the circuit of FIG. 6 and the RST 5.5 interrupt is connected by line 376 to the input of amplifier 374 in FIG. 6. The standard clock frequency, in the present instant 6 Mhz, is provided by a frequency oscillator or source 470 connected to the microporcessor. The RST 6.5 interrupt is connected by line 406 to flip-flop 396 in the circuit of FIG. 6. The terminals designated SOD and SID are connected through inverters 480 and 482 and lines 484 and 486, respectively, to hardware for providing a serial communication function as will be described.

The ports of microprocessor 148 associated with data bits D0–D7 are connected to a bus portion 490 having a branch 492 connected to inputs designated D0–D7 of latch 494. The microprocessor ports associated with a group of address bits A8–A12 is connected to a bus portion 496. Three other address bits A13, A14, and A15 are connected by lines 500, 502, and 504, respectively, to an address decoder 506.

The program memory 160 of the system of FIG. 4 comprises the three PROMS designated 510, 512 and 514 in FIG. 7. Bus portion 490 has branches 518, 520 and 522 connecting the data bits D0–D7 to PROMS 510, 512 and 514, respectively. Latch 494 provides an interface between the data bits D0–D7 and the address bits A0–A7 to a branch 526 to bus portion 496. The branches 526, 528 and 530 of bus portion 496 connect the address bits A0–A12 to PROMS 510, 512 and 514, respectively.

Timing and synchronizing signals are present on lines 532, 534 and 536 leading from microprocessor 148. Line 532 is connected by line 436 to component 320 in the circuit of FIG. 6, and is connected by line 538 to latch 494. The signals on line 534 are connected by lines 540, 542 and 544 to PROMS 510, 512 and 514, respectively.

Address decoder 506 is connected by lines 546, 548 and 550 to PROMS 510, 512 and 514, respectively. Decoder 506 also is connected by line 554 to another address decoder 560 in the circuit of FIG. 7. A branch 564 of bus portion 496 connects address bits A10, A11 and A12 to address decoder 560. Decoder 560 is connected by line 319 to OR gate 314 associated with latch 296 in the circuit of FIG. 5. Decoder 560 also is connected by line 438 to component 320 and by line 429 to timer 322 in the circuit of FIG. 6. A line 566 connects decoder 560 to display interface circuitry in which will be described in detail presently. Bus portion 496 is connected by a branch 570 leading from branch 564 to another bus portion in the system in a manner which will be described. Line 442 from component 320 in FIG. 6 is connected to branch 570 as shown in FIG. 7.

The circuit of FIG. 7 further includes reference RAM 164 and sample RAM 168. Bus portion 490 has branches 574 and 576 connecting the data bits D0–D7 to RAMS 164 and 168, respectively. Similarly, bus portion 496 has branches 578 and 580 connecting address bits A0–A10 to RAMS 164 and 168, respectively. Signals from microprocessor 148 on line 534 are connected to RAMS 164 and 168 by lines 582 and 584, respectively. Similarly, signals on line 536 are connected to RAMS 164 and 168 by lines 586 and 588, respectively. Address decoder 506 is connected by lines 590 and 592 to RAMS 164 and 168, respectively. Bus portion 490, after connection to sample RAM 168, leads into branch 468 in the arrangement of FIG. 6. Also, line 534 from microprocessor 148 is connected to timer 322 by line 430 and to component 320 by line 446 as shown in FIG. 6. Similarly, line 536 from the microprocessor is connected to timer 322 by line 432 and to component 320 by line 448.

By way of example, in an illustrative circuit, microprocessor 148 is Intel model no. 8085, each PROM 510, 512 and 514 is Intel model no. 2764, each RAM 164 and 168 is Hitachi model no. HM 6116, flip flop 474 is type 74 LS123, latch 494 is type 74 LS373, and each decoder 506 and 560 is type 74LS138.

Figure 8:
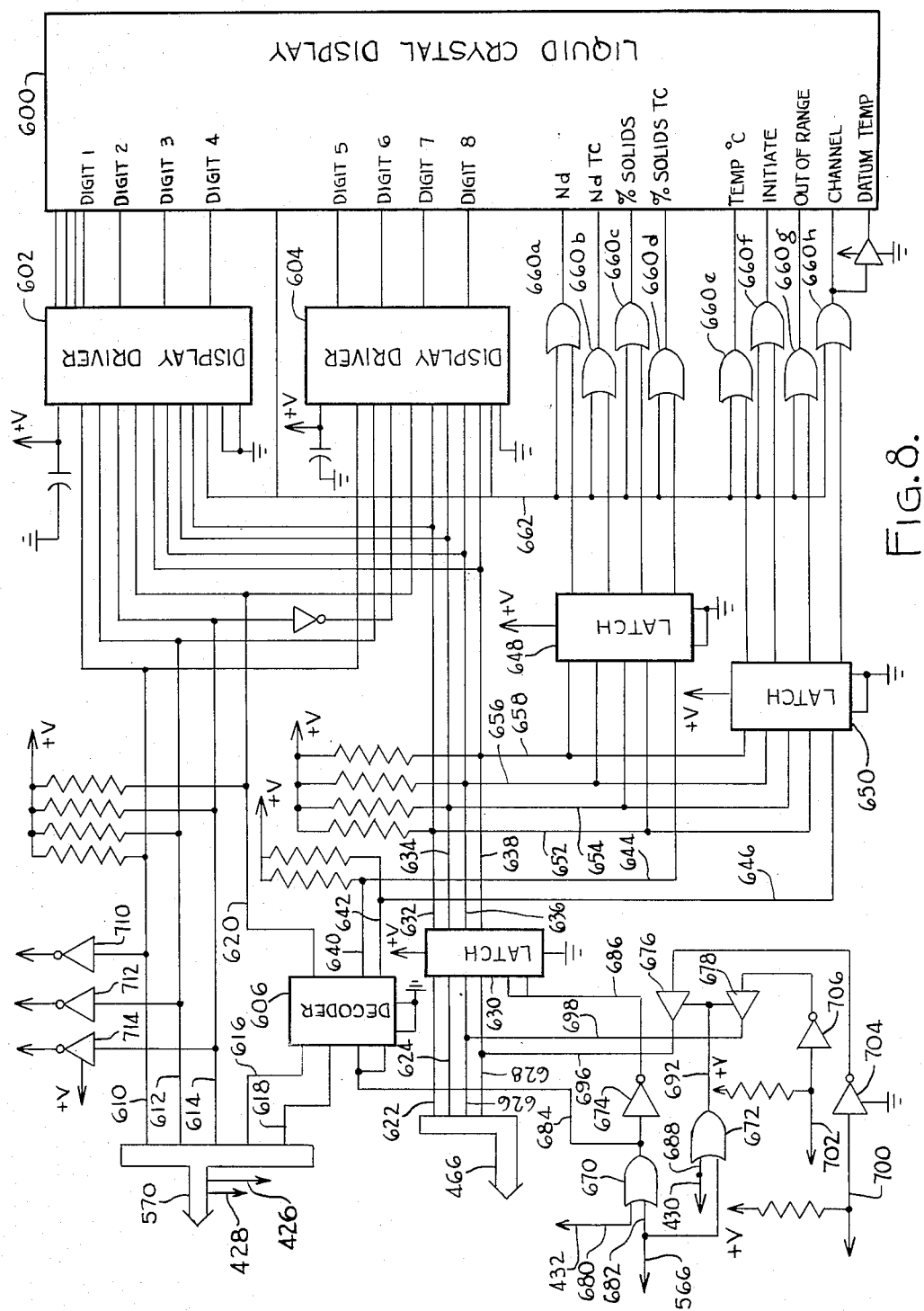
FIG. 8 is a schematic circuit diagram of the display and keyboard arrangement of the system of FIG. 4.

FIG. 8 shows in further detail the display and keyboard arrangement 144 in the system of FIG. 4. The display comprises a liquid crystal display component 600 and provides six large numbers, i.e. the digits designated 1–6 in FIG. 8 and two small numbers, i.e. the digits designated 7 and 8. In addition, display 600 includes the nine legends as indicated in FIG. 8. The arrangement of FIG. 8 includes selection circuitry including the bus branch 570 from the circuit of FIG. 7, a pair of display drivers designated 602 and 604 associated with display 600, and a decoder 606. Bus branch 570 also is connected by lines 426, 428 to timer 322 in the circuit of FIG. 6 as shown. The various digits in display 600 are connected to corresponding outputs of the drivers 602, 604 and each single line represents a plurality of conductors for each digit segment, for example seven such conductors. By way of example, in an illustrative system, a liquid crystal display 600 found to perform satisfactorily is available commercially from Hamlin. The particular digit in the display is selected by appropriate address information contained in bits from bus 570 present on lines 610, 612, 614 and 616 and 618. These may be referred to as address bits A0–A4 respectively. Lines 610, 612 and 614 are connected to inputs of both drivers 602 and 604 as shown in FIG. 8. Lines 616 and 618 are connected to inputs of decoder 606, and an output is connected by line 620 to inputs of drivers 602, 604 as shown.

Data to be displayed is provided on bus portion 466 which is connected by lines 622, 624, 626 and 628 to a latch 630. The corresponding data outputs of latch 630 are connected by lines 632, 634 and 636 and 638 to the display drivers 602 and 604 as shown. The signals on these lines may be referred to as the data bits D0, D1, D2 and D3, respectively. The operation of decoder 606 along with the internal decoding provided in the display drivers 602 and 604 will turn on the appropriate segments of display 600.

The legends on display 600 are selected in the following manner. Address information for selecting the legends is obtained from the keyboard in a manner which will be described and provided to the decoder 606. This information, in turn, is present on outputs 640, 642 of decoder 606 which, in turn, are connected by lines 644 and 646 to corresponding latches 648 and 650. The data lines 632, 634 and 636 and 638 are connected by lines 652, 654, 656 and 658, respectively, to inputs of latches 648 and 650. Each latch 648 and 650 has four outputs, each in turn being connected to one input of a corresponding plurality of gates 660a-660h. The other inputs of the gates are connected by line 662 to the display 600 and to drivers 602,604. The gates 660 and their connection to the drivers and display provide the a.c. square wave drive for the display. The outputs of the gates 660, in turn, are connected to correspoding segments providing the legends illustrated in FIG. 8. For selection of the legends, address information is provided on lines 644 and 646 from decoder 606 and with the appropriate bits on the data lines 652,654,656 and 658 this will set the bits in either latch 648 or 650.

The arrangement of FIG. 8 also includes display interface circuitry. In particular, this is provided by a pair of gates 670 and 672, an inverter 674, the latch 630 and a pair of amplifiers 676 and 678. In particular, referring to gate 670 it has an input 680 connected to line 432 in the circuit of FIGS. 6 and 7. It has another input 682 connected to line 566 leading from address decoder 560 in the circuit of FIG. 7. The output of gate 670 is connected to inverter 674 and is connected by a line 684 to decoder 606. The output of inverter 674 is connected by line 686 to latch 630. Turning now to gate 672, it has one input 688 connected to line 430 in the circuits of FIGS. 6 and 7, and it has another input connected by line 690 to input 682 of gate 670. The output of gate 672 is connected by a line 692 to the pair of amplifiers 676 and 678. The outputs of amplifiers 676 and 678, in turn, are connected by lines 696 and 698, respectively, to data lines 628 and 626, respectively.

A pair of keyboard return lines 700 and 702 are connected through inverters 704 and 706, respectively, to the inputs of amplifiers 676 and 678, respectively. The return lines 700, 702 will be active when a key press occurs and the right column is selected. Address lines 610, 612, and 614 are connected through inverters 710, 712 and 714, respectively, to corresponding lines which stroke the keyboard in a column select arrangement.

The refractometer of the present invention operates in the following manner. When power is first turned on, all keys 52-60 are disabled, and the INITIATE key 50 is depressed to enable the instrument. The light level at array 70 is measured and the voltage for lamp 72 is adjusted in a manner which will be described to obtain the optimum light level at the array 70. Thereafter a reference scan of array 70 is made and information therefrom stored in the instrument memory. If all operations fall within predetermined limits, ascertained by the system program which will be described, the display provides a message such as the word "Hello" and the keyboard is able to accept all other valid commands.

Next the MODE key 54 is pressed to obtain one of the various measuring modes of the instrument, by successively pressing the key to cycle through the various modes until the desired one is displayed. In particular, Nd is refractive index according to the industry standard of the sodium D line of 589.3 nanometers wavelength and NdTc is refractive index temperature compensated to 20° C. The mode % SOLIDS involves computation from the measured refractive index and the value is dependent upon the particular channel selected by key 52. The mode % SOLIDS TC provides the value corrected to the temperature as stored to the datum value in the channel. The DATUM TEMP mode shows the temperature value in the memory on which the scale is referenced to. The TEMP mode provides a readout of the temperatures of the liquid being measured.

In order to calibrate the instrument for proper readings, cover 40 is lifted and water, preferably distilled, is placed on prism surface 76. The CALIBRATE key 56 then is pressed. The instrument measures the temperature of the water on prism surface 76, determines the computed cross-over of the shadow-line, and stores the result in the instrument memory for use on the reference for all other readings. The manner in which temperature is measured and computed cross-over of the shadow-line is determined will be described in detail presently.

Next, the appropriate scale measurement is selected by pressing CHANNEL key 52. Channel number 1 is implied to be the Brix scale in the illustrated instrument. The scale number will increment until the display reads the maximum number of pre-programmed chambers provided in the instrument whereupon the display will roll over to channel 1.

Then, a substance to be measured is placed on prism surface 76 and READ key is depressed. The measured or calculated value will appear in the upper left portion of display 36, i.e. the value of Nd, NdTC, % SOLIDS or % SOLIDS TC depending upon which mode was selected by key 54. If it is desired to read the temperature of the substance being measured, the TEMP key 58 is depressed and the temperature appears on the display.

The refractometer of the present invention employs linear scanner array 70 to find the cross-over. This cross-over or the critical angle from the refraction consists of a black and white transition. The linear scanned array 70 is in the projected optical path as illustrated in FIG. 3, and due to the precise mechanical dimensions of array 70 the angle change in the optical path due to refractive index is translated to a linear change along array 70. This linear change then is used as a function is polynomials to display the desired computed result.

In particular, as shown in FIG. 3, light from source 72 is scattered such that light travelling along path portion 84 toward lens 96 is smoothed out with no phase and no angle. As previously described, the light transmitted through filter 90 toward mirror 86 is essentially monochromatic so as to prevent or minimize any effect of changing wavelength of light from source 72 on the measured refractive index of liquid placed on prism surface 76. This light is directed by mirror 86 along path 88 into prism 74 as shown in FIG. 3.

The angle between path portion 110 and surface 76 is dependent upon the index of refraction of the substance placed on prism surface 76. This, in turn, influences the angle between path portion 112 and prism surface 82, and, consequently, the angle of incidence of path portion 112 on mirror 114 and the angle of incidence of path portion 118 on array 70. In particular, the ratio of the refractivities of prism 74 and the liquid placed on surface 76 determines the ultimate angle of the light beam exiting from prism 74. Thus, as different liquids having different refractive indices are measured, the foregoing angles will change and the location of path portion 118 will change along array 70 in a vertical direction as viewed in FIG. 3.

As previously described, in the arrangement shown, the portion of array 70 below the beam along path 118 is dark and the portion of the array above path 118 is light so that all the array elements along the portion above path 118 are illuminated and the shadow line, i.e. the transition between the dark and light regions of the array, will be on or adjacent one of the array elements. This location of the shadow line will change as the measured refractive index changes, and this location and changes therein are determined by the system in a manner which will be described. As previously mentioned, in an illustrative system wherein the range of refractive indices covered to 1.330 to 1.5053 corresponding to 0 to 85 Brix, the useful length of array 70 in covering this range is 955 cells out of a total of 1024 cells. The refractometer of the present invention provides an accuracy of ±0.15 Brix. This is accomplished by determining the signal amplitude for each element of array 70 and obtaining information relating to pulse-to-pulse amplitude comparisons and rate of change information to provide absolute value determinations not only cell-to-cell but also in the gray or transition area as will be described.

The digital data processing and electronic portion of the refractometer of the present invention illustrated in FIGS. 4-8 includes, briefly, array 70 and support circuitry therefor, signal processing and analog-to-digital conversion for digitizing the amplitudes of the individual pulses or pixels from array 70, memory to store the resulting amplitudes, a microprocessor to control the overall operation including refractive index determination and precent solides calculation and a means for displaying the results of the selected mode of operation.

Turning first to linear scanned array 70, it consists of a row of silicon photodiodes, each with an associated storage capacitor on which to integrate-photocurrent and a multiplex switch for periodic readout via an integrated shift register scanning circuit. Array 70 operates in the charge storage mode whereby the charge output of each diode, below saturation, is proportional to exposure, i.e. the irradiance or light intensity multiplied by the integration time or the time interval between successive start pulses. The light sensing area of array 70 is long, narrow rectangular region defined by an aperture in an opaque mask, the photodiodes extend across the aperature, and the entire aperature is photosensitive because photocurrent generated by light incident between the photodiodes will be collected by the nearest diode. The multiplex switches of array 70 are sequentially closed for one clock period by the shift register scanning circuit thereby recharging each cell to a level, for example 5 volts, and storing a charge, for example approximately 3 p.c., on its capacitance. The scanning circuit is driven by the clock pulses present on line 184 in the circuit of FIG. 5 with a periodic start pulse introduced via line 182 to initiate each scan. The cell-to-cell sampling rate is the clock frequency, i.e. the frequency of pulses on line 184, and the total time between line scans is the interval between start pulses on line 182. During this line time the charge stored on each photodiode in array 70 is gradually removed by photocurrent. The photocurrent is the product of the diode sensitivity and the light intensity or irradiance. The total charge removed from each cell is the product of the photocurrent and the line time. This charge is replaced by a voltage on the recharge line 186 in FIG. 5 when the diode is sampled and reset once each scan.

The output of array 70 is present on line 218 and consists of a series of pulses or pixels generated during each scan and there being one pixel for each scanned photodiode in array 70. The amplitudes of the pixels are proportional to exposure of incident light on array 70.

These pulses are applied to the peak detector 230 in the circuit of FIG. 5 which plays an important role in achieving the accuracy provided by the refractometer of the present invention. In particular, in order to obtain an accuracy of 0.1 Brix it is necessary to have absolute value information in the grey or transition region associated with the shadow line. In other words, information is needed as to the absolute value or amplitude of each pulse because ultimately there will be needed pulse-to-pulse amplitude comparisons and rate of charge information to get the desired accuracy in the gray or transition region.

The provision of peak detector 230 assures that the amplitude information of each pixel from array 70 is obtained for use by the system. In particular, where the acquisition or conversion time of A/D converter 290 is greater than the pulse width of the individual pixels from array 70, peak detector 230 functions to seize or grab the amplitude information. Each individual pixel from array 70 is amplified by amplifier 232 and applied to input 252 of amplifier 250. Amplifier 250 provides an output when the signal on input 252 is greater than that on input 254, and diode 258 clamps output 256 to a predetermined level, for example 0.7 volts. During the rise of the individual pixel toward its peak amplitude, transistor 260 is turned on to charge capacitor 268. When the peak amplitude is reached and the pulse then begins to fall, capacitor 268 holds a level corresponding to the peak pixel amplitude and as the signal on input 252 falls, the amplifier output 256 goes to zero thereby turning off transistor 260. The level held on capacitor 268 is applied through amplifier 274 to analog-to-digital convertor 290, and this level which corresponds to the pixel peak amplitude is present for a time at least equal to the acquisition or conversion time of converter 290. Thereafter, a discharge path for capacitor 268 is provided along line 270. The foregoing is repeated for each pixel on line 216 from array 70, and each time the level on capacitor 268 may be different depending upon the peak amplitude of each pixel.

Figure 9:
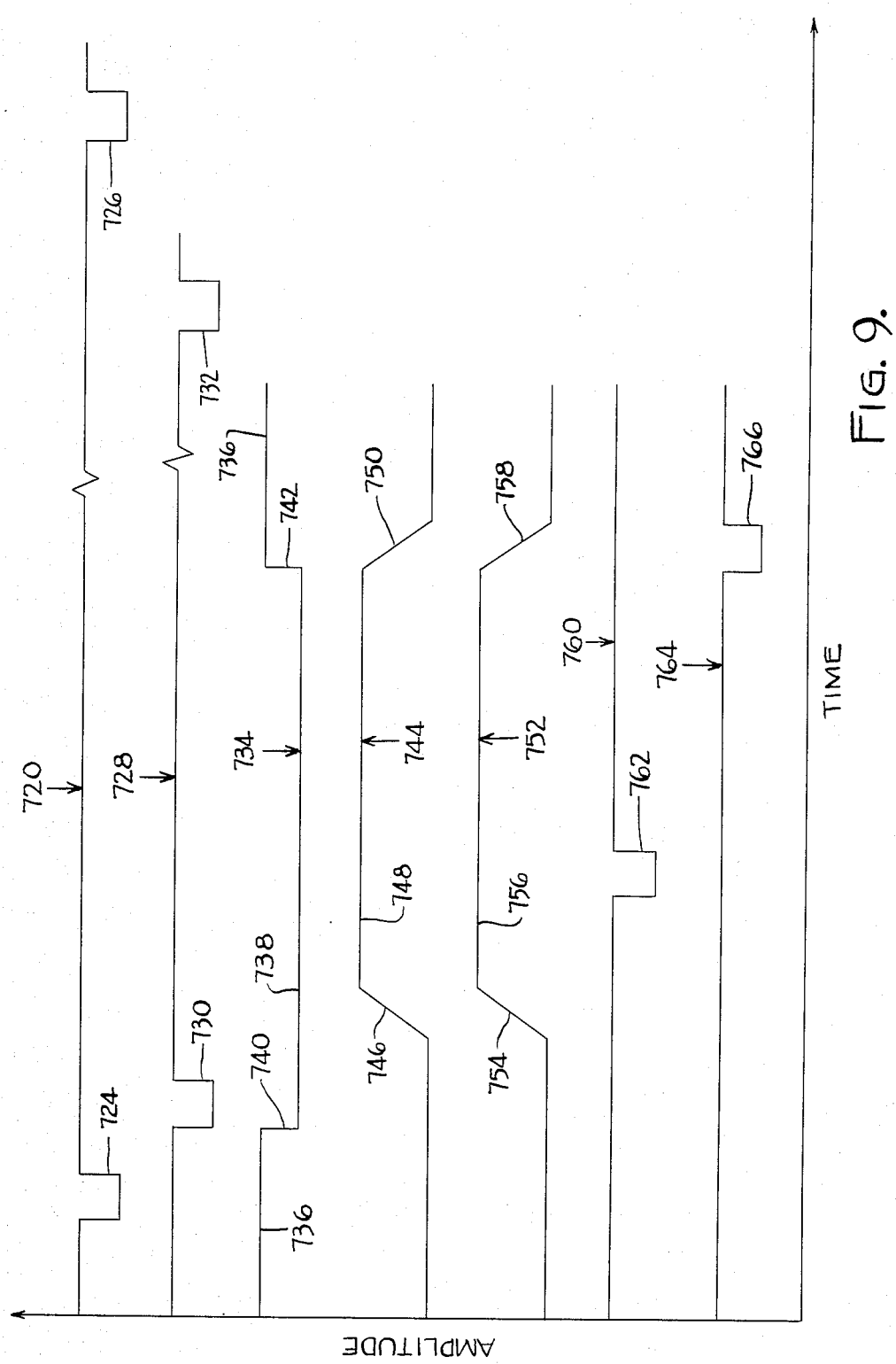
FIG. 9 is a graph including waveforms illustrating operation of the circuit of FIG. 5.

The foregoing is illustrated further by the waveforms shown in the timing diagram of FIG. 9. Waveform 720 shows two successive or adjacent start pulse signals 724 and 726 applied to line 182 in the circuit of FIG. 5. The time between two start pulses such as pulses 724 and 726 in FIG. 9 corresponds to one complete scan of all elements in array 70. By way of example, in an illustrative system wherein array 70 has 1024 elements, the time between two adjacent start pulses, i.e. the time for one scan, is 80 milliseconds. Waveform 728 shows two successive or adjacent clock pulse signals 730 and 732 applied to line 184 in FIG. 5. The time between two array clock pulses such as pulses 730 and 732 in FIG. 9 includes the time for signal processing of a single pixel in peak detector 230 plus the analog-to-digital conversion in converter 290. By way of example, in an illustrative system, the time between two adjacent array clock pulses is 60 micro seconds.

Waveform 734 is the recharge signal present on line 186 in the circuit of FIG. 5. It includes an off level 736 and an on level 738, the latter providing the recharge function for array 70 as previously described. The transition 740 between off and on levels coincides in time with the leading edge of each array clock pulse, for example pulse 730 as shown in FIG. 9. The transition or return 742 from on to off occurs in time prior to the next array clock pulse, for example pulse 732 as shown in FIG. 9.

Waveform 744 represents the signal on input 252 of amplifier 250 and is a pixel from array 70 amplified by amplifiers 214 and 232. It includes a ramp-like leading edge 746, a relatively flat horizontal portion 748 and a trailing edge 750 which begins at a time coinciding with the transition 742 of recharge signal 734. The transition of the recharge signal is utilized to cause drop-off of the signal 744. Waveform 752 represents the signal on output 280 of amplifier 274. It mirrors signal 744 and includes a ramp-like leading edge 754 coinciding in time with leading edge 746 of waveform 744, a relatively flat horizontal portion 756, and a trailing edge 758 which coincides in time with trailing edge 750 of waveform 744. The trailing edge 758 results from discharge of capacitor 268 through line 270 by operation of flip-flop 328 and switches 330,332 in the circuit of FIG. 6.

Waveform 760 is the signal on line 300 from timer 322 of FIG. 6 to convertor 290 in FIG. 5. It includes a pulse 762 which commands operation of converter 290. Pulse 762, in turn, is triggered by the array clock signal on line 440 from component 320 which is applied to timer 322 through line 338. The time delay between the leading edge of array clock pulse 730 and the leading edge of pulse 762 provides a setting time for the analog-to-digital conversion and has a duration of about 3 micro seconds. Waveform 764 is the signal from converter 290 applied to inverter 302 which is connected by line 304 to flip-flops 328 and 354 in FIG. 6 and to microprocessor 148 in FIG. 7 by line 366. It includes a pulse 766 which signals the end or completion of the analog-to-digital conversion provided by converter 290. The conversion time, i.e. operation of converter 290, measured between pulses 762 and 766 is about 2.5 micro seconds. The leading edge of pulse 766 triggers flip-flop 328 to cause discharge of capacitor 268 reflected in the fall of waveform 752, and it triggers flip-flop 354 to switch on the recharge signal 734.

The eight output pulses from A/D converter 290 represent the digitized value of each of the array output pulses or pixels. The relatively flat or horizontal top portions of the pixels processed by peak detector 230 enhances the ability of converter 290 to digitize the signals. In binary form the eight pulses provide a range of 0–255, i.e. $2^8$, for digitized values of each pixel amplitude. The same output quantities are obtained from latch 296 which enhances speed of transmission to and from bus portion 298.

When electrical power to the refractometer first is turned on, the program which will be described in detail presently initializes some variables and programs the timers in timer 322 and component 320. Component 320 sets the period for the array clock pulses of approximately 60 micro seconds. The timer 322 sets the start pulse period of approximately 80 milliseconds. The individual pixel data appears on input 234 of amplifier 232 and is amplified and processed by peak detector 230 as previously described and then applied to A/D converter 290. The conversion is delayed relative to the array clock pulses on line 184 in FIGS. 5 and 6 by a programmable delay set by timer 322 in FIG. 6 and applied to A/D converter 290 by line 300. The digitized pixel data from converter 290 and latch 296 then is directed by microprocessor 148 in conjunction with the program to either reference ram 164 or sample ram 168.

A program is executed to adjust the voltage for operating lamp 72. The maximum pixel amplitude is read for one entire scan of all 1024 elements in array 70 when surface 76 of prism 74 is clean. If the amplitude exceeds a predetermined maximum, the lamp voltage is adjusted by changing the digital value at the inputs to D/A converter 454 of FIG. 6, and this is continued by a successive approximation technique employing component 320 until the optimum valve is reached. It is necessary to adjust lamp voltage because a light level is needed at a certain point within a specific tolerance to provide the proper dynamic range of operation of linear scanned array 70. The array 70 has a definite saturation voltage with the result that an excessive light output from lamp 72 will cause problems as well as a deficient light level providing too small a dynamic range of operation.

When the optimum value of lamp voltage is reached, the program displays a message indicating that everything is functional. The operator then is prompted to depress INITIATE key 50 to request an initiate scan. The instrument will take a predetermined number of scans of array 70 for averaging purposes and store them in reference ram 164. Then when a sample reading is requested by depression of READ key 60, the array 70 is scanned a predetermined number of times and the digitized values are stored in sample ram 168. These values then are compared to the reference values to determine the crossover for a measurement of index of refraction.

Figure 10:
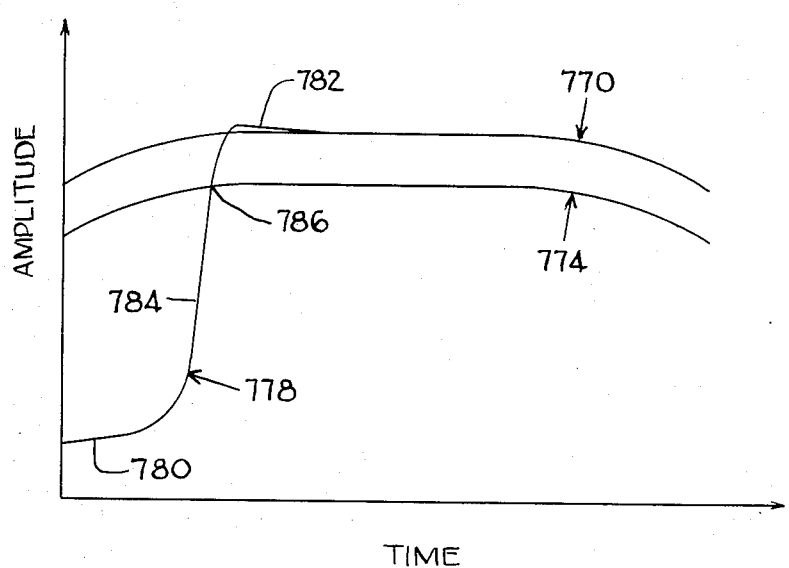
FIG. 10 is a graph including waveforms illustrating operation of the refractometer of the present invention.

The foregoing is illustrated by the graph of FIG. 10 where each waveform represents the sum of the individual pixels, i.e. the smallest resolvable output pulses, resulting from a scan of array 70. Waveform 770 represents the reference scan, i.e. the scan over time of the 1024 pixels resulting from a scan of all 1024 elements of array 70. It is the total illumination curve for air. The drop off on the left-hand and right-hand portions of curve 770 is due to optical effects associated with the prism, lenses, mirrors and aperture of array 70. A scale factor of 94 percent is applied to curve 770 resulting in the reference curve 774. Waveform 778 represents the sample scan, i.e. the sum over time of the 1024 pixels, resulting from a scan of all 1024 elements of array 70 when a liquid to be measured is placed on surface 76 of prism 74. The lower portion 780 of curve 778 corresponds to the dark portion of the array as previously described, the upper portion 782 corresponds to the light or fully illuminated portion, and transition region 784 is the gray portion. Point 786 is the intersection of the sample and reference scans which is utilized in computing the measured value of index of refraction.

The operation of the automatic refractometer of the present invention will be described further in conjunction with the program illustrated by the flow charts of FIGS. 11–25.

The assembly and PLM program shown is both an interrupt and poll-driven program. The input of the keyboard selection which is visually displayed, and taking into account the sample dependent properties of index of refraction and temperature, will produce a displayed result which can be interpreted dependent upon the mode setting. The displayed result along with the scale information can also be printed for hardcopy documentation.

The program includes several assembly and PLM modules for the 8085 microprocessor 148. Some modules are: Keyboard handler; Display; Computation of 4th order polynomial with variable coefficients; Digitization and storage of the linear scanned array output; Temperature measurement; calibration; and Printer driver. The following is a brief description of the program operation from power on.

Upon turning the power on, the program will initialize certain varibles, the display, and start the linear scanned array 70 with the proper timing parameters. Then partial power is applied to the light source 72 and a light distribution measurement scan is initiated to see if the light level is optimum. If not, the light level is re-adjusted and the procedure is repeated until the light level is optimum for the linear scan array and amplifier combination. If the light level does not meet minimum digital values, a message is displayed to indicate the problem. Otherwise the program waits for the next input.

With the light level optimally set, the keyboard is locked out to accept only the initialization command. When the initiate key 50 is pressed a reference scan of the light distribution across the array for all 1024 photodiodes is summed for 16 scans and then stored in the reference ram 164. If the scan passes a minimum digitized level, the program will show a greeting message. Now the complete keyboard inputs are allowed and operation is permitted as previously described.

Mode selection in response to depression of mode key 54 changes a pointer in the program called "Function Selected" and then updates the display. This is done in the "Mode Select Module". This change will then select the polynomials in proper order to obtain the proper display. Pressing of Calibrate key 56 will cause the system to go through an actual Read cycle and also temperature measurement. The reading will be referenced to 20 degrees C. and must fall within certain tolerance around cell number 30 in array 70. If not, an error message is displayed. Temperature keypress by means of key 58 will then initiate a temperature measurement cycle and display the temperature in degrees C. Channel keypress by means of key 52 will increment a "channel Number" function with a check on the upper limit by comparison to a "maximum Number Channels" function. This is used to select the appropriate coefficients when the polynomials are computed. The Read keypress by means of key 60 will start a measurement cycle in which the array output is read and stored in the sample ram 168. This data is then compared on a cell-by-cell basis adjusted until a match to the reference ram 164 occurs. This cell-crossing is further refined by calling the Interpolation routine to split the crossover into 10 parts to obtain the needed accuracy.

Although various program languages can be employed with the illustrated components described in FIGS. 5-8 PLM language was found to provide satisfactory results.

Figure 11:
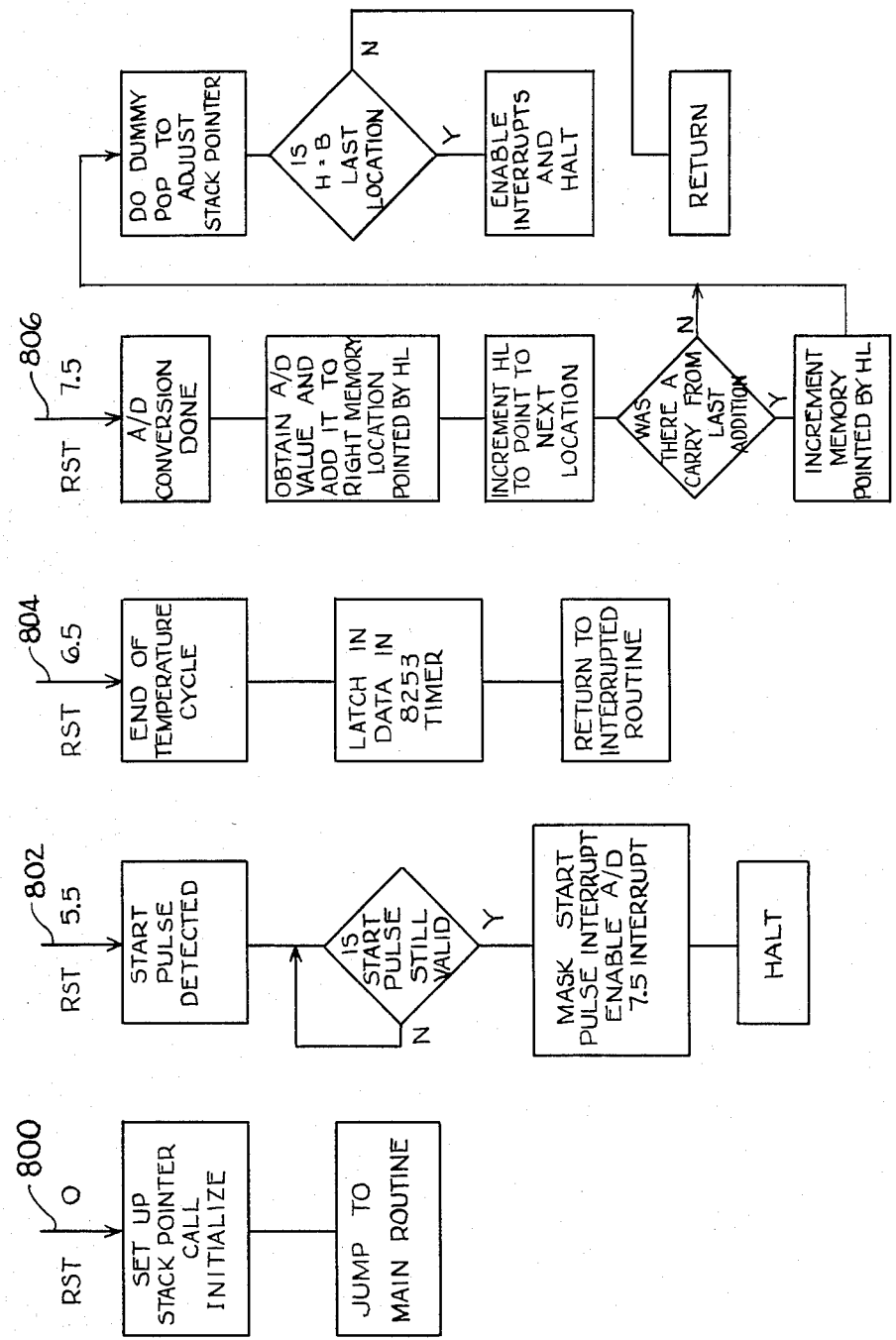

Referring now in detail to the flow charts of FIGS. 11-29 a jump table for operations associated with microprocessor 148 is shown in FIG. 11. When a pin on microprocessor 148 corresponding to a vector designated in FIG. 11 is active, if the program permits or enables, it proceeds to a memory location and the jump table comes into operation. The vector indicated at 800 and also designated RST 0 signals a power up condition and functions to call an initialization sub routine. When complete, interrupts are enabled and a jump to the main program occurs. An RST 5.5 vector designated 802 signals the routine to detect the presence of a start pulse on line 182 in the circuit of FIGS. 5 and 6 which also is present on RST 5.5 pin of microprocessor 148. When the start command for linear scanned array 70 occurs, this portion of the jump table masks the start pulse interrupt, i.e. RST 5.5, and enables the RST 7.5 interrupt of microprocessor and waits for a clock pulse. The RST 6.5 vector designated 804 is present when the temperature measuring period has ended. With the value in the programmable timer 322, the program is instructed to proceed with computing the temperature. The RST 7.5 vector 806 indicates that A/D connector 290 has finished with data. This section of the routine will take N readings and then obtain the average for the purpose of reducing noise effects.

Figure 12:
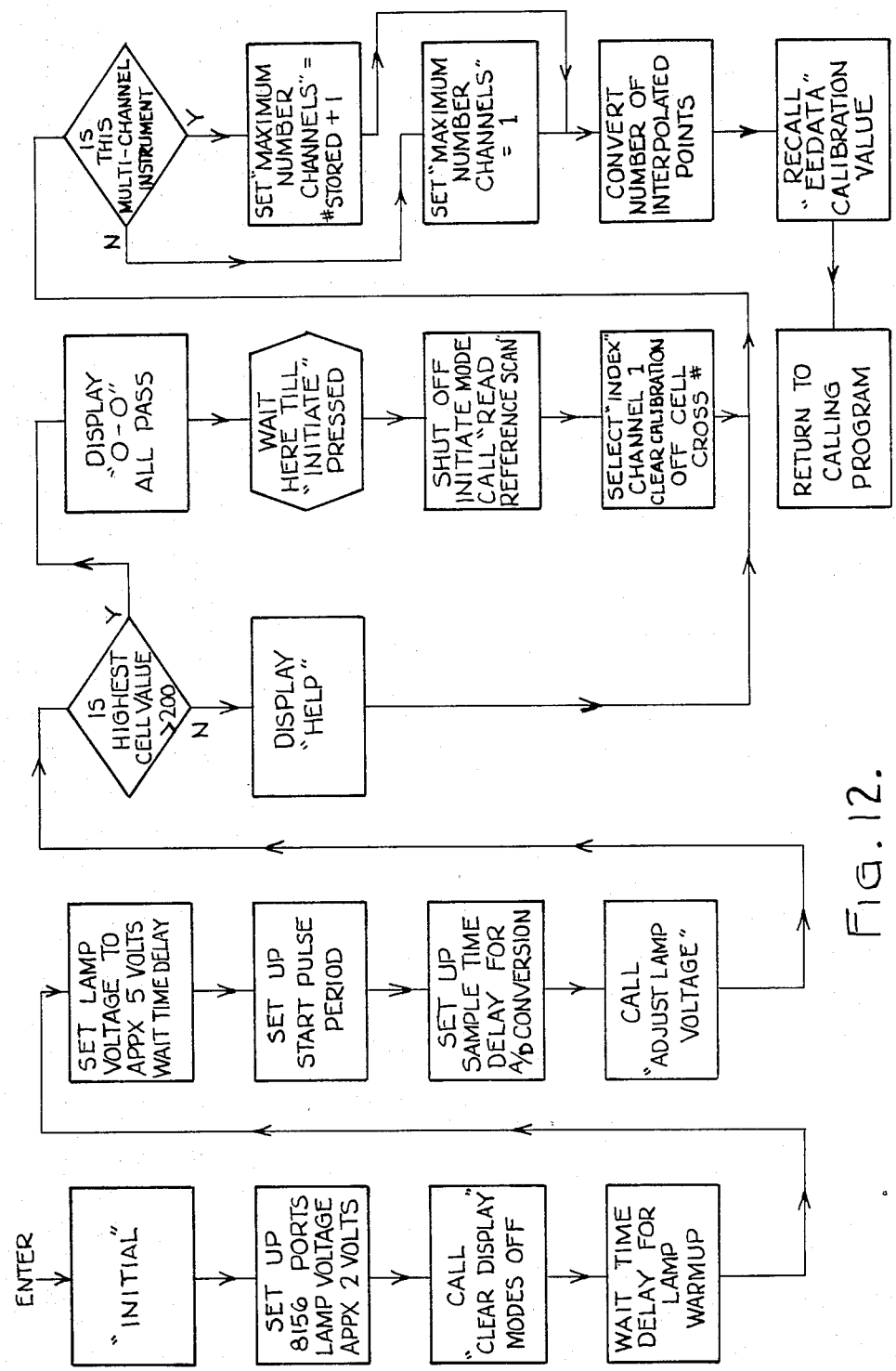
Figure 12A:
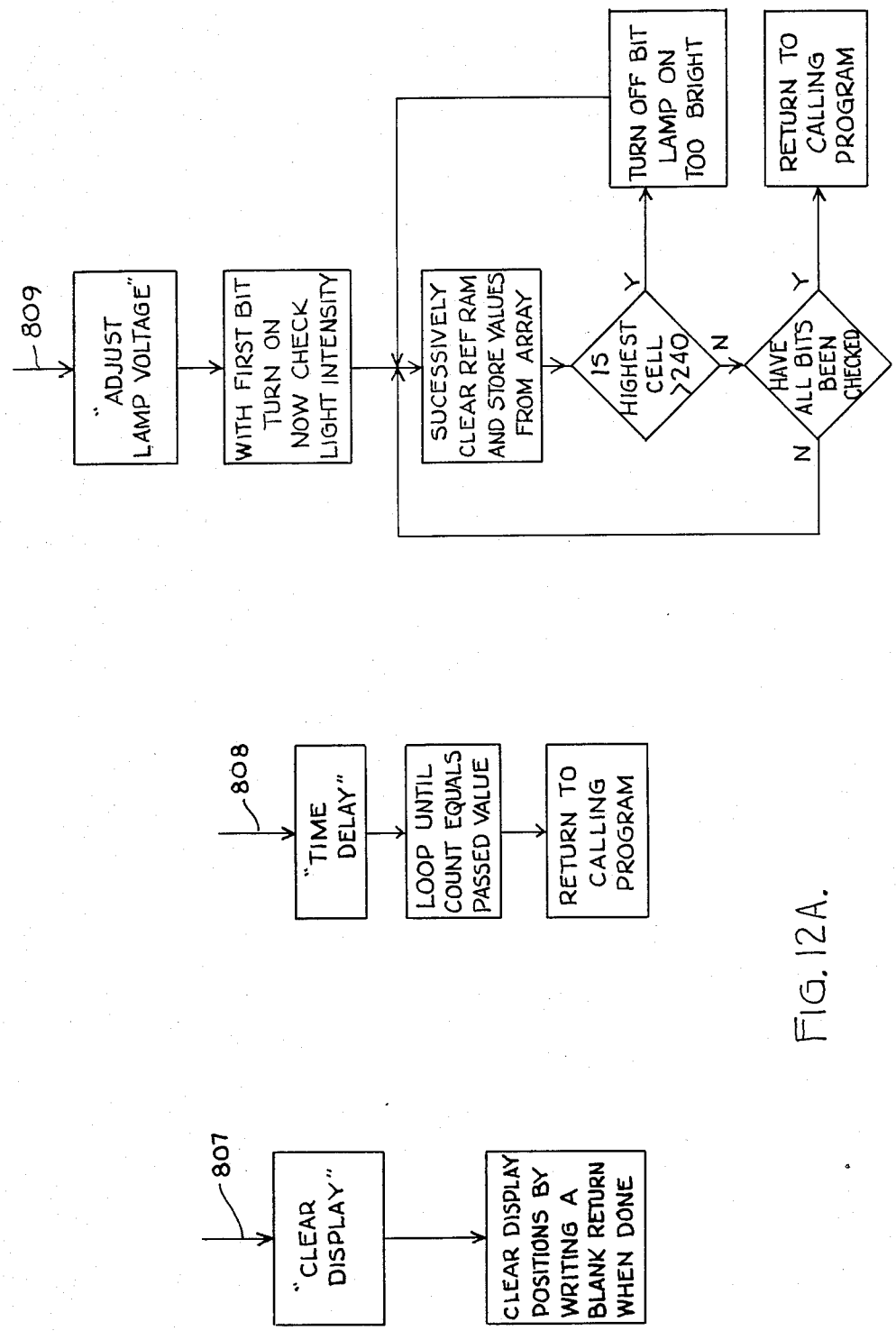

FIG. 12 shows the initialization routine or module called by the jump table of FIG. 11 upon power up. It is used to set up the ports and the timer periods of component 320 and the modes of timer 322 in the circuit of FIG. 6. Next, the display is blanked and preliminary indicators are set up. In particular, a "Clear Display" subroutine is called which is entered at 807 as shown in FIG. 12A. As indicated in FIG. 12, various time delays are employed which are implemented as shown by the subroutine entered at 808 in FIG. 12A. Next, the initialization routine of FIG. 12 calls for the "Adjust Lamp Voltage" subroutine which is entered at 809 as shown in FIG. 12A. In this subroutine the initialization or reference ram 164 is cleared to read one scan of the linear scanned array 70. The maximum amplitude is read and if less than a predetermined amount the voltage for light source 72 is increased until it is so. In particular, the amplitude of the highest cell is checked and the lamp voltage is adjusted until the amplitude of the highest cell is 240 or less. This section of the sub-routine will turn on the next smaller bit and test for the highest cell amplitude. If it is greater than 240 that bit will be shut off and this is continued until all bits have been tested. Finally, in the initialization routine of FIG. 12, the average initialization scan is determined and stored in the reference ram 164. In particular, if the highest cell value is greater than 200 a message is placed in the display to indicate passed. Then the number of interpolated points needed for cell calculation is found as illustrated in FIG. 12 including calling the "Read Reference Scan" routine which will be described, setting the maximum number of channels depending on whether or not the particular refractometer is multi-channel, and then recalling "EEDATA" in the appropriate prom after the number of points is determined.

Figure 13:
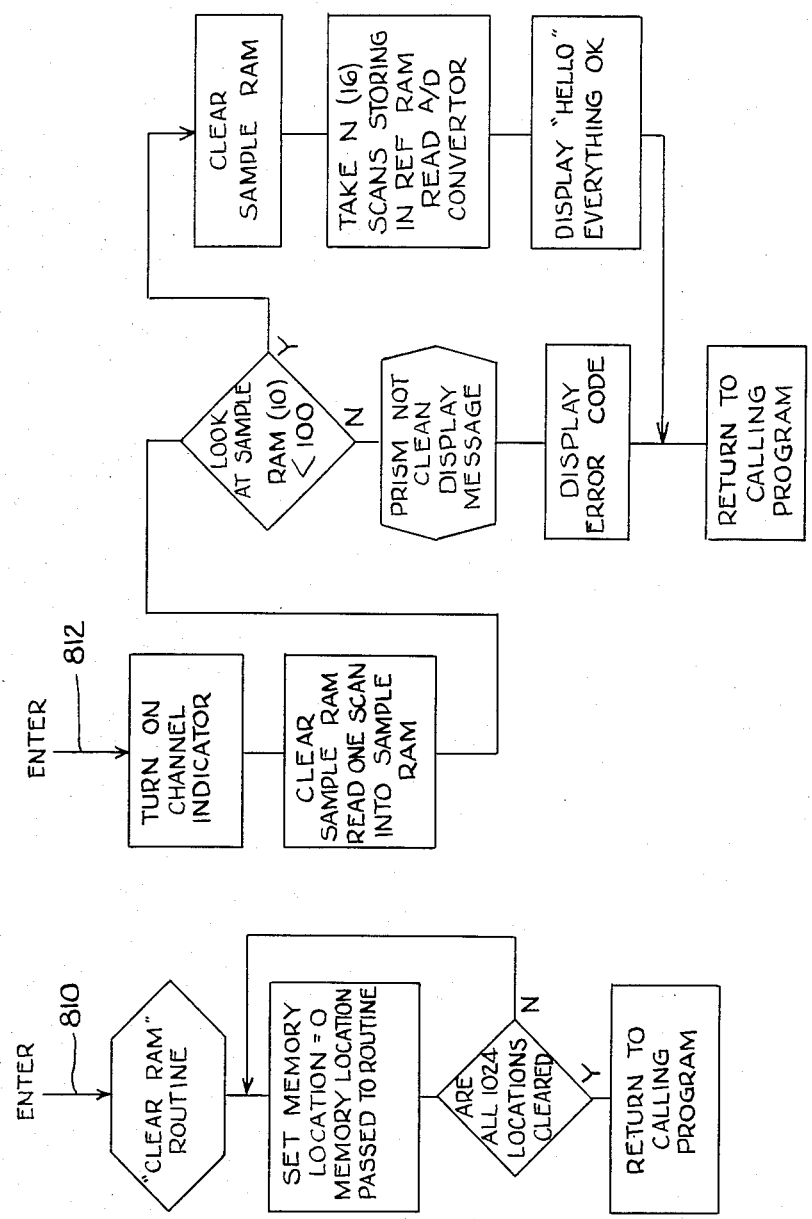
Figure 14:
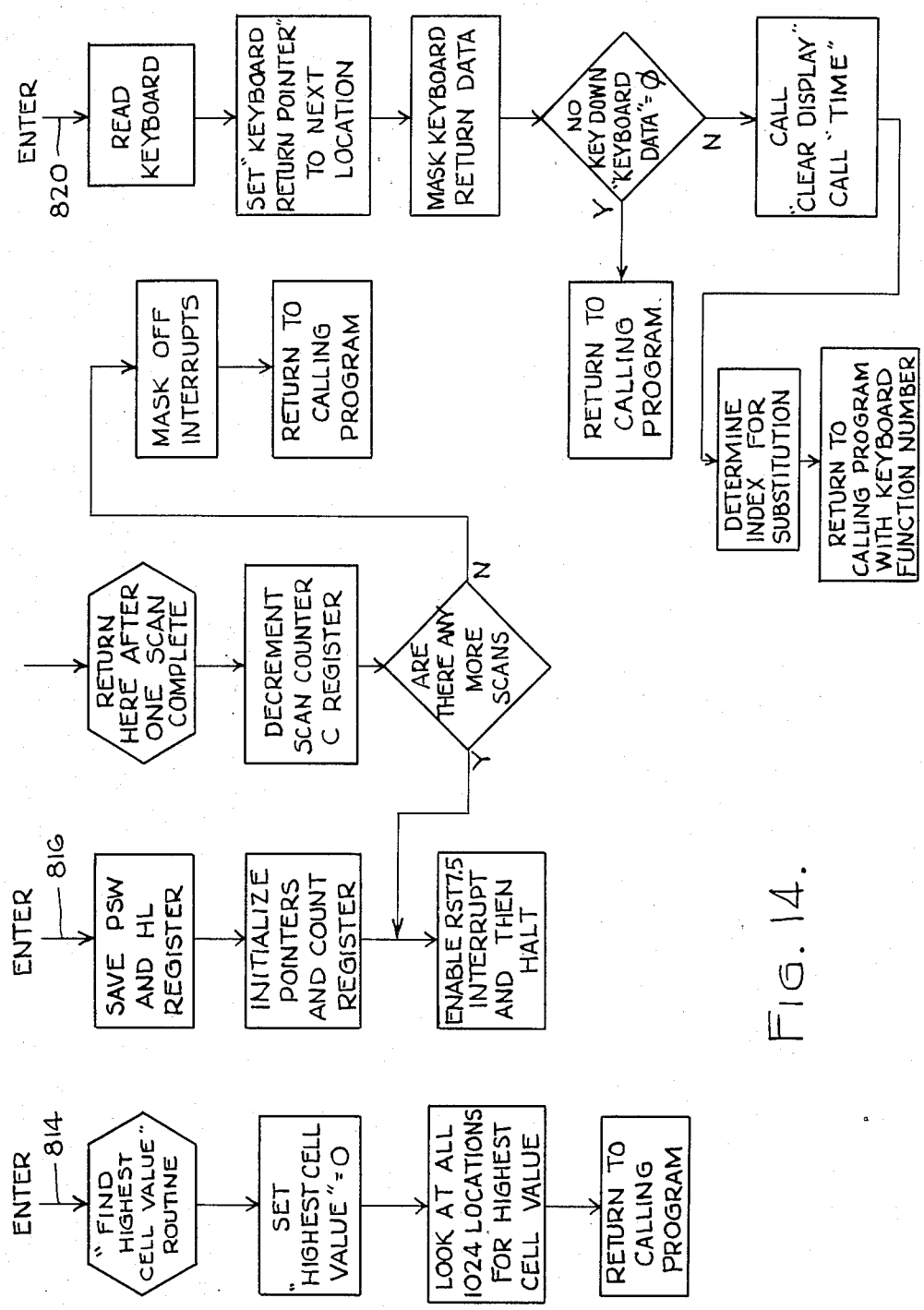

FIGS. 13 and 14 illustrate the "Clear Ram", "Read Reference Scan" and "Find Highest Cell Value" rouines called by the initialization program and subroutines of FIGS. 12 and 12A. In particular, the "Clear Ram" routine called by "Adjust Lamp Voltage" is entered at 810 in FIG. 13 and sets the 2K RAM whose address pointer has been passed to zero. The starting address is passed from the calling program. The "Find Highest Cell Value" routine also called by "Adjust Lamp Voltage" is illustrated in FIG. 14 where it is entered at 814. It finds the highest cell value in the selected 2K RAM, i.e. finds the highest digitized cell amplitude during any scan of array 70, and stores that value in the variable "Highest Cell Value".

The "Read Reference Scan" routine is illustrated in FIG. 13 and entered at 812. It is called by the initialization routine of FIG. 12. This module generates the reference scan and stores it in the reference ram 164. This is done by repeatedly calling for an A/D conversion of the cell values. First, the scan is stored in the sample ram 168 and checked if the initiate curve is valid or if the request is made on an unclean prism. If so, then an error message is displayed and the curve is restored to the reference ram 164. Otherwise, the average scan is taken and the appropriate message is displayed. In particular, first the program checks if prism 74 is clean by looking at one scan of array 70 and storing the data values in sample ram 168. Then the program looks at the first values to see if refraction has occured. If so, the request is ignored and an error message is displayed. Otherwise, the average is taken by gain calling the A/D conversion, storing the curve in reference ram 164 and displaying the "Hello" message.

FIG. 14 also illustrates the "Read A/D converter" routine called in the foregoing procedure and which is entered at 816. This module is called to set up the program loop that determines how many scans will be collected and where the date will be stored. The program returns with the sum values on "N" scans that was passed in the C register from the calling program. In particular, all registers are used and no values are returned. Inputs to the module include the number of scans required at the high order starting location of the RAM. Registers are used in the following way: A-accumulation and storage; B-end high order address loaded from E register+2048; C-from calling program containing the number of scans required; DE-point to the A/D converter address; and HL-point to the next storage location in the RAM.

Figure 15:
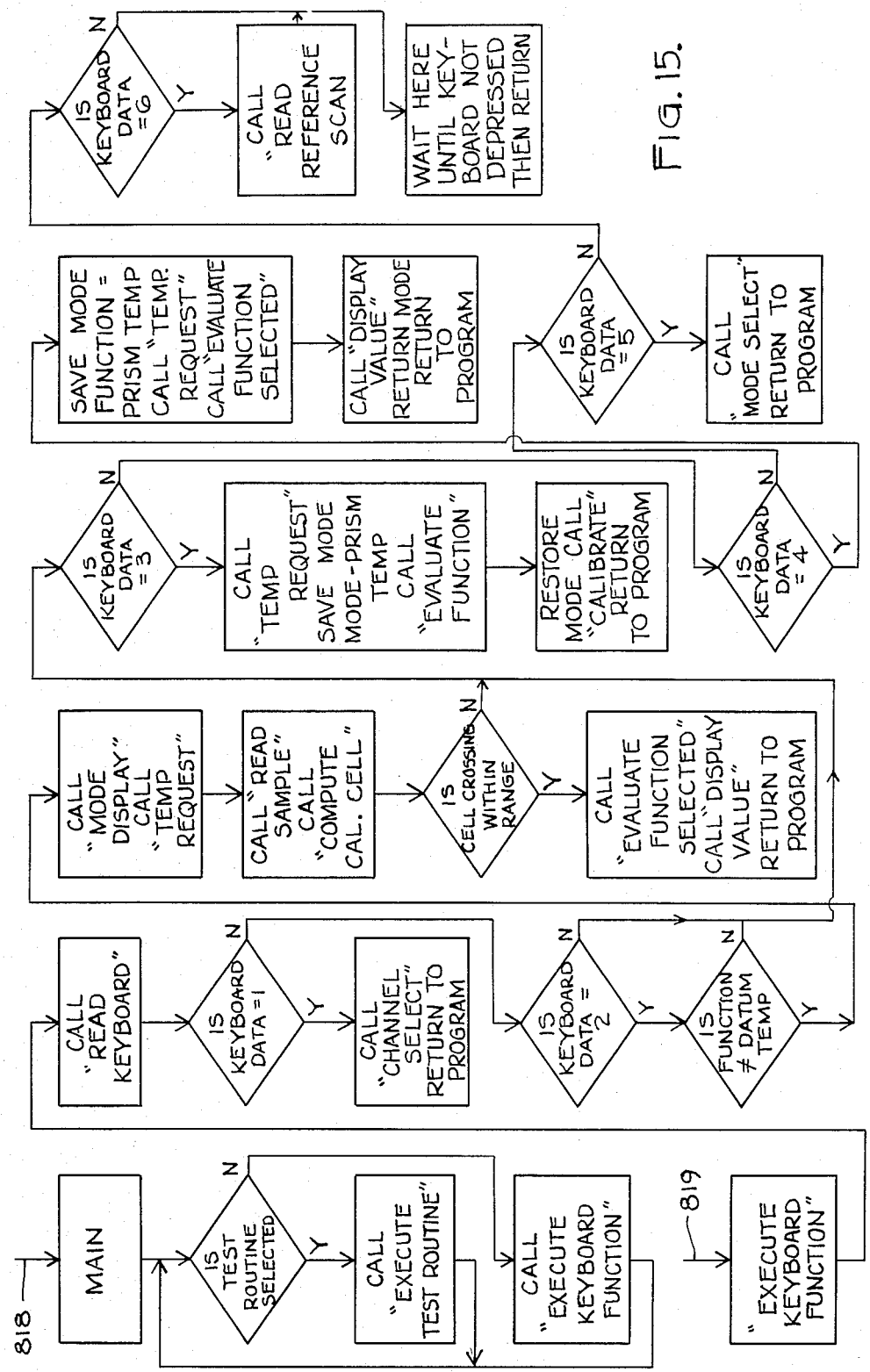

FIG. 15 shows at the left-hand side the main program which is reached through the jump table of FIG. 11 and entered at 818. The program first checks if a test routine is selected. If so, an "Execute Test Routine" is called which will be described presently. If not, the program calls the "Execute Keyboard Function" which is illustrated in the remainder of FIG. 15 and entered at 819. It first calls the "Read Keyboard" routine shown in FIG. 14 and entered at 820. The "Read Keyboard" routine obtains the keyboard data whereupon there is a return to the "Execute Keyboard Function" program which, as illustrated in FIG. 15, then proceeds to perform the various functions indicated including calling other routines dependent upon the keyboard information obtained, i.e. dependent upon which of the modes is selected by keys 50–60. In particular, keyboard data=1 corresponds to a channel request by key 52, keyboard data=2 corresponds to a sample read requested by key 60, keyboard data=3 corresponds to a calibrate request via key 56, keyboard data=4 corresponds to a temperature request by key 58, keyboard data=5 corresponds to a mode selection request from key 54 and keyboard data=6 corresponds to an initialization request by means of key 50.

Figure 16:
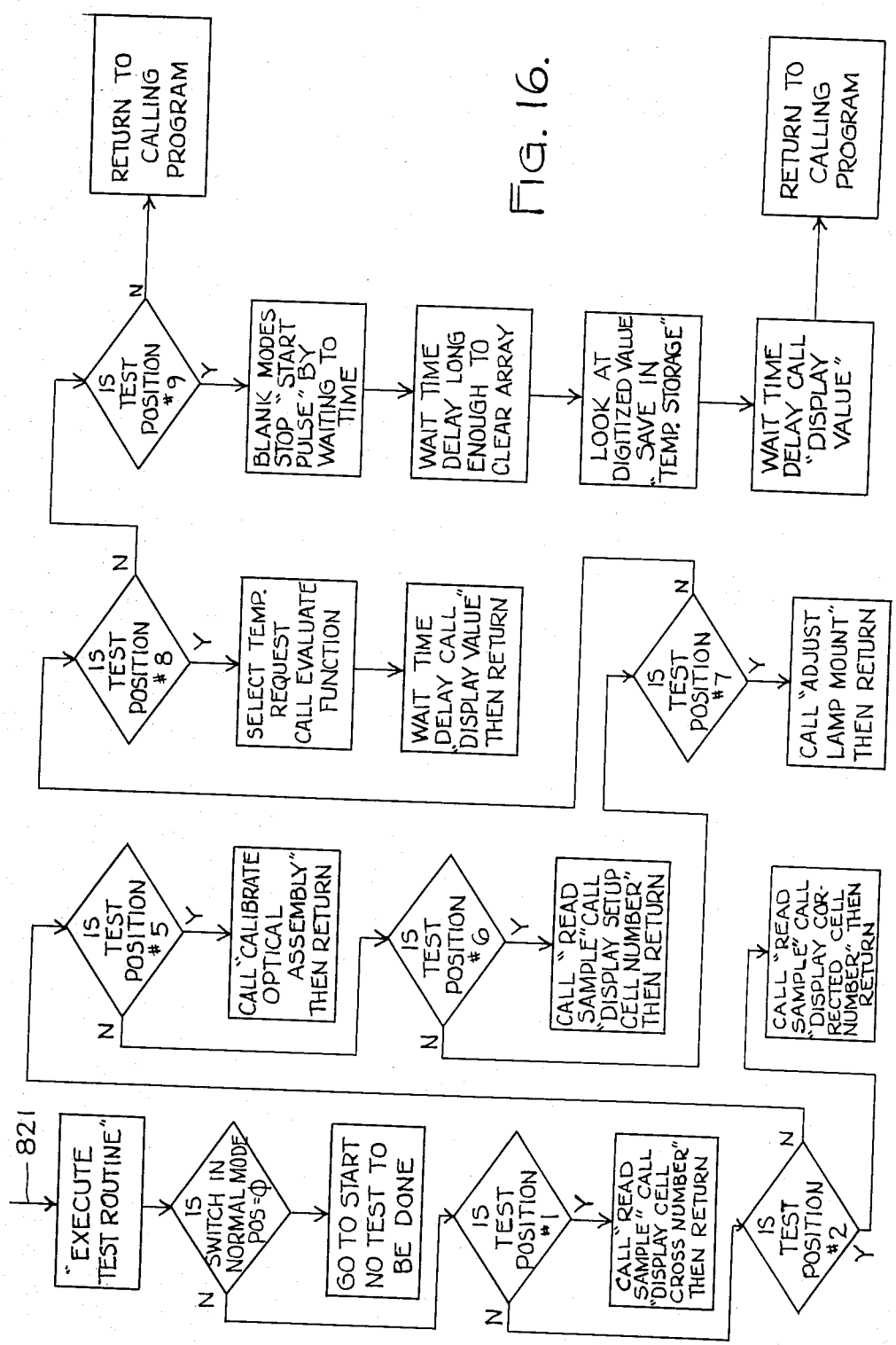

The "Execute Test Routine" is shown in FIG. 16 and entered at 821. The routine first determines if the test position is selected by the BCD switch and if so, i.e. byte read 1, the test is performed. Otherwise, if the byte read is zero corresponding to normal instrument usage, the program goes to the start condition. As illustrated in FIG. 16, switch positions 1 and 2 are for display of the cell crossing number and corrected cell crossing number, respectively, switch position 5 is for calling a "Calibrate Optical Assembly" routine which will be described, position 6 for calling "Read Sample" and for display of setup cell number during a variance from water position, position 7 is for calling an "Adjust Lamp Mount" routine which will be described, position 8 is for temperature display, and position 9 is for display of zero offset.

FIG. 16A illustrates the sub-routines "Display Cell Crossing Number", "Display Corrected Cell Number" and "Display Setup Cell Number" which are called by the "Execute Test Routine" program of FIG. 16 and which are entered at 822, 823 and 824, respectively.

Summarizing, the main program stays in an indefinite loop and looks for a keypress. If the instrument is in the test procedure mode and the test switch is not in position zero, the program will call up the test routine program. When a keypress occurs, it will process it based upon the mode of the instrument.

Figure 17:
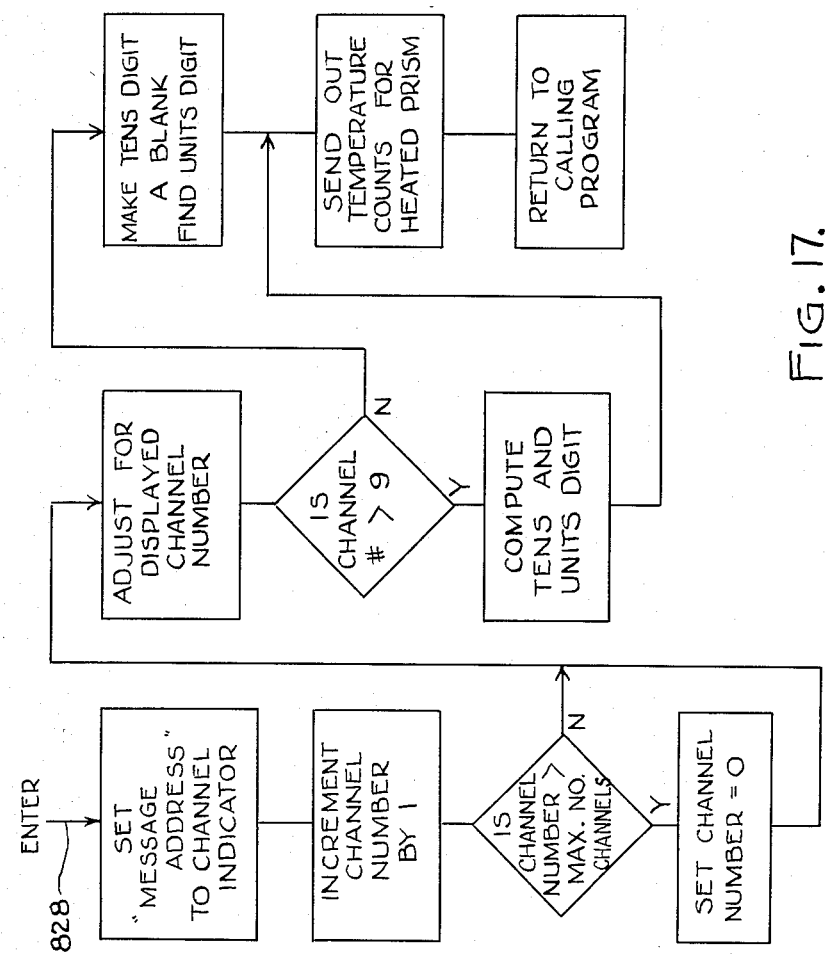

FIG. 17 illustrates the "Channel" routine called by the main program of FIG. 15 and entered at 828. When this channel select module is called, it increments the variable "Channel Number" and checks to determine if that variable exceeds the number of customer requested channels. The heated prism temperature control value, i.e. the count value necessary for temperature control, also will be sent out based on the desired datum temperature.

Figure 18:
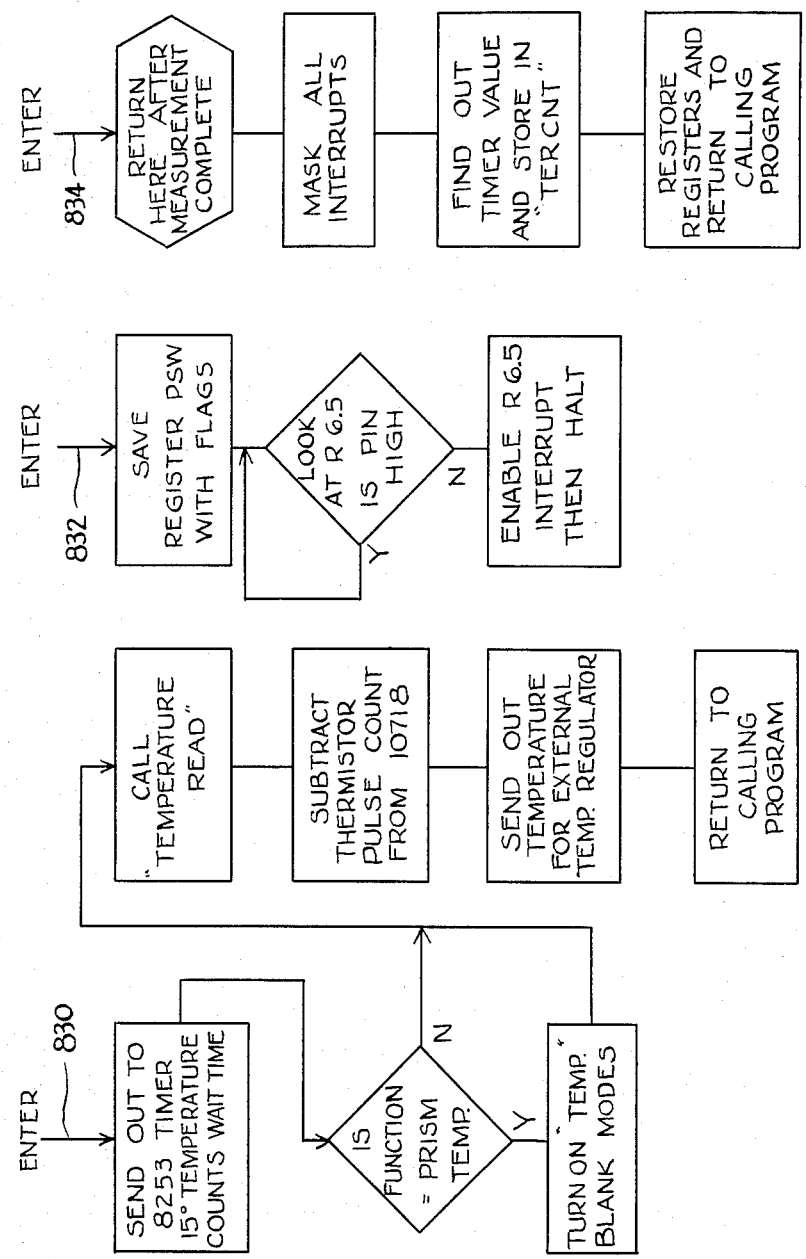

FIG. 18 shows the "Temperature Request" routine called by the main program of FIG. 15 and entered at 830. It begins by causing the 15° temperature counts to be sent to timer 322 for measuring temperature, including waiting a given time period for the counts to be accepted. If the function selected is prism temperature, then the message address is temperature degrees C. and the mode display address is blank. Otherwise the program proceeds to call a "Temperature Read" routine which also is illustrated in FIG. 18 and is entered at 832. It proceeds to save register and flags, obtain pending interrupts, loop until the RST 6.5 pin on microprocessor 148 is low, whereupon it then allows that interrupt and waits for the result. Then it proceeds to point 834 indicated in FIG. 18 where it masks all interrupts, obtains the value from timer 322, stores the value in the variable "TERCNT", restores the registers and returns to the remainder of the "Temperature Request" routine. The latter routine then proceeds to obtain a value by subtracting 10718 from the thermistor pulse count and then sends out a control signal to an external temperature regulator.

Figure 19:
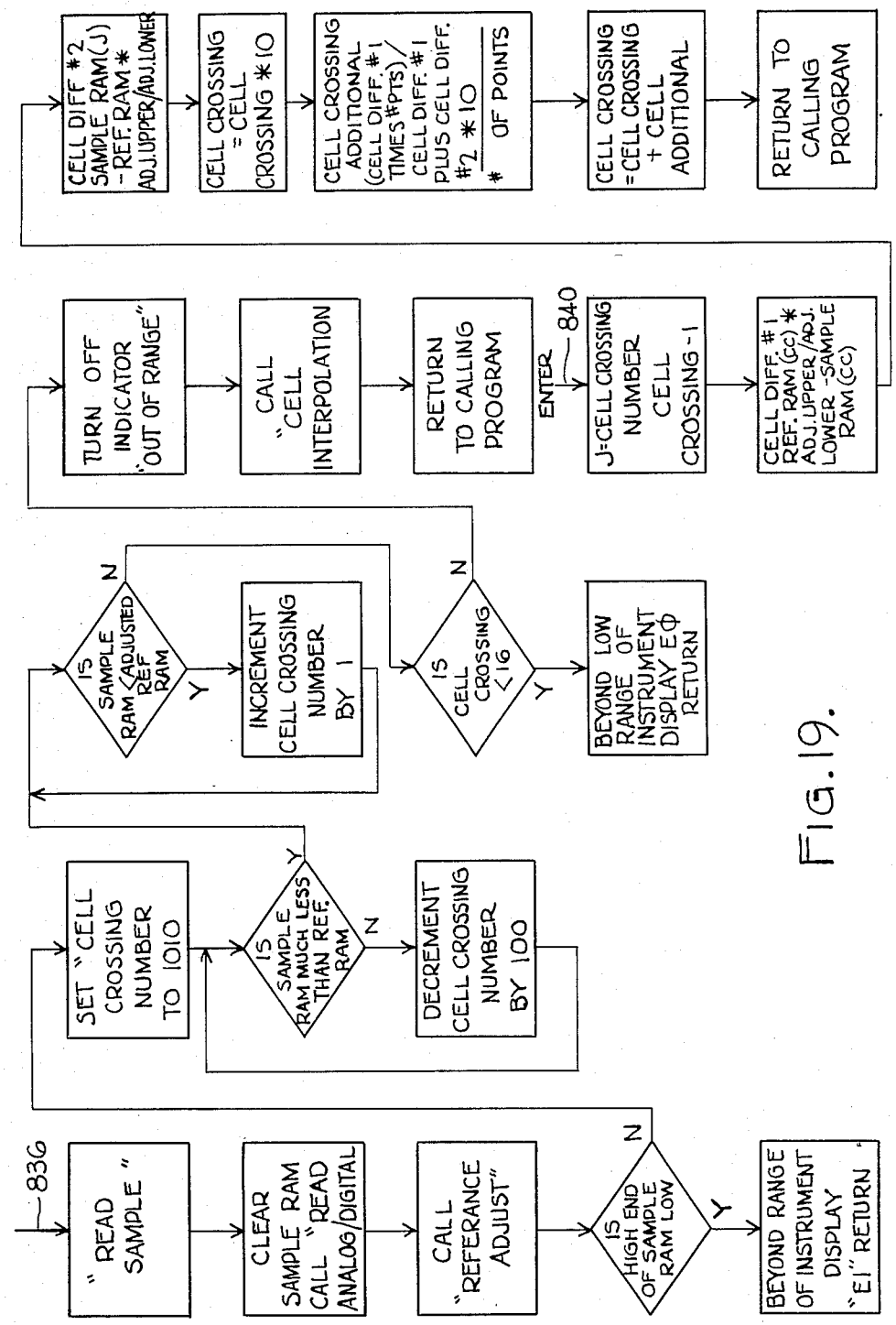

FIG. 19 illustrates the "Read Sample" routine called by the main program of FIG. 15 and entered at 836. It begins by clearing sample ram 168 and by calling the "Read A/D Converter" routine previously shown and described in connection with FIG. 14. Next, the routine checks if the reference curve has shifted either due to lamp output variations or temperature change, whereupon the reference curve is adjusted. This is accomplished by calling a "Reference Adjust" routine which will be described. The remainder of the program determines the cell crossing number when the sample ram value exceeds the reference ram value, and it adjusts the sample curve by the ratio of adjustment upper/adjustment lower. The cell crossing number is the number of the particular photodiode or element of array 70 corresponding to the intersection 786 in FIG. 10. The search procedure to find the cell crossing number includes, briefly, first reaching backward by 100 cells from the highest cell and then refining by searching forward by one cell. In particular, as shown in FIG. 19, firs a determination is made if the high end of the sample RAM 168 is low and if it is an out of range message is displayed. Otherwise, the routine proceeds to initialize the cell crossing number by setting it equal to 1010. Next a determination is made if the sample RAM quantity is much less than the reference RAM quantity. If not, the cell crossing number is decremented by 100 and the determination made again, and if it is the routine proceeds to the next determination. If the cell crossing number in sample RAM 168 is less than the adjusted cell crossing number in reference RAM 164, the cell crossing is incremented by 1 and the determination is repeated. Otherwise, if the sample RAM quantity is not less than the adjusted reference RAM quantity, a determination is made if the cell crossing number is less than 16. If so, it is below the low range of the instrument and a message to that effect is displayed. If not, the program proceeds to turn off the out of range message and to call the "Cell Interpolation" routine.

Summarizing, in the "Read Sample" routine first the selected number of scans are stored in sample RAM 168 and the the reference curve information is adjusted to take into account the drift that may have occurred. Next, the coarse search to find the cell crossing is done by looking backward from the highest cell location. Then a forward search cell by cell is done by looking for the cell crossing that meets ths specified gray level. When this is formed, the cell interpolation routine is called to find the fractional cell level that represents the required data value.

Figure 20:
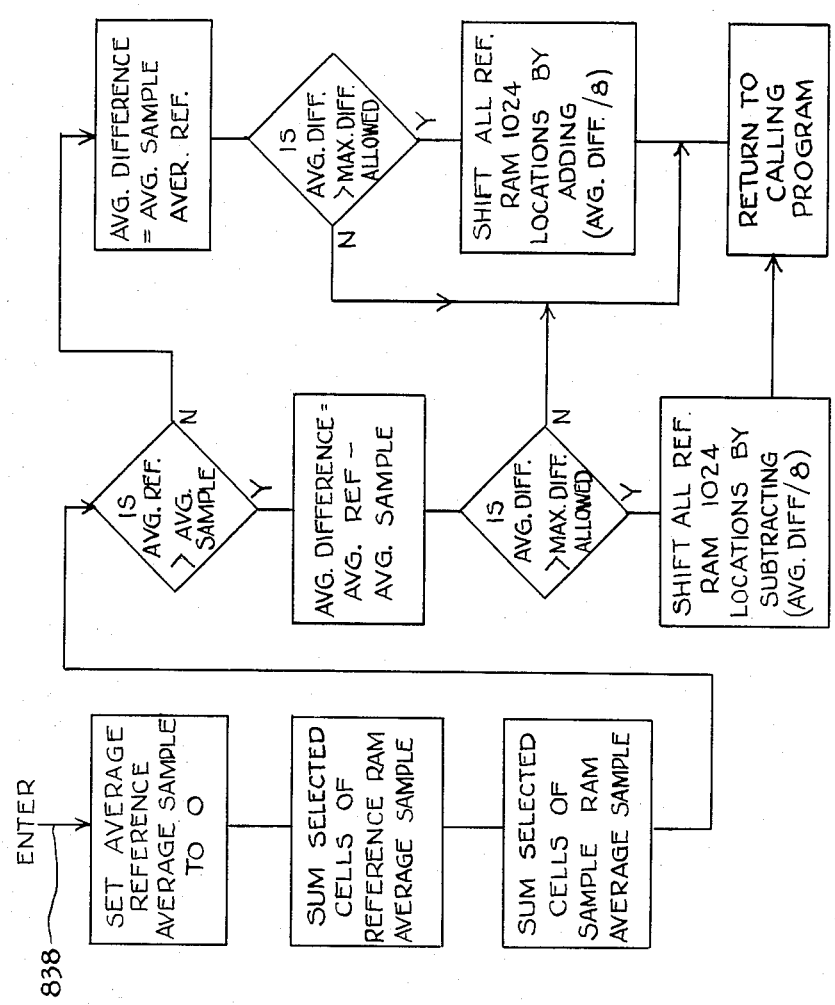

The "Reference Adjust" routine called by the "Read Sample" routine is shown in FIG. 20 and entered at 838. Briefly, this module is called to check if the light intensity has shifted. If so, an adjustment is made on the reference level curve stored in RAM 164 before determining the cross-over point. The "Cell-Interpolation" routine called by the "Read Sample" program is illustrated in FIG. 19 and entered at 840. It interpolates to find the partial cell crossing and the adjusts the variable, cell crossing number, by adding to the previous cell. Then it computes the additional fraction of cell to be added, and increments the cell number by the fraction computed. The foregoing is summarized as follows:

Cell Diff #1 = Ref RAM at Cell Crossings * $\frac{\text{Adj. Upper}}{\text{Adj. Lower}}$ Cell Diff. #2 = Sample Ram (Cell Crossing − 1) −

Ref. Ram (Cell Crossing − 1) * $\frac{\text{Adj. Upper}}{\text{Adj. Lower}}$

Fractional Part of Cell =

Figure 21:
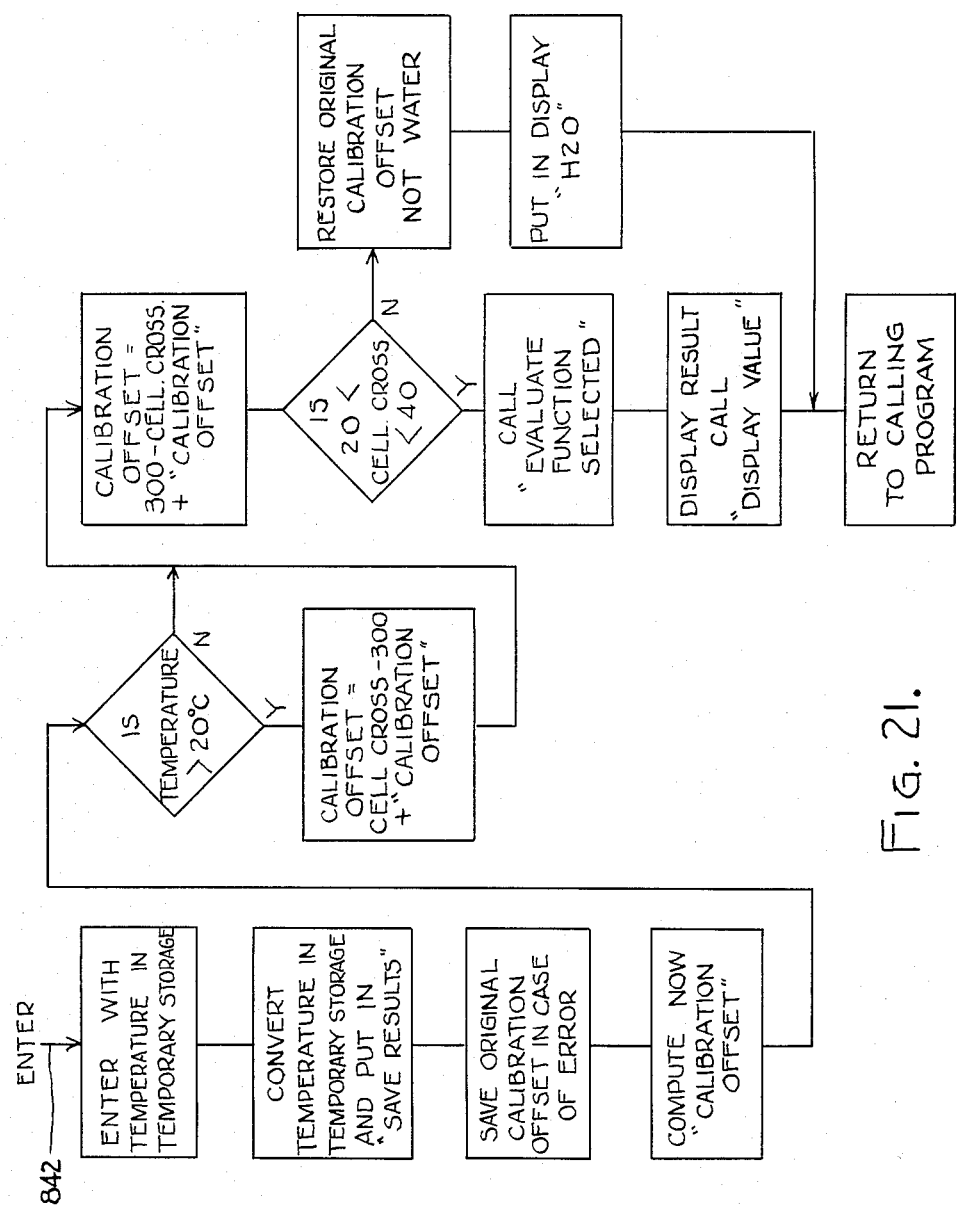

$\frac{(\text{Cell Diff. \#1}) * (\text{Num. of Points})}{\text{Cell Diff. \#1} + \text{Cell Diff. \#2}} * \frac{10}{\text{Num. of Points}}$ FIG. 21 illustrates the "Calibrate" routine called by the main program of FIG. 15 and entered at 842. When called, this routine answers that water is on prism surface 76. The cell crossing will be determined and the temperature is then measured. The relationship will be used to calculate the quantity "Calibration Offset" which represents the "Error" function to correct for mechanical variations other than cross-over at array cell no. 30. In this connection, all solutions inspected by the refractometer are referenced to temperature of 20° C. and cross over at cell no. 30 for distilled water. The first portion of the routine takes the count in timer 322 which is related to temperature, corrects the temperature value to a whole number of tenths of degrees and places it in an area in the program memory 160. The next portion of the routine computes the offset from array cell no. 30 for water having a temperature different from 20° C. Before that is done the calibration offset quantity is saved in case the calibration is not valid for a later restoration. As indicated in FIG. 21, the computation of calibration offset is handled for situations above and below 20° C. whereupon a cell crossing between 200 and 400 indicates a valid calibration, the result of which is displayed, otherwise the routine determines that the substance is not water and displays a signal requesting use of water for the calibration.

Figure 22:
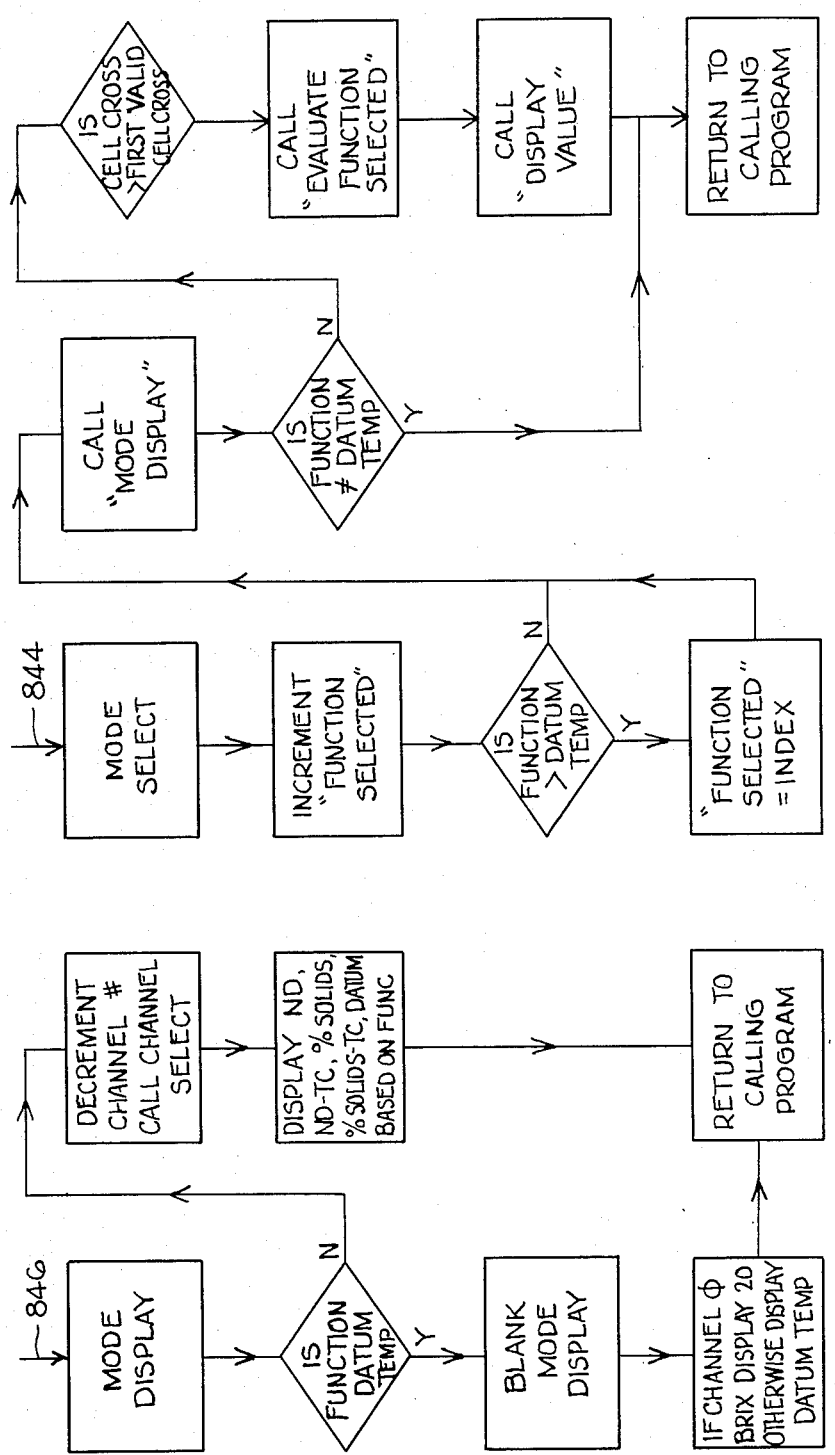

FIG. 22 illustrates the "Mode Select" routine called by the main program of FIG. 15 and entered at 844, and also illustrates the "Mode Display" routine called by the main program and by the "Mode Selecte" module and which is entered at 846. In the "Mode Select" routine, the variable "Function Selected" is incremented by 1 and if it is greater than Datum Temperature than the "Function Selected" variable is reset to Index, otherwise "Mode Display" is called. Next a determination is made if the incremented function is equal to Datum Temperature, and if it is and if the cell crossing number is greater than the first valid cell crossing, the routine calls "Evaluate Function Selected" and then calls "Display Value". This allows recomputation of the value by changing mode without having to depress the Read key. In the "Mode Display" routine shown in FIG. 22, if the function selected is Datum Temperature, then the mode display address is blank modes and if Channel Number is zero the display indicates 20 degrees for the Brix scale, otherwise the display indicates the temperature the scal is based on. If the function selectes is not Datum Temperature, the channel number is decremented, "Channel Selecte" is called, and the program proceeds through the various mode display addresses as indicated.

Figure 23A:
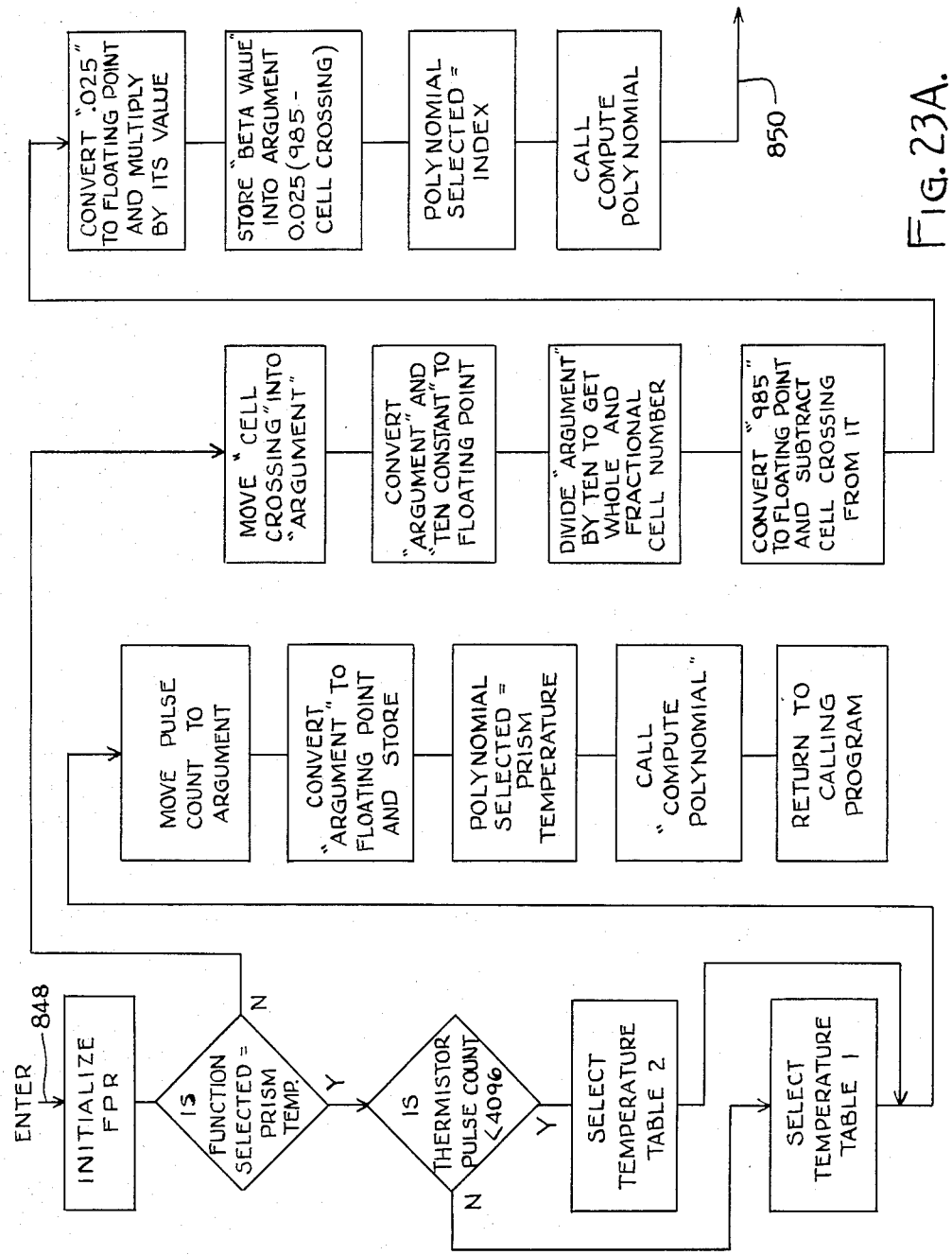
Figure 23B:
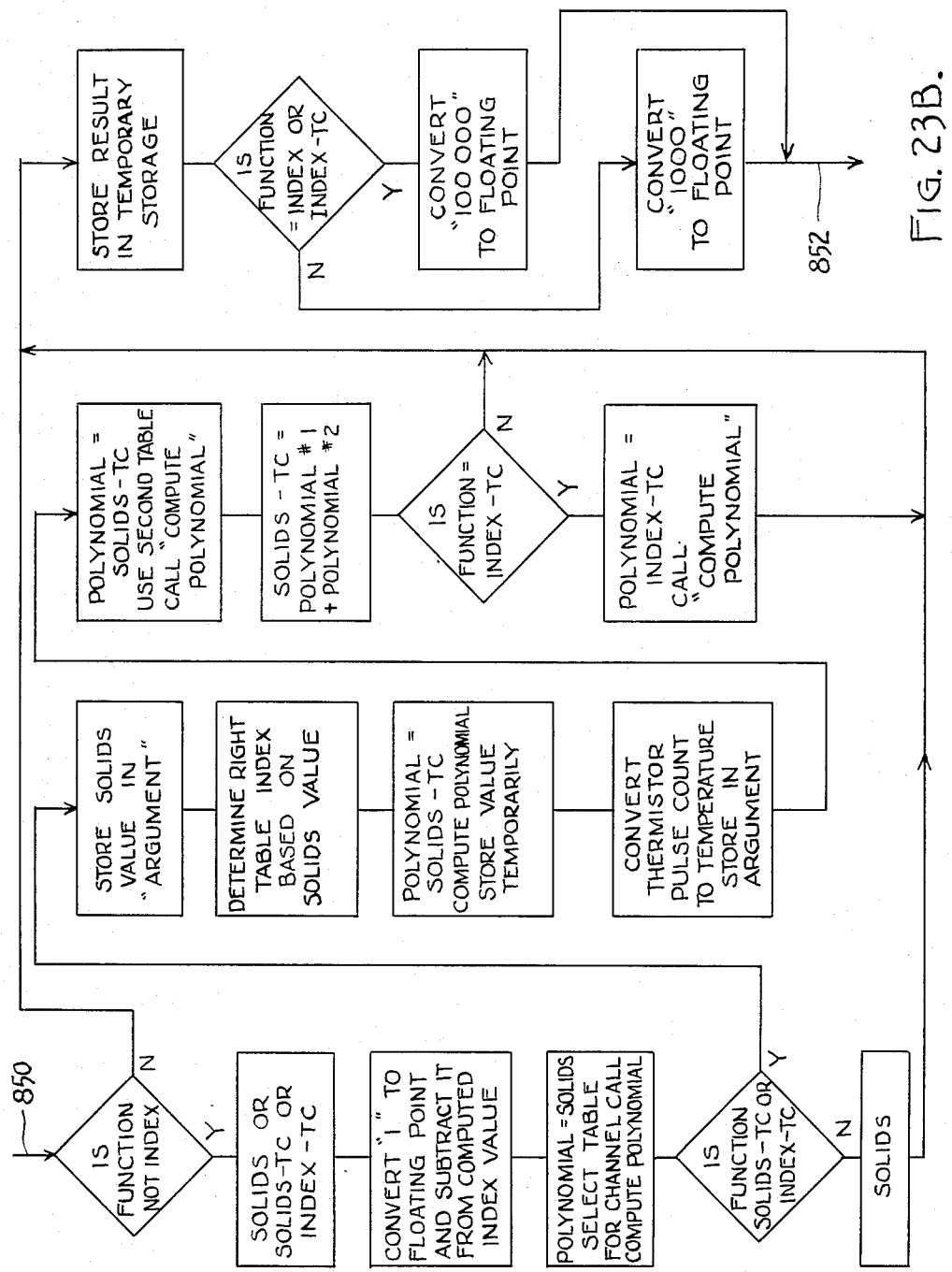

FIGS. 23A, 23B and 23C illustrats the "Evaluate Function Selected Routine" which is called by the main program of FIG. 15 and by the "Calibrate" routine of FIG. 21. This module which is entered at 848 selectes the proper polynominals in order for the selected funcition: SOLIDS, SOLIDS-TC, INDEX, INDEX-TC and TEMP. First, the variable FPR is initialized and then a determination is made whether or not the function selected is prism temperature. If it is not, the routine procees in a manner which will be described. If the selected function is prism temperature, then the thermistor pulse count is inspected to determine which temperature table is selected from memory to provide a temperature table offset per scale. Next, the pulse count is moved to the argument of a fourth order polynominl to provide the X value thereof as will be described. The argument then is converted to floating point, the program indicates that the polynominal selected corresponds to prism temperature, and a compute polynomial routine is called which will be described.

If the selected function is not prism temperature, the program proceeds in the manner illustrated in FIGS. 23 A-C. First, the cell crossing number is moved into the quantity "Argument". Then the number of interpolated points is converted to a floating point number, and the cell crossing number then is converted to floating point. Then there is division by the number of interpolated points to get a whole and fractional cell number. Then the compute polynomial routine is called in a manner which will be described. In the foregoing procedure, 985 is the maximum number of cells in the array, and 0.025 is the spacing between cells.

The program proceeds through the path designated 850 in FIGS. 23A and 23B for a determination whether or not the selected function is INDEX. If not, the function is either SOLIDS, SOLIDS-TC or INDEX-TC as indicated, and the program proceeds to store the Nd value, convert 1 to floating point, save temporarily, reload the computed index value, determine Nd-1, and save the value to use in calculations. Next, if the function selected is only SOLIDS, with no temperature compensation, the program proceeds to select for the particular channel a solids table offset per scale and then calls the compute polynomial routine.

Next, a determination is made if the function is SOLIDS-TC or INDEX-TC. If not, it is SOLIDS and the program proceeds in a manner which will be described. If the function is SOLIDS-TC or INDEX-TC the program saves the SOLIDS value for calculations and then determines the proper table index based on solids value. With one table being selected, the program calls the "Compute Polynomial" routine and the resulting value of polynomial #1 is placed in temporary storage. Then the temperature is determined by placing the thermistor pulse count in the argument. Then using a second table selected as described above, the "Computer Polynomial" routine is called again and the resulting value of polynomial #2 is temporarily stored.

FIG. 22 illustrates the "Mode Select" routine called by the main program of FIG. 15 and entered at 844, and also illustrates the "Mode Display" routine called by the main program and by the "Mode Select" module and which is entered at 846. In the "Mode Select" routine, the variable "Function Selected" is incremented by 1 and if it is greater than Datum Temperature then the "Function Selected" variable is reset to Index, otherwise "Mode Display" is called. Next a determination is made if the incremented function is equal to Datum Temperature, and if it is and if the cell crossing number is greater than the first valid cell crossing the routine calls "Evaluate Function Selected" and then calls "Display Value". This allows recomputation of the value by changing mode without having to depress the Read key. In the "Mode Display" routine shown in FIG. 22, if the function selected is Datum Temperature, then the mode display address is blank modes and if Channel Number is zero the display indicates 20 degrees for the Brix scale, otherwise the display indicates the temperature the scale is based on. If the function selected is not Datum Temperature, the channel number is decremented, "Channel Select" is called, and the program proceeds through the various mode display addresses as indicated.

FIGS. 23A, 23B and 23C illustrate the "Evaluate Function Selected Routine" which is called by the main program of FIG. 15 and by the "Calibrate" routine of FIG. 21. This module which is entered at 848 selects the proper polynomials in order for the selected function: SOLIDS, SOLIDS-TC, INDEX, INDEX-TC and TEMP. First, the variable FPR is initialized and then a determination is made whether or not the function selected is prism temperature. If it is not, the routine proceeds in a manner which will be described. If the selected function is prism temperature, then the thermistor pulse count is inspected to determine which temperature table is selected from memory to provide a temperature table offset per scale. Next, the pulse count is moved to the argument of a fourth order polynomial to provide the X value thereof as will be described. The argument then is converted to floating point, the program indicates that the polynomial selected corresponds to prism temperature, and a compute polynomial routine is called which will be described.

Then, as indicated in FIG. 23B, SOLIDS-TC is determined as the sum of polynomial #1 plus polynomial #2. This approach is used to accomodate three dimensional curve fit in determining the cell crossing.

Next, a determination is made if the function is INDEX-TC. If not, the program proceeds in a manner which will be described. If it is, then the Computer Polynomial routine is called. The remainder of the program continues from the SOLIDS indication previously described, i.e. at the lower left in FIG. 23B, from the not INDEX-TC determination, and from the computation of INDEX-TC. The result is stored in temporary storage, and a determination is made if the function at this point is INDEX or INDEX-TC. If it is, the constant 100,000 is converted to floating point and the process proceeds along path 852. If it is not, the constant 1000 is converted to floating point and the process proceeds along path 852. The resulting quantity is multiplied by the value in the temporary storage. Next, the program variable status is checked to determine if it is a negative number. If it is, a routine "FIXSD" is called to make the number positive and there is a return to the calling program, otherwise there is a direct return to the calling program.

FIG. 24 illustrates the Compute Polynomial routine which is called by many of the system programs as previously described. This module will compute a fourth order polynomial with the coefficients selected from a coefficients module. The structure is as follows:

$$Y = A0 + A1*X + A2*X*X + A3*X*X*X + A4*X*X*X*X$$

which can be rewritten as follows:

$$Y = A0 + X*(A1 + X*(A2 + X*(A3 + X*A4))).$$

The program, which is entered at 854, computes the above function by looping five times which, in turn, is done by looking up an ASCII value stored in a table which is converted by a call to a routine "FQFD2B" which leaves the result in the variable "FAC". First, as indicated in FIG. 24, the quantity "Function Value" is initialized with floating point zero, the quantity FPR is cleared, and the counter is initialized. The following loop is executed five times, once for each of the table coefficients for INDEX, INDEX-TC, SOLIDS, SOLIDS-TC, and TEMP, thereby providing a do case for table selection. By way of example, the do statement for INDEX is as follows:

Index table coefficients */ Control sign=index § coefficients (I) sign § mantissa; If index § coefficients (I) sign § exponent then /* is negative? */ control scale exponent § adjust=index § coefficients (I) exponent */ Else Control scale=exponent § adjust+index § coefficients (I) exponent; Control string §PTR=index § coefficients (I) Mantissa Similar do statements are provided for the other four functions and are summarized in FIG. 24. At the end of the do case for table selection the routine "FQFD2B" is called, multiplication is by FPR, storage is in Control and the number is converted to binary and then left in FPR. The routine FADD is called, multiplication is by FPR, and storage is in Function Value to provide a constant plus temperature result. After this, a determination I>0 is made; if I>0 then this is not the last coefficient and the program keeps looping. Otherwise, the routine FMUL is called and there is multiplication by "Argument" and storage in Function Value. The loop counter is decremented and the end of the computational loop is reached.

Various modules are provided for coefficients and constants used in the foregoing program. In particular, a first module contains the coefficients used to compute the fourth order polynomial for temperature, Nd computations. These are fixed in the system as constructed. A second module contains the coefficients used to compute a fourth order polynomial used for SOLIDS and SOLIDS-TC. They are based on data provided by the particular user. A third module contains all the defined constants used in the program and which are converted using the FPAL routine "FQFD2B". Considering the first module, it is a coefficients table module and after appropriate negative and positive declarations, it declares the INDEX coefficients structure, there being 5, declares the INDEX-TC coefficients structure, there being also 5, and it declares the TEMP coefficients structure, there being 10. After that the end of the coefficients table module is reached.

Turning now to the second module, it also is a coefficients table module and initially appropriate negative and positive declarations are made. The number of channels is stored in "MAXIMUM NUMBER OF CHANNELS", and when a new scale is defined this value is adjusted to reflect the addition. The number of scans is stored in "NUMBER OF SCANS", and this value is adjusted to change the averaging done on the signal. The datum temperature for each scale is saved here, and the set point temperature is adjusted using a table of temperatures ranging from 15-60 degrees and counts ranging from 10718 to 10783. A datum temperature data structure is declared for 5 scales by first placing the tens digit followed by a comma then the ones digit followed by a comma and finally the counts from the aforementioned table for 5 selected temperatures. To obtain the data for the SOLIDS and SOLIDS-TC scales, the next structure size is computed by using 5 as the number of scales. In particular, a SOLIDS coefficients structure is declared containing five data quantities, the next structure size is computed by using 10 as the number of scales, and then a SOLIDS-TC coefficients structure is declared containing 40 data items starting with BRIX>15 percent, 15%≦BRIX≧40% at the 11th item, 40%≦BRIX≧70% at the 21st item and BRIX≧70% at the 31st item. Upon completion of this data structure, the coefficients table module is completed.

The third module is the floating point constants module and includes structures for the cell spacing constant, maximum cell number constant, number of interpolated points constant, the one constant, the ten constant, the one hundred thousand constant and the one thousand constant.

Figure 25A:
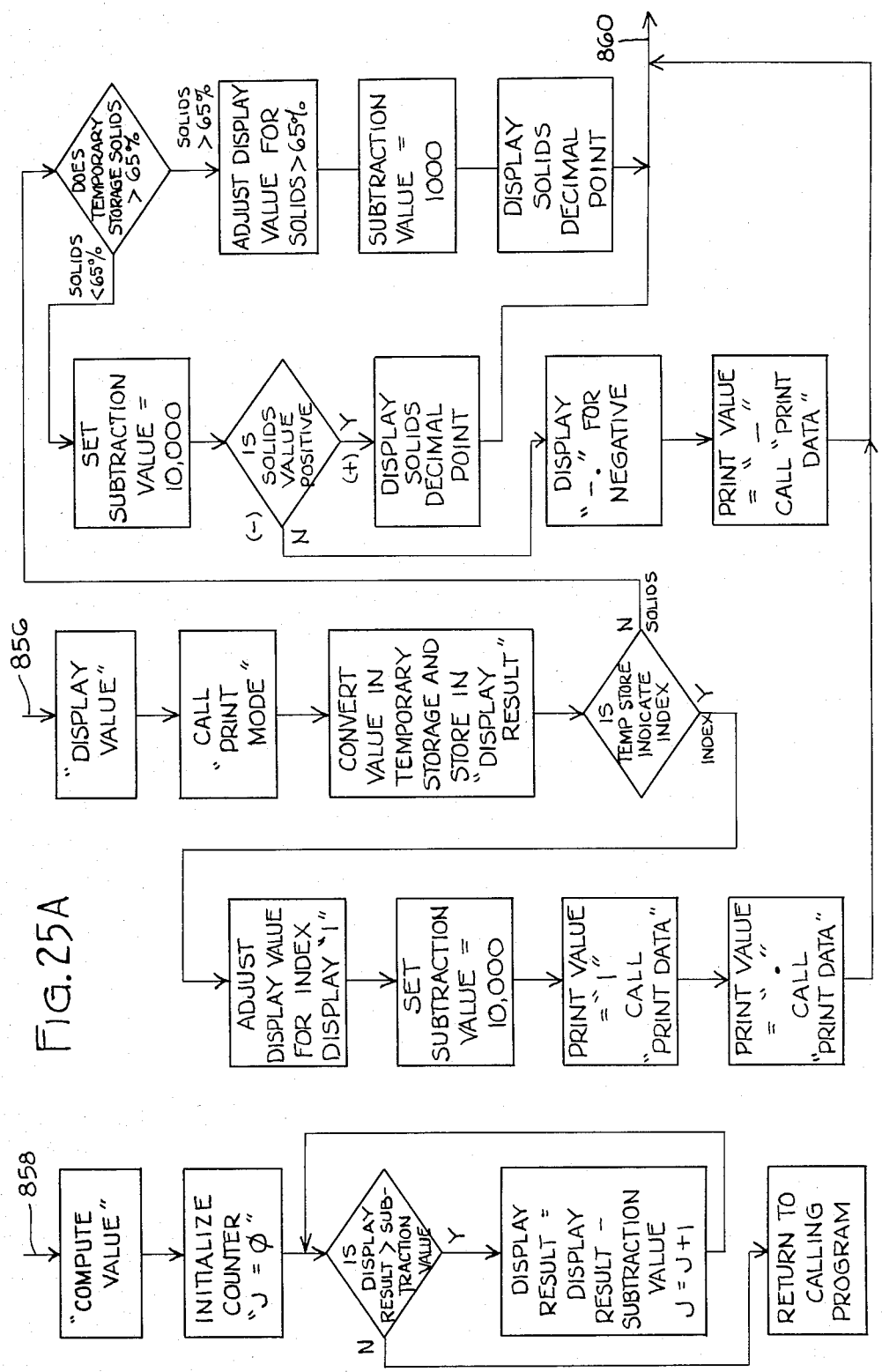
Figure 25B:
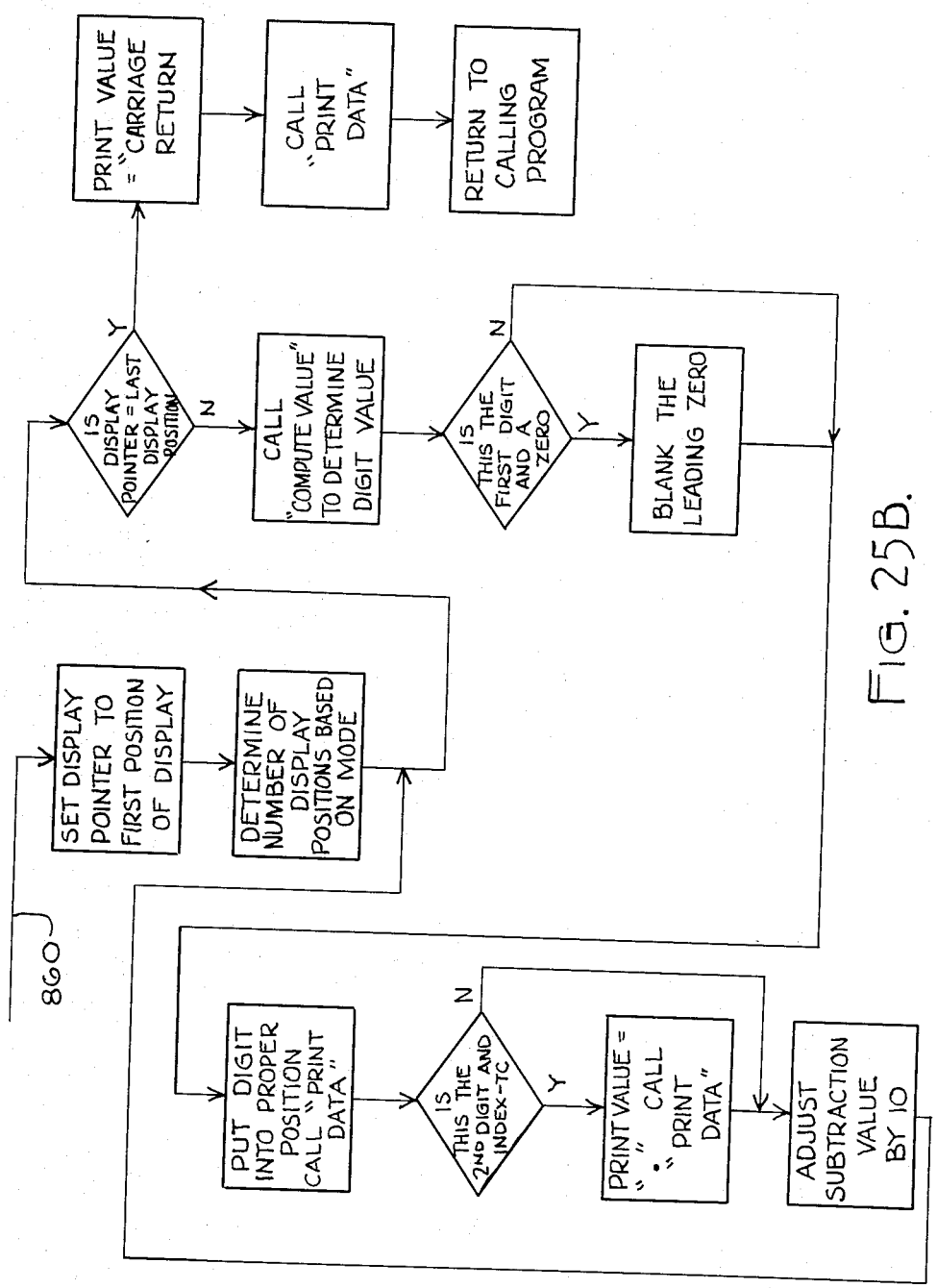

FIG. 25 illustrates the Display Value routine which is entered at 856 and is called by the main program of FIG. 15, the Execute Test routine of FIG. 16, and the Calibrate routine of FIG. 21. This module will convert the result to BCD digits format necessary for the display. It will make a determination what mode is selected and turn on the appropriate legends based on the mode selected. Associated with this is a "Compute Value" subroutine shown in FIG. 25 and entered at 858. It is done while Display Result is greater than or equal to Subtraction Value. It determines the quantity Display Result according to the relationship: Display Result=Display Result−Subtraction Value; $J=J+1$.

The Display Value routine is begun by calling the Print mode and then by converting the value in temporary storage to a whole number and storing it in Display Result. If the value in temporary storage indicates index, then the value is adjusted and "1" turned on in the display for index to adjust to display value. The subtraction value is set, various values are set for print value and a "Print Data" routine is called as indicated. Otherwise, the value is set for solids >65% or solids <65% as indicated. Then the routine proceeds as indicated by path 860 first to determine the number of display positions based on mode and then to proceed in a loop until the display pointer equals the last display position, whereupon the print value is carriage return and the Print Data routine is called. In the loop "Compute Value" is called to determine the digit value, and if it is the first digit and a zero the leading zero is blanked before proceeding further, otherwise the routine proceeds directly to the rest of the loop. In the remainder of the loop, the digit is placed in proper position, "Print Data" is called and a determination is made if the digit is the second one and the value is INDEX-TC. If so, Print Value is set, "Print Data" is called and the subtraction value is adjusted by 10, otherwise the routine proceeds directly to adjust the subtraction value as indicated. The foregoing loop repeats until the last display position is pointed to.

Figure 26:
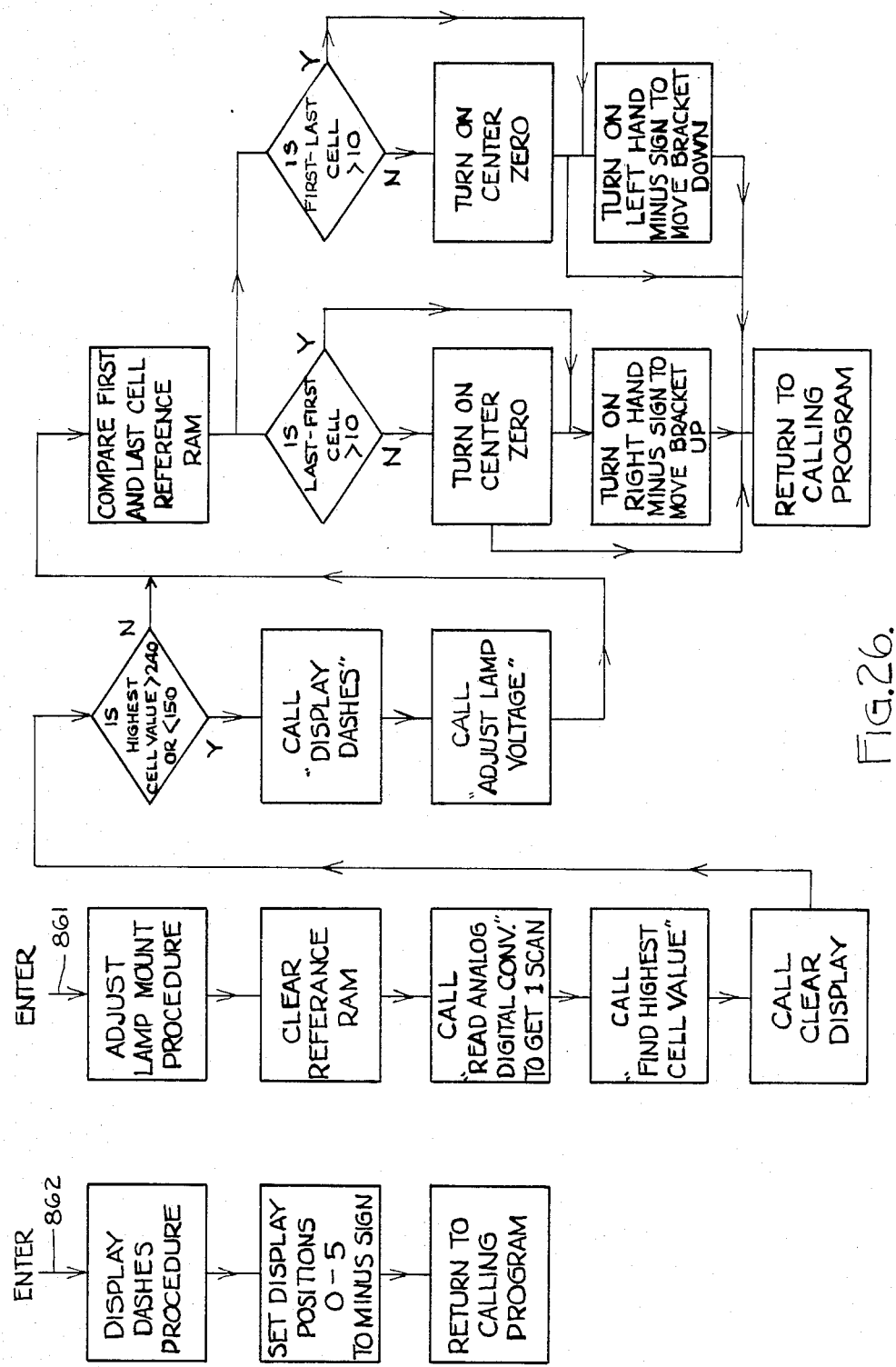

FIG. 26 shows the "Adjust Lamp Mount" routine which indicates whether or not the position of light source or lamp 72 needs to be changed and is employed during factory or service adjustments of the instrument. The routine first examines the digitized output from array 70 and examines the first and last diode amplitudes. If there is a difference, the display will show a right or left hand minus sign to indicate if the lamp mounting bracket must be moved up or down, respectively, i.e. in one direction or the other along the length of array 70. When the amplitudes are correct, the display will show a center zero. In particular, as shown in FIG. 26, the "Adjust Lamp Routine" is entered at 861 and proceeds to call the "Clear Reference Ram", "Read A/D Convertor", "Find Highest Cell Value" and "Clear Display" routines of FIGS. 13, 14, 14, and 12A respectively. If the highest cell value is not greater than 240, or less than 150, the routine proceeds directly with the comparison of the first and last cells of the reference ram, i.e. the first and last array diode amplitudes. Otherwise, the routine first calls the "Display Dashes" subroutine shown in FIG. 26 and entered at 802, next calls the "Adjust Lamp Voltage" routine of FIG. 12A and then proceeds with the comparison. As illustrated in FIG. 26, the routine performs subtractions, i.e. last cell minus first cell and first cell minus last cell. In each case if the difference is not greater than 10 a center zero is displayed to indicate that lamp assembly alignment is good. Otherwise, depending upon the results of the comparison, the display will indicate the ajustment needed as explained above.

Figure 27:
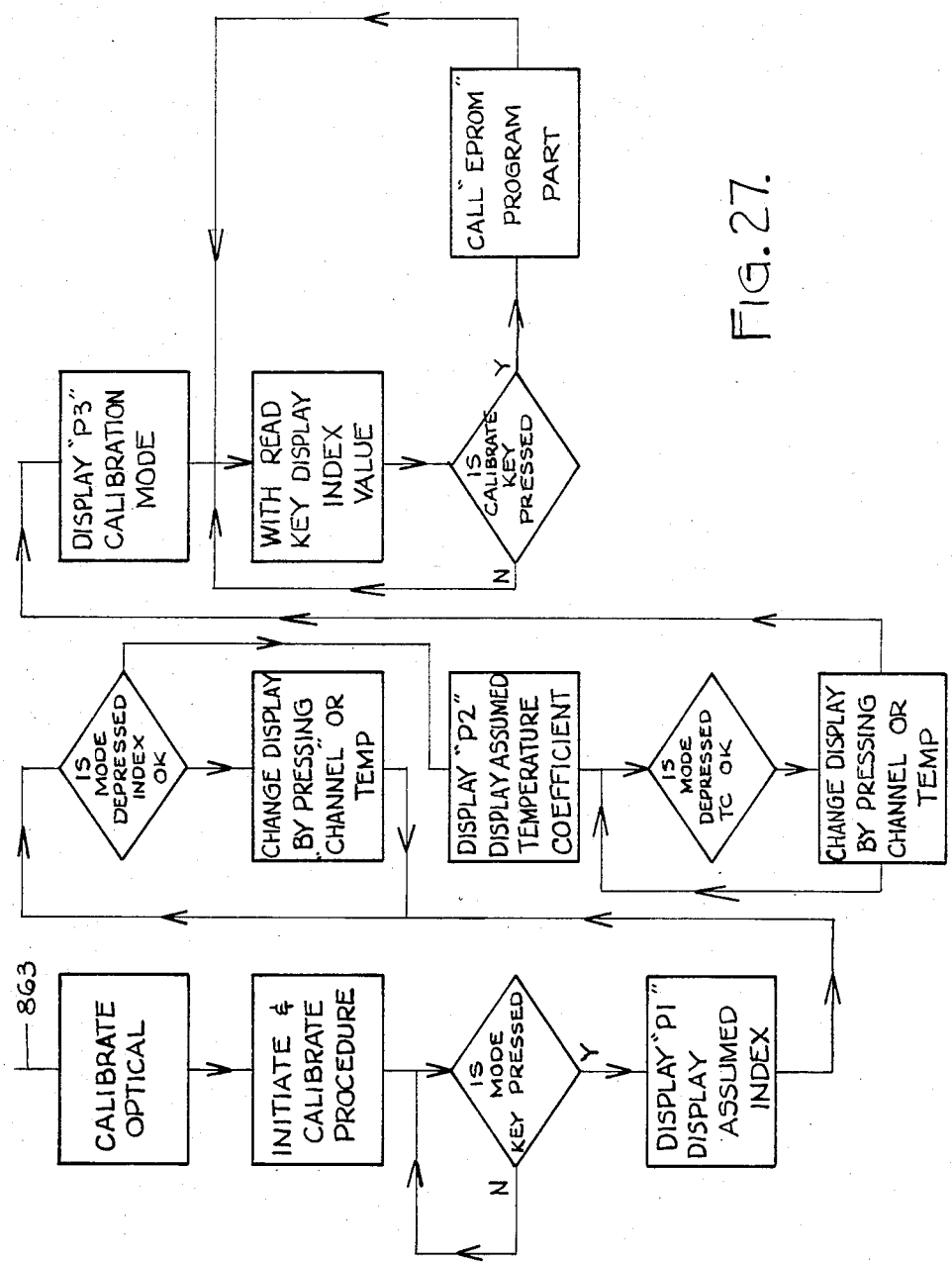

FIG. 27 illustrates the "Calibrate Optical" routine which is called for when the calibration procedure is invoked and is called by the "Execute Test Routine" of FIG. 16. The test switch is set and the keypress procedure is followed with water calibration and then calibration with oil. The routine will call up the cell crossing routine and program the EEPROM, i.e. the flip-flop component which is designated 464 in FIG. 6, with the cell number. As indicated in FIG. 27, the routine first goes through an initiate and calibrate procedure. By way of example, assume a cell value equivalent is computed by first subtracting 18369 the display value for refractive index 1.49441 and cell crossing number of 930.0 then multiply by 23 and divide by 37 to obtain the tenth cell adder. Finally add this to 9300 to obtain the cell value corresponding to the index. Next, a corrected cell value is computed by first computing the adder to the index value based on sample temperature. This includes computing the temperature and obtaining differences for either greater than or less than 25 degrees and determining the additional value for temperature different than 25 degrees. Finally the index of the sample is measured and the index value is determined with the temperature correction added.

The next procedure in the routine is to determine the value to be stored in the EEPROM. By way of example, this can be done by using a cell adjustment routine. The parameters are set to compute and find the quantity "EEPROM Number to be Stored" according to the relationship:

$$\frac{\text{Cell Cross. Equiv. of } N_D \text{ on Sample}}{10,000} = \frac{\text{Computed Cell Cross Measured}}{\text{EEPROM Number to be Stored}}$$

After this the keyboard process illustrated in FIG. 27 is followed. If a mode key is depressed, the assumed index is displayed, if the mode is not index, the routine proceeds to display the assumed temperature coefficient, and if it is index then looping occurs until the channel or temperature key is depressed. After that, the calibration mode is displayed, then the index value is displayed by pressing the read key and then when the calibrate key is pressed the EEPROM program is called.

Figure 28:
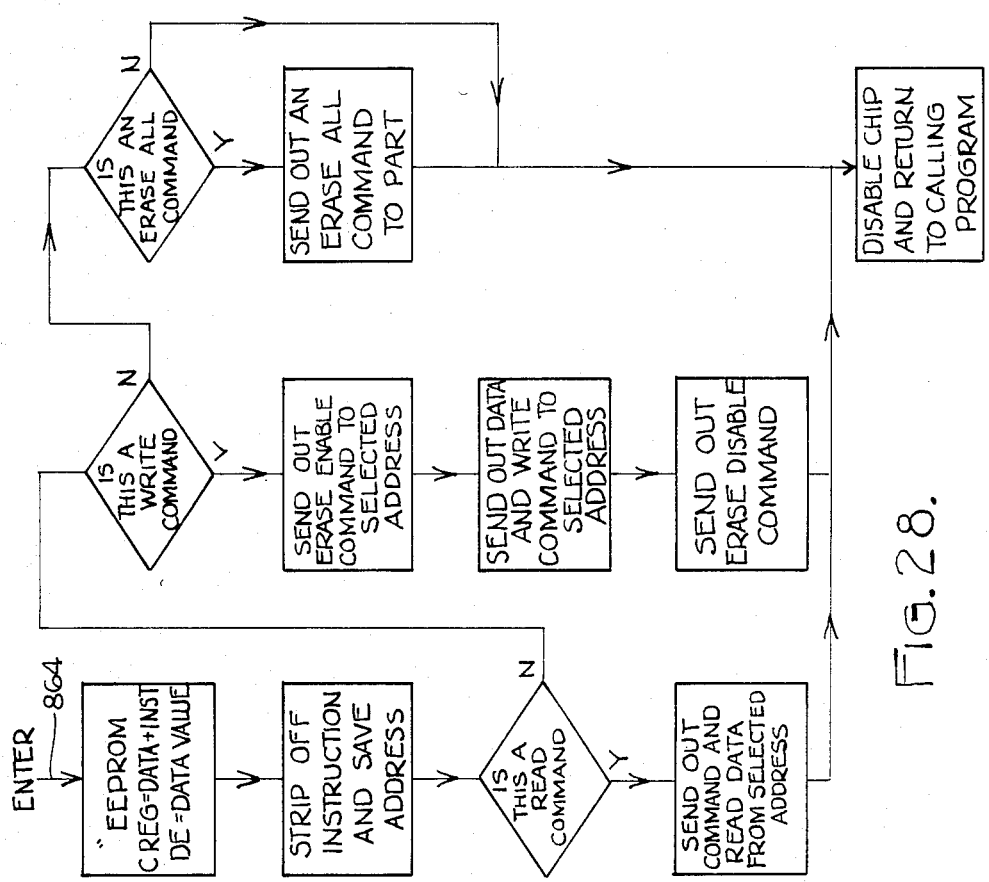

FIG. 28 illustrates the EEPROM routine which provides the low level functions to drive the EEPROM, i.e. the flip-flop component 464 in FIG. 6. All registers are used with the possibility of one value returned when the read command is recieved. Inputs to the module include the instruction commands: read, write, erase location at address, erase/write enable, erase/write disable and erase all. In the C register the instruction is in the upper 4 bits and the address in the lower 4 bits. The DE register contains the data value. As indicated in FIG. 28, after the program strips off the instruction and saves the address, it determines if the command is Read, Write or Erase All and proceeds as indicated in FIG. 28 to send out various commands. In particular, the first test is to compare to a read command and if it is not proceed to the next test, otherwise restore the proper command and call a routine to send the start bit and the packed code with address. Next, a loop counter is set up, the chip associated with EEPROM is enabled, and the chip is clocked and dummy zero ignored. Next, the data is input and masked to get the low order bit or in low order byte of the data and restore to a register. The loop counter is decremented and the data is stored. The data word is shifted one bit in the register and looped until all 16 bits are obtained.

The second test is to compare to a write command and if it is not proceed to the next test, otherwise an erase enable command is sent out to the EEPROM. Next, the location in the EEPROM pointed to by the C register is erased. This is done by obtaining the instruction and address, stripping the instruction and adding an erase command at the address, sending out the erase command at the specified address, starting the programming and sending the programming command. Then, after an appropriate time delay a command is sent out to write to the location with the 16 bit data whereupon a call is made to stop programming. After an appropriate time delay, the erase disable command is sent out to the EEPROM and the programming is stopped.

The third test is to compare to an erase all registers command, and if it is not a return is made. Otherwise, an erase all command is sent to the EEPROM and indicated in FIG. 28.

Figure 29:
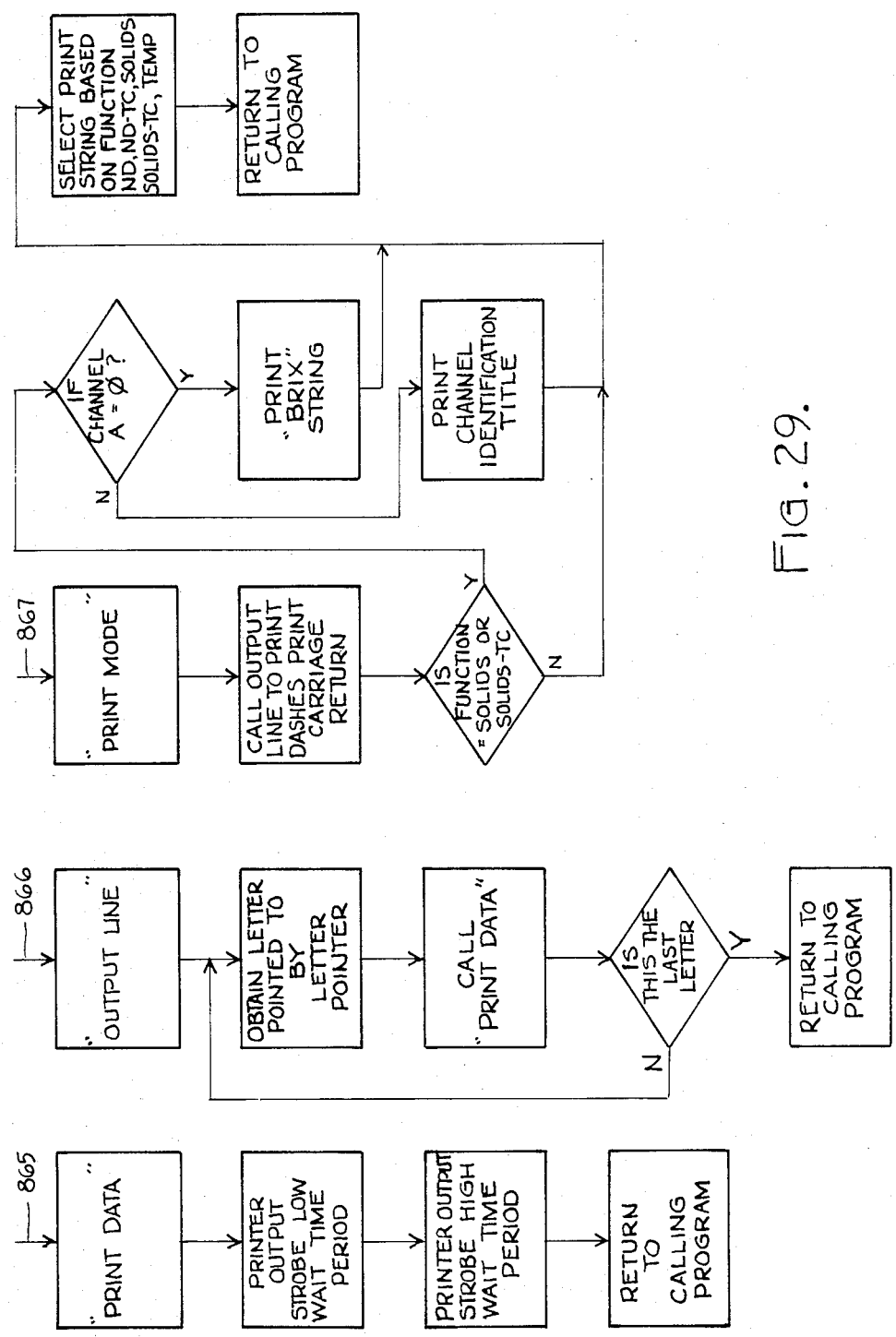

FIG. 29 shows the module which contains the low level driver for the printer. Also included are the mode selection messages that will be shown along with the display value. In a multi-channel instrument, the channel type will also be printed along with the display information. As shown in FIG. 29 there is a "Print Data" routine enetered at 865, an "Output Line" routine entered at 866 and a "Print Mode" routine entered at 867. In the "Print Data" routine, if the printer output is "Print Value" the routine waits to hold the strobe low and if the printer output is "Print Value" or a particular number, the stroke is high. The "Output Line" routine is employed to print a selected message pointed to by the quantity "Letter Pointer". In the "Print Mode" routine, if the print value is carriage routine, the output line is called to print dashes. Next a determination is made if the function selected is Solids or Solids TC. If so and if the channel number is zero than the output line is called to print "Brix". otherwise, the channel name is printed from the listing. Next, a print string is selected based on the function as indicated in FIG. 29.

FIGS. 30–34 illustrate a supporting frame 870 located within the refractometer housing 10. The frame 870 includes means for attaching therein the photoelectric means 70 and the optical means including the prism 74, mirror 86, filter 90, lenses 96 and 100, mirror 114 and lens 120 in the arrangement of FIG. 3. The frame 870 also defines therein passages therein for optical paths between the light source 72, the optical elements including mirrors and lenses, the prism 74 and the photoelectric means 70. In addition, frame 870 protects the optical means and the photoelectric means from adverse environmental effects such as temperature, contaminants, shock and vibration.

As shown in FIG. 30, frame 870 is in the form of a single casting having a pair of end portions 872 and 874, a pair of side portions, one of which is 876 in FIG. 30, and a top portion 880. The bottom of the casting is open and the end sections have 872 and 874 have outwardly extending flanges or feet portions 882 and 884, respectively.

An extension 886 is formed on the one frame end portion 874, the right-hand one as viewed in FIG. 30, which has an opening to receive in a telescoping manner a cylindrical housing 888 which contains therein the optical filter 90 and combination of lenses 96 and 100. An annular, radial flange 889 on housing 888 abuts the end face of extension 886 to control axial placement of housing 888 in extension 886. The assembly of filter 90 and lenses 96 and 100 is located near the inner end of housing 888. At the left-hand end of housing 888 as viewed in FIG. 30 there is an annular surface 890 from which there extends a formation 892 defining a lateral opening 894 and an end face disposed at an angle to the longitudinal axis of housing 888. Mirror 114 is fixed to this annular end face which establishes the desired angle of inclination of mirror 114 relative to the longitudinal axis of housing 888. The interior of housing 888 and the end formation 892 together with the lateral opening 894 define a passage for the optical paths 84 and 88 between the light source 72 and prism 74, the paths being indicated also in FIG. 3. As shown in FIG. 31, light source 72 in the form of a lamp is supported by an L-shaped adjustable bracket 898 fixed at one end to extension 886 and disposed and positioned to place the lamp 72 at the opening of housing 888 to provide light along the path 84 shown in FIG. 30.

The top portion 880 of frame 870 is provided with an opening 900, preferably circular, which receives a sub assembly including prism 74. A generally disc-shaped metal element 902 containing a central opening 904 and an annular inclined surface 906 is provided for receiving liquid to be measured and prism 74 is fixed to the lower surface of element 902 as viewed in FIG. 30 by adhesive or suitable means thereby exposing the prism surface 76 to the opening 904. The sub assembly of element 902 with prism 74 depending therefrom is supported in opening 900 in the following manner. Element 902 rests on an annular body 910 which extends a small distance outwardly of frame surface 880, has a diameter sufficiently large to receive prism 74 in close but spaced relation, and extends into the interior of frame 870. An O-ring 912 seals the junction of part 902 and body 910. Body 910 has a radially extending lip or flange 914 adjacent the innermost surface thereof. An annular L-shaped part 916 fits snugly between body 910 and opening 900 and adjacent the inner surface of frame portion 880. A flange 920 of the assembly mounting mirror 114 and lens 120 which will be described abuts the inner surface of body 910 as shown in FIG. 30 and the parts are secured together and to the frame portion 870 by a plurality of fasteners 924 in cooperation with a ring 926.

There is provided temperature sensing means operatively associated with the prism surface, i.e. surface 76, for providing an output signal indicative of the temperature of that surface. The temperature sensing means is in the form of a thermistorbead 930 on surface 76 of prism 74 adjacent the edge of opening 904 in element 902. A lead or conductor (not shown) extends across the portion of prism surface 76 beneath part 902 for connection to the refractometer circuit as previously described. There is also included means for passing a heat transmitting fluid in heat exchange relationship with prism 74. This is provided by a conduit or hose having a first section 934 for external connection as shown in FIGS. 30, 31 and extending into frame 870, a second section 936 within body 910 as shown in FIG. 30, and a third section 938 extending from frame 870 for external connection as shown in FIG. 31. There is also provided means connected to the temperature sensing means and operatively associated with the heat transmitting fluid for comparing the measured temperature of the prism surface 76 to a reference and controlling the temperature of the fluid in accordance with the comparison. As a result, there is provided a fluid or water bath around the prism for controlling the temperature. For example, some liquids such as corn syrup can be quite viscous at room temperature, and the foregoing arrangement can be used to elevate the liquid temperature, for example to 45° cel. for corn syrup.

An internal supporting body 946 is provided in frame 870 near and below prism 74 for supporting the mirror 114 and lens 120. The body 946 is integrally formed with the afore-mentioned flange 920 which is mounted to frame portion 880 as previously described, and the body is somewhat tubular in form and at the lower end as viewed in FIG. 30 has an angularly disposed end face 948 to which mirror 114 is secured. A lateral opening 950 is provided in the wall of body 946 laterally opposite the mirror 114 to provide a passage for the optical path 118 which path also is shown in FIG. 3. The central portion of body 946 receives a lens piece or holder element 952 for holding the lens 120. The interior of body 946 defines the optical path between lens 120 and mirror 114. The angle is set by the disposition of body 946 relative to flange 920.

The refractometer of the present invention often finds use in industrial process locations where it is subjected to adverse environmental effects such as temperature, contaminants, shock and vibration. The photoelectric means and the optical means of the refractometer including the prism and optical elements are mounted to the rigid supporting frame described hereinabove, which, in turn, is carried by and located within the refractometer housing. This rugged mounting and isolation protects the optical means and the photoelectric means from such adverse environmental effects.

There is also provided means for adjusting the positional location of the photoelectric means or linear scan array 70. As shown in FIGS. 30 and 31, array 70 is elongated and rectangular, disposed with the longitudinal axis thereof extending generally vertically thereof in FIGS. 30 and 31. Array 70 is secured to a first plate 960 by fasteners 962 and is secured to a second plate 964 by fasteners 966. Plate 964, is secured to frame portion 872 by fasteners 968. Array 70 is adjusted vertically by loosening fasteners 968 and moving the entire assembly up and down as viewed in FIGS. 30 and 32. In this connection, the openings in plate 964 for fasteners 968 can be slightly elongated in the vertical direction. Array 70 is adjusted in a horizontal direction by loosening fasteners 966 and moving plate 960 laterally or horizontally to the desired position.

The refractometer of the present invention is provided with a removable cover for the assembly over prism 74 to facilitate cleaning of the surface surrounding the same. The assembly includes a block 976 which is provided with a central circular opening 978 to accomodate the peripheral edge of body 902 as shown in FIGS. 33 and 34. The broken lines in FIG. 33 indicate circular edges of block 976 including edges of the block and of the frame shown in FIG. 30. Block 976 is fixed in place on body 902 by suitable means such as the set screws indicated 980 in FIGS. 33 and 34. Block 976 is provided with a pair of hinges generally designated 982 and 894. Hinge 982 has a spring 986 and a pin 988. Similarly, hinge 984 has a spring 990 and a pin 992. A generally flat cover member 994 has a pair of side flanges, one of which is designated 996 each of which is provided with a bore or opening to receive a corresponding one of the hinge pins 988 and 992. Thus, the hinge pins extend into the cover flange connecting it pivotally to the body 902 whereupon it can be raised and lowered during use of the refractometer. When it is desired to remove cover 994 to facilitate cleaning the surrounding area of the refractometer, pins 988 and 992 are pushed inwardly by a suitable tool against the force of the corresponding springs to enable cover 994 to be removed.

It is therefore apparent that the present invention accomplishes its intended objects. While an embodiment of the present invention has been described in detail, this is for the purpose of illustration, not limitation.

I claim:

1. An automatic refractometer comprising:
   (a) a linear scanned array comprising a plurality of photoelectric elements, each element providing an output pulse during a scan and the amplitude of each pulse being determined by the amount of illumination of the corresponding element by incident light;
   (b) optical means for directing light onto said array, the particular photoelectric elements of said array which are illuminated by said light being determined by the index of refraction of a light transmitting substance placed in operative association with said optical means;
   (c) means for converting the signals from said linear scanned array into digital signals containing information as to the amplitudes of said signals from said array;
   (d) digital processing circuit means for storing respective digital signals from reference and sample substances placed in operative association with said optical means and for computing the index of refraction of the sample substance by means of a comparison of the stored reference and sample signal information, said digital processing circuit means including means for matching reference curve data and sample curve data and searching for the critical angle of total reflection indicated by rapidly increasing amplitude of said signals from said array resulting from rapidly increasing light intensity; and
   (e) means for providing a read out of the result computed by said digital processing circuit means.

2. A refractometer according to claim 1, wherein said digital processing circuit means further includes means to calculate the percent solids in the sample substance.

3. A refractometer according to claim 2, further including means operatively connected to said digital processing circuit means to select between said refractive index and percent solids calculations for determining which result is provided by said read out means.

4. A refractometer according to claim 1, further including means for measuring the temperature of the sample substance when placed in operative association with said optical means and wherein said digital processing circuit means includes means for comparing the measured temperature of the substance with a reference temperature and for applying a temperature correction to the computed index of refraction.

5. A refractometer according to claim 4, further including means operatively connected to said digital procesing circuit means to select between uncompensated and temperature compensated refractive index calculations to determine which result is provided by said read out means.

6. A refractometer according to claim 1, wherein said read out means comprises display means for providing a visual indication of the result computed by said digital processing circuit means.

7. A refractometer according to claim 1, wherein said read out means comprises a printer for providing a hard copy record of the result computed by said digital processing circuit means.

8. A refractometer according to claim 1, wherein said digital processing circuit means comprises:
   (a) a sample RAM for storing information from said digital signals from sample substances;
   (b) a reference RAM for storing information from reference substances;
   (c) means for comparing on an individual basis data from said sample RAM to data from said reference RAM until a match occurs; and
   (d) means for interpolating the information from said match to split said information into a plurality of parts to achieve desired accuracy.

9. An automatic refractometer comprising:
   (a) photosensitive means having a narrow dynamic range for providing output signals as a function of the amount and location of light incident thereon;
   (b) optical means for directing light onto said photosensitive means, the amount and location of light incident on said photosensitive means being determined by the index of refraction of a light transmitting substance placed in operative association with said optical means;
   (c) means for converting the signals from said photosensitive means into digital signals containing information as to a characteristic of said signals from said photosensitive means;
   (d) digital processing circuit means for storing respective digital signals from reference and sample substances placed in operative association with said optical means and for computing the index of refraction of the sample substance by means of a comparison of the stored reference and sample signal information;
   (e) means for providing a read out of the result computed by said digital processing circuit means;
   (f) said digital processing circuit means including a plurality of channels for containing information to provide different interpretations of the index of refraction computed by said digital processing circuit means; and
   (g) means operatively connected to said channels for selecting a particular channel to be utilized.

10. An automatic refractometer comprising:
    (a) photosensitive means having a narrow dynamic range for providing output signals as a function of the amount and location of light incident thereon;
    (b) optical means for directing light onto said photosensitive means, the amount and location of light incident on said photosensitive means being determined by the index of refraction of a light transmitting substance placed in operative association with said optical means;
    (c) means for converting the signals from said photosensitive means into digital signals containing information as to a characteristic of said signals from said photosensitive means;
    (d) digital processing circuit means for storing respective digital signals from reference and sample substances placed in operative association with said optical means and for computing the index of refraction of the sample substance by means of a comparison of the stored reference and sample signal information, said digital processing circuit means including means for matching reference curve data and sample curve data and searching for the critical angle of total reflection indicated by rapidly increasing amplitude of said signals from said array resulting from rapidly increasing light intensity;

(e) means for providing a read out of the result computed by said digital processing circuit means; and (f) means for connecting said digital processing circuit means to external data processing means for re-programming said digital processing circuit means to accommodate changes in characteristics relating to substances and affecting the computations of index of refraction.

11. In a refractometer having linear scanned array of photoelectric elements and an optical system including a prism for directing light onto said array at a location influenced by the index of refraction of a substance to which said prism is exposed, the improvement comprising:

(a) peak detector circuit means operatively connected to said array for detecting the peak amplitudes of signals obtained from said array during scanning thereof, said peak detector circuit means comprising means responsive to the rise of each array signal to a peak amplitude and means for holding a signal level corresponding to the peak level of each said array signal as said array signal falls in amplitude for a time at least equal to the acquisition time of said converter means; and (b) analog to digital converter means operatively connected to said peak detector circuit means for providing digital signals containing information as to peak amplitudes of said array signals.

12. In a refractometer having a linear scanned array of photoelectric elements for providing output signals as a function of the amount and location of light incident thereon and optical means including a light source of controllable intensity for directing light onto said array, the amount and location of light incident on said array being determined by the index of refraction of a light transmitting substance placed in operative association with said optical means, the improvement comprising:

signal processing means operatively coupled to said array and connected in controlling relation to digital to analog converter means connected to said light source, said signal processing means reading the maximum signal amplitude for each scan of said array and comparing said signals to to a predetermined maximum for controlling said digital to analog converter means to adjust the intensity of light from said source according to the results of the comparison.

13. In a refractometer including photoelectric means having a narrow dyanmic range for providing output signals having a characteristic determined by the manner in which light is incident thereon and optical means including a light source and a prism for receiving light along an optical path from said source and having a surface to receive substances being examined for directed light onto said photoelectric means in a manner determined by the index of refraction of a light transmitting substance in operative contact with said prism surface, the improvement comprising:

(a) interference filter means havng a relatively narrow bandwidth and located along said optical path between said source and said prism;

(b) a first lens between said source and said filter for providing substantially parallel rays of light into said filter; and (c) a second lens between said filter and said prism for concentrating the output light from said filter.

14. A method for determining the refractive index of a substance comprising the steps of:

(a) providing a linear scan array of photoelectric elements and an optical system including a prism for directing light onto said array at a location influenced by the index of refraction of a substance to which said prism is exposed;

(b) exposing said prism to air and directing light onto said array in a manner influenced by the index of refraction of air;

(c) scanning the array and processing the signals obtained therefrom to provide a signal representation of a total illumination curve;

(d) applying a scale factor to said total illumination curve to provide a reference curve;

(e) exposing said prism to a sample substance and directing light onto said array in a manner influenced by the index of refraction of said substance;

(f) scanning the array and processing the signals obtained therefrom to provide a signal representation of a sample curve;

(g) processing the signals representing said reference and sample curves to determine the point of crossover of said sample curve with respect to said reference curve to determine the critical angle from the refraction; and (h) utilizing the determined crossover point to calculate the index of refraction of said sample substance.

15. A method according to claim 14, further including the step of utilizing the calculated index of refraction to determine the precent solids concentration of said substance.

16. A method according to claim 14 wherein said steps of processing the signals obtained from scanning the array both comprise digitizing said array signals.

17. A method according to claim 16, wherein said digitizing said array signals comprises the steps of:

(a) detecting the peak amplitude of each array signal; and (b) converting the peak detected array signal into a digital signal containing amplitude information.

18. A method according to claim 17, wherein said step of detecting the peak amplitude of each array signal comprises:

(a) detecting the rise of each array signal to a peak amplitude; and (b) holding a signal level corresponding to the peak level of each array signal as said array signal falls in amplitude for a time at least equal to the time for acquiring or converting into said digital signal.

19. A method according to claim 14, wherein said step of processing includes:

(a) comparing data on an individual basis until a match between reference and sample occurs; and (b) interpolating to split the crossover information into a plurality of parts to obtain desired accuracy.

20. In a refractometer including a housing having a formation thereon externally accessible for receiving substances to be examined, photoelectric means for providing output signals having a characteristic determined by the manner in which light is incident thereon, and optical means including a prism having a surface operatively associated with said housing formation to receive substances being examined for directing light onto said photoelectric means in the manner determined by the index of refraction of a light transmitting substance in operative contact with said prism surface and optical elements for directing light from a source to said prism and for directing light from said prism to said photoelectric means, the improvement comprising:

a rigid supporting frame in the form of a single casting carried by and located within said housing and means for attaching said photoelectric means and said optical means including said prism and said optical elements to said frame, said frame defining therein passages for optical paths between said light source, optical elements, prism and photoelectric means, said frame protecting said optical means and said photoelectric means from adverse environmental effects such as temperature, contaminates, shock and vibration.

21. In a refractometer including a housing having a surface and a formation thereon externally accessible for receiving substances to be examined, photoelectric means for providing output signals having a characteristic determined by the manner in which light is incident thereon and optical means including a prism having a surface operatively associated with said housing formation to receive substances being examined for directing light onto said photoelectric means in a manner determined by the index of refraction of a light transmitting substance in operative contact with said prism surface, the improvement comprising:

a cover element associated with said formation, hinge means for pivotally connecting said cover element to said housing adjacent said formation for allowing manual movement of said cover element between a position covering said formation preventing external access thereto and a position uncovering said information and exposing said formation for external access thereto, and means operatively associated with said hinge means for permitting removal of said cover element from said housing to facilitate cleaning of said formation and the adjacent portion of said housing surface.

22. In a refractometer including photoelectric means having a narrow dynamic range for providing output signals having a characteristic determined by the manner in which light is incident thereon and optical means including a light source and a prism for receiving light along an optical path from said source and having a surface to receive substances being examined for directing light onto said photoelectric means in a manner determined by the index of refraction of a light transmitting substance in operative contact with said prism surface, the improvement comprising:

temperature sensing means on said prism surface for providing an output signal indicative of the temperature of said prism surface.

23. Apparatus according to claim 22, wherein said output signals from said photoelectric means are processed by digital circuit means including a microprocessor, and further including:

(a) solid state timer means having an input connected to said temperature sensing means and an output, said timer means converting said output signal from said temperature sensing means to pulses of proportional frequency; and (b) flip-flop means connected to said timer means and to said microprocessor for applying said pulses to said microprocessor.

* * * * *